US012589025B2

(12) United States Patent
Badawi et al.

(10) Patent No.: US 12,589,025 B2
(45) Date of Patent: Mar. 31, 2026

(54) INTRAOCULAR DEVICES, SYSTEMS, AND METHODS

(71) Applicant: Sight Sciences, Inc., Menlo Park, CA (US)

(72) Inventors: Paul Badawi, Atherton, CA (US); David Y. Badawi, Glenview, IL (US); Daniel O'Keeffe, San Francisco, CA (US)

(73) Assignee: SIGHT SCIENCES, INC., Menlo Park, CA (US)

( * ) Notice: Subject to any disclaimer, the term of this patent is extended or adjusted under 35 U.S.C. 154(b) by 950 days.

(21) Appl. No.: 17/827,573

(22) Filed: May 27, 2022

(65) Prior Publication Data

US 2022/0378612 A1     Dec. 1, 2022

Related U.S. Application Data

(60) Provisional application No. 63/194,824, filed on May 28, 2021.

(51) Int. Cl.
*A61F 9/00*               (2006.01)
(52) U.S. Cl.
CPC ................................. *A61F 9/0017* (2013.01)
(58) Field of Classification Search
CPC .... A61F 9/0008; A61F 9/0017; A61K 9/0051
See application file for complete search history.

(56) References Cited

U.S. PATENT DOCUMENTS

| | | | |
|---|---|---|---|
| 4,553,545 A | 11/1985 | Maass et al. | |
| 4,863,457 A | 9/1989 | Lee | |

| | | | |
|---|---|---|---|
| 5,147,647 A | 9/1992 | Darougar | |
| 5,180,362 A | 1/1993 | Worst | |
| 5,360,399 A | 11/1994 | Stegmann | |
| 5,411,952 A | 5/1995 | Kaswan | |
| 5,486,165 A | 1/1996 | Stegmann | |
| 5,824,086 A | 10/1998 | Silvestrini | |
| 5,830,173 A | 11/1998 | Avery et al. | |
| 6,331,313 B1 | 12/2001 | Wong et al. | |
| 6,375,642 B1 | 4/2002 | Grieshaber et al. | |
| 6,413,245 B1 | 7/2002 | Yaacobi et al. | |
| 6,468,307 B1 | 10/2002 | Baikoff et al. | |
| 6,494,857 B1 | 12/2002 | Neuhann | |

(Continued)

FOREIGN PATENT DOCUMENTS

| | | |
|---|---|---|
| CA | 2244646 A1 | 2/1999 |
| EP | 3 967 297 A1 | 3/2022 |

(Continued)

OTHER PUBLICATIONS

Arkell, S.M. et al. (1987). "The prevalence of glaucoma among Eskimos of Northwest Alaska," Arch. Ophthalmol. 105:482-485.

(Continued)

*Primary Examiner* — Laura A Bouchelle

(74) *Attorney, Agent, or Firm* — Cooley LLP

(57)               ABSTRACT

The present disclosure relates to intraocular implants for treating a condition of the eye, wherein the implant is configured to deliver a drug to the eye. The present disclosure also relates to methods of treating a condition of the eye by delivering a drug from intraocular implants to the posterior chamber (e.g., sulcus), iridocorneal angle, sclera, cornea, limbus, and vitreous.

68 Claims, 29 Drawing Sheets

(56) References Cited

U.S. PATENT DOCUMENTS

| | | |
|---|---|---|
| 6,508,779 B1 | 1/2003 | Suson |
| 6,533,768 B1 | 3/2003 | Hill |
| 6,558,342 B1 | 5/2003 | Yaron et al. |
| 6,666,841 B2 | 12/2003 | Gharib et al. |
| 6,682,348 B2 | 1/2004 | Lawter et al. |
| 6,719,750 B2 | 4/2004 | Varner et al. |
| 6,736,791 B1 | 5/2004 | Tu et al. |
| 6,756,058 B2 | 6/2004 | Brubaker et al. |
| 6,881,198 B2 | 4/2005 | Brown |
| 7,048,946 B1 | 5/2006 | Wong et al. |
| 7,135,009 B2 | 11/2006 | Tu et al. |
| 7,186,232 B1 | 3/2007 | Smedley et al. |
| 7,192,412 B1 | 3/2007 | Zhou et al. |
| 7,594,899 B2 | 9/2009 | Pinchuk et al. |
| 7,699,609 B2 | 4/2010 | Lawter et al. |
| 7,714,024 B2 | 5/2010 | Hughes et al. |
| 7,799,336 B2 | 9/2010 | Hughes |
| 7,909,789 B2 | 3/2011 | Badawi et al. |
| 7,919,111 B2 | 4/2011 | Chudzik et al. |
| 7,998,108 B2 | 8/2011 | Nazzaro et al. |
| 8,206,737 B2 | 6/2012 | Hughes |
| 8,267,995 B2 | 9/2012 | Castillejos |
| 8,287,482 B2 | 10/2012 | Badawi et al. |
| 8,298,578 B2 | 10/2012 | De Juan, Jr. et al. |
| 8,308,701 B2 | 11/2012 | Horvath et al. |
| 8,308,707 B2 | 11/2012 | Santini, Jr. et al. |
| 8,349,005 B2 | 1/2013 | Murata |
| 8,439,972 B2 | 5/2013 | Badawi et al. |
| 8,506,987 B2 | 8/2013 | Shiah et al. |
| 8,512,738 B2 | 8/2013 | Edelman et al. |
| 8,529,622 B2 | 9/2013 | Badawi et al. |
| 8,568,391 B2 | 10/2013 | Kearns et al. |
| 8,585,629 B2 | 11/2013 | Grabner et al. |
| 8,629,185 B2 | 1/2014 | Ambrus et al. |
| 8,663,194 B2 | 3/2014 | Ambati et al. |
| 8,673,341 B2 | 3/2014 | Hughes |
| 8,715,712 B2 | 5/2014 | de Juan, Jr. et al. |
| 8,758,290 B2 | 6/2014 | Horvath et al. |
| 8,790,293 B2 | 7/2014 | Nazzaro et al. |
| 8,828,070 B2 | 9/2014 | Romoda et al. |
| 8,852,137 B2 | 10/2014 | Horvath et al. |
| 8,876,898 B2 | 11/2014 | Badawi et al. |
| 8,894,603 B2 | 11/2014 | Badawi et al. |
| 8,945,214 B2 | 2/2015 | Bhagat et al. |
| 8,993,615 B2 | 3/2015 | Zack et al. |
| 9,095,404 B2 | 8/2015 | Ambati et al. |
| 9,095,412 B2 | 8/2015 | Badawi et al. |
| 9,149,428 B2 | 10/2015 | Spada et al. |
| 9,216,109 B2 | 12/2015 | Badawi et al. |
| 9,233,070 B2 | 1/2016 | Edelman et al. |
| 9,327,059 B2 | 5/2016 | Huang et al. |
| 9,370,443 B2 | 6/2016 | Badawi et al. |
| 9,421,126 B2 | 8/2016 | Alster et al. |
| 9,480,598 B2 | 11/2016 | Clauson et al. |
| 9,486,361 B2 | 11/2016 | Badawi et al. |
| 9,492,316 B2 | 11/2016 | Ghebremeskel et al. |
| 9,522,153 B2 | 12/2016 | Pujara |
| 9,592,151 B2 | 3/2017 | Rangel-Friedman et al. |
| 9,655,882 B2 | 5/2017 | Zack et al. |
| 9,668,915 B2 * | 6/2017 | Haffner ................ A61F 9/0017 |
| 9,750,636 B2 | 9/2017 | Rubin et al. |
| 9,782,346 B2 | 10/2017 | Venkatraman et al. |
| 9,801,891 B2 | 10/2017 | Pujara |
| 9,855,167 B2 | 1/2018 | Badawi et al. |
| 9,877,973 B2 | 1/2018 | Ambati et al. |
| 9,895,258 B2 | 2/2018 | Badawi et al. |
| 9,980,901 B2 | 5/2018 | Ni |
| 9,980,974 B2 | 5/2018 | Ghebremeskel et al. |
| 9,987,223 B2 | 6/2018 | Ni |
| 10,004,636 B2 | 6/2018 | Alster et al. |
| 10,058,505 B2 | 8/2018 | Mousavikhamene et al. |
| 10,058,640 B2 | 8/2018 | Blake et al. |
| 10,064,819 B2 | 9/2018 | Ambati et al. |
| 10,076,492 B2 | 9/2018 | Edelman et al. |
| 10,111,776 B2 | 10/2018 | Basinger et al. |
| 10,149,819 B2 | 12/2018 | Ni |
| 10,149,820 B2 | 12/2018 | Ni |
| 10,179,066 B2 | 1/2019 | Badawi et al. |
| 10,188,550 B2 | 1/2019 | Andino et al. |
| 10,188,551 B2 | 1/2019 | Rangel-Friedman et al. |
| 10,195,079 B2 | 2/2019 | Horvath et al. |
| 10,206,813 B2 | 2/2019 | Haffner et al. |
| 10,206,814 B2 | 2/2019 | Hardten et al. |
| 10,231,926 B2 | 3/2019 | Shiah et al. |
| 10,245,178 B1 | 4/2019 | Heitzmann et al. |
| 10,258,503 B2 | 4/2019 | Bianchi et al. |
| 10,265,215 B2 | 4/2019 | De Juan, Jr. et al. |
| 10,272,098 B2 | 4/2019 | Zhong et al. |
| 10,278,919 B2 | 5/2019 | Robinson et al. |
| 10,278,920 B1 | 5/2019 | Peyman |
| 10,299,958 B2 | 5/2019 | Badawi et al. |
| 10,314,742 B2 | 6/2019 | Badawi et al. |
| 10,342,703 B2 | 7/2019 | Siewert et al. |
| 10,398,594 B2 | 9/2019 | Higuchi |
| 10,398,597 B2 | 9/2019 | Badawi et al. |
| 10,398,707 B2 | 9/2019 | Hughes |
| 10,406,029 B2 | 9/2019 | Tu et al. |
| 10,406,030 B2 | 9/2019 | Badawi et al. |
| 10,441,543 B2 | 10/2019 | Spada et al. |
| 10,449,145 B2 | 10/2019 | Csaky |
| 10,456,293 B2 | 10/2019 | Rubin et al. |
| 10,470,924 B2 | 11/2019 | Erickson et al. |
| 10,478,335 B2 | 11/2019 | Lerner |
| 10,485,550 B2 | 11/2019 | Epstein et al. |
| 10,524,957 B2 | 1/2020 | Lerner |
| 10,588,855 B2 | 3/2020 | Ambati et al. |
| 10,603,209 B2 | 3/2020 | de Juan, Jr. et al. |
| 10,610,406 B2 | 4/2020 | Galloway et al. |
| 10,617,563 B2 | 4/2020 | Jarrett et al. |
| 10,624,904 B2 | 4/2020 | Williams et al. |
| 10,632,012 B2 | 4/2020 | Cadden et al. |
| 10,656,152 B2 | 5/2020 | De Juan, Jr. et al. |
| 10,667,947 B2 | 6/2020 | Horvath et al. |
| 10,736,774 B2 | 8/2020 | Alster et al. |
| 10,758,409 B2 | 9/2020 | Franco et al. |
| 10,813,788 B2 | 10/2020 | de Juan, Jr. et al. |
| 10,813,789 B2 | 10/2020 | Haffner et al. |
| 10,835,416 B2 | 11/2020 | De Juan et al. |
| 10,857,027 B2 | 12/2020 | Badawi et al. |
| 10,874,605 B2 | 12/2020 | Nivaggioli et al. |
| 10,881,608 B2 | 1/2021 | Edelman et al. |
| 10,881,609 B2 | 1/2021 | Csaky |
| 10,888,453 B2 | 1/2021 | Badawi et al. |
| 10,905,587 B2 | 2/2021 | Lerner |
| 10,905,591 B1 | 2/2021 | Ianchulev |
| 10,980,671 B2 | 4/2021 | Hill |
| 10,980,741 B2 | 4/2021 | Ni |
| 11,090,188 B2 | 8/2021 | Badawi et al. |
| 11,116,660 B2 | 9/2021 | Badawi et al. |
| 11,166,847 B2 | 11/2021 | Badawi et al. |
| 11,224,602 B2 | 1/2022 | Stark et al. |
| 11,259,961 B2 | 3/2022 | Ianchulev |
| 11,318,043 B2 | 5/2022 | Heitzmann et al. |
| 11,344,447 B2 | 5/2022 | Badawi et al. |
| 11,389,327 B2 | 7/2022 | Badawi et al. |
| 11,389,328 B2 | 7/2022 | Badawi et al. |
| 11,419,762 B2 | 8/2022 | Ianchulev |
| 11,419,886 B2 | 8/2022 | Badawi et al. |
| 11,458,041 B2 | 10/2022 | Silverberg et al. |
| 11,471,324 B2 | 10/2022 | Badawi et al. |
| 11,504,270 B1 | 11/2022 | Badawi et al. |
| 11,554,134 B2 | 1/2023 | Badawi et al. |
| 11,617,679 B2 | 4/2023 | Badawi et al. |
| 11,622,935 B2 | 4/2023 | Blizzard et al. |
| 11,857,460 B2 | 1/2024 | Badawi et al. |
| 11,865,041 B2 | 1/2024 | Badawi et al. |
| 11,872,158 B2 | 1/2024 | Badawi et al. |
| 11,877,954 B2 | 1/2024 | Badawi et al. |
| 11,925,580 B2 | 3/2024 | Ianchulev |
| 11,925,657 B2 | 3/2024 | Badawi et al. |
| 11,951,037 B2 | 4/2024 | Badawi et al. |
| 12,042,428 B2 | 7/2024 | Badawi et al. |
| 12,127,973 B2 | 10/2024 | Badawi et al. |
| 12,127,974 B2 | 10/2024 | Badawi et al. |

(56) References Cited

U.S. PATENT DOCUMENTS

| | | |
|---|---|---|
| 12,171,689 B2 | 12/2024 | Badawi et al. |
| 12,213,914 B2 | 2/2025 | Badawi et al. |
| 12,310,891 B2 | 5/2025 | Badawi et al. |
| 12,350,192 B2 | 7/2025 | Badawi et al. |
| 2002/0055753 A1 | 5/2002 | Silvestrini |
| 2002/0143284 A1 | 10/2002 | Tu et al. |
| 2002/0165478 A1 | 11/2002 | Gharib et al. |
| 2003/0060752 A1 | 3/2003 | Bergheim et al. |
| 2003/0093084 A1 | 5/2003 | Nissan et al. |
| 2003/0186191 A1 | 10/2003 | Lawter et al. |
| 2004/0029843 A1 | 2/2004 | Lawter |
| 2004/0073303 A1 | 4/2004 | Schanzlin et al. |
| 2004/0102719 A1 | 5/2004 | Keith et al. |
| 2004/0102729 A1 | 5/2004 | Haffner et al. |
| 2004/0147870 A1 | 7/2004 | Burns et al. |
| 2004/0152042 A1 | 8/2004 | Lawter et al. |
| 2004/0193262 A1 | 9/2004 | Shadduck |
| 2004/0208910 A1 | 10/2004 | Ashton et al. |
| 2004/0215133 A1 | 10/2004 | Weber et al. |
| 2004/0236343 A1 | 11/2004 | Taylor et al. |
| 2004/0254520 A1 | 12/2004 | Porteous et al. |
| 2004/0260228 A1 | 12/2004 | Lynch et al. |
| 2005/0038334 A1 | 2/2005 | Lynch et al. |
| 2005/0090807 A1 | 4/2005 | Lynch et al. |
| 2005/0101967 A1 | 5/2005 | Weber et al. |
| 2005/0244475 A1 | 11/2005 | Edelman et al. |
| 2005/0266047 A1 | 12/2005 | Tu et al. |
| 2005/0271705 A1 | 12/2005 | Hughes et al. |
| 2005/0277864 A1 | 12/2005 | Haffner et al. |
| 2005/0281861 A1 | 12/2005 | Hughes et al. |
| 2006/0034891 A1 | 2/2006 | Lawin et al. |
| 2006/0067979 A1 | 3/2006 | Kunzler et al. |
| 2006/0110429 A1 | 5/2006 | Reiff et al. |
| 2006/0116626 A1 | 6/2006 | Smedley et al. |
| 2006/0149194 A1 | 7/2006 | Conston et al. |
| 2006/0182783 A1 | 8/2006 | Hughes et al. |
| 2006/0195187 A1 | 8/2006 | Stegmann et al. |
| 2006/0257452 A1 | 11/2006 | Hughes et al. |
| 2007/0066541 A1 | 3/2007 | Hughes et al. |
| 2007/0233037 A1 | 10/2007 | Gifford, III et al. |
| 2008/0057106 A1 | 3/2008 | Erickson et al. |
| 2008/0058704 A1 | 3/2008 | Hee et al. |
| 2008/0112922 A1 | 5/2008 | Hughes et al. |
| 2008/0112923 A1 | 5/2008 | Hughes et al. |
| 2008/0131484 A1 | 6/2008 | Robinson et al. |
| 2008/0161741 A1 | 7/2008 | Bene et al. |
| 2008/0299202 A1 | 12/2008 | Marenzi et al. |
| 2009/0036819 A1 | 2/2009 | Tu et al. |
| 2009/0214619 A1 | 8/2009 | Reiff et al. |
| 2009/0227934 A1 | 9/2009 | Euteneuer et al. |
| 2009/0258924 A1 | 10/2009 | Lyons et al. |
| 2009/0264813 A1 | 10/2009 | Chang |
| 2010/0311808 A1 | 12/2010 | Lyons et al. |
| 2010/0317586 A1 | 12/2010 | Babizhayev |
| 2011/0034448 A1 | 2/2011 | Chang et al. |
| 2011/0046536 A1 | 2/2011 | Stegmann et al. |
| 2011/0172206 A1 | 7/2011 | Zack et al. |
| 2011/0238075 A1 | 9/2011 | Clauson et al. |
| 2011/0274744 A1 | 11/2011 | Picart et al. |
| 2012/0078362 A1 | 3/2012 | Haffner et al. |
| 2012/0141573 A1 | 6/2012 | Ling et al. |
| 2012/0197175 A1 | 8/2012 | Horvath et al. |
| 2012/0226133 A1 | 9/2012 | Wong et al. |
| 2012/0310137 A1 | 12/2012 | Silvestrini |
| 2013/0017243 A1 | 1/2013 | Shi et al. |
| 2013/0281908 A1 | 10/2013 | Schaller et al. |
| 2013/0289467 A1 | 10/2013 | Haffner et al. |
| 2014/0018771 A1 | 1/2014 | Shekalim |
| 2014/0031408 A1 | 1/2014 | Edelman et al. |
| 2014/0086974 A1 | 3/2014 | Wu et al. |
| 2014/0121209 A1 | 5/2014 | Pujara |
| 2014/0121584 A1 | 5/2014 | Wardle et al. |
| 2014/0236066 A1 | 8/2014 | Horvath et al. |
| 2014/0323995 A1 | 10/2014 | Clauson et al. |
| 2014/0371651 A1 | 12/2014 | Pinchuk |

| | | |
|---|---|---|
| 2015/0051699 A1 | 2/2015 | Badawi et al. |
| 2015/0182670 A1 | 7/2015 | Rizk et al. |
| 2015/0238687 A1 | 8/2015 | Novakovic et al. |
| 2015/0258061 A1 | 9/2015 | Zack et al. |
| 2015/0320596 A1 | 11/2015 | Gifford, III et al. |
| 2016/0199297 A1 | 7/2016 | Edelman et al. |
| 2016/0206556 A1 | 7/2016 | Venkatraman et al. |
| 2017/0000730 A1 | 1/2017 | Peyman |
| 2017/0065610 A1 | 3/2017 | Pujara |
| 2017/0095369 A1 | 4/2017 | Andino et al. |
| 2017/0172794 A1 | 6/2017 | Varner et al. |
| 2017/0202707 A1 | 7/2017 | Badawi et al. |
| 2017/0239272 A1 | 8/2017 | Ambati et al. |
| 2017/0266200 A1 | 9/2017 | Sheetrit et al. |
| 2018/0001581 A1 | 1/2018 | Patel et al. |
| 2018/0028361 A1 | 2/2018 | Haffner et al. |
| 2018/0085307 A1 | 3/2018 | Sawhney et al. |
| 2018/0243131 A1 | 8/2018 | Erickson et al. |
| 2018/0250311 A1 | 9/2018 | Ambati et al. |
| 2018/0263817 A1 | 9/2018 | Roeber et al. |
| 2018/0264179 A1 | 9/2018 | Pan et al. |
| 2018/0271781 A1 | 9/2018 | Ni |
| 2018/0280194 A1 | 10/2018 | Heitzmann et al. |
| 2018/0303665 A1 | 10/2018 | Heitzmann et al. |
| 2018/0333296 A1 | 11/2018 | Heitzmann et al. |
| 2019/0038551 A1 | 2/2019 | Edelman et al. |
| 2019/0110984 A1 | 4/2019 | Ni |
| 2019/0125581 A1 | 5/2019 | Heitzmann et al. |
| 2019/0375149 A1 | 12/2019 | Limem et al. |
| 2020/0038238 A1 | 2/2020 | Kuzma et al. |
| 2020/0069847 A1 | 3/2020 | Robinson et al. |
| 2020/0121503 A1 | 4/2020 | Badawi et al. |
| 2020/0171100 A1 | 6/2020 | Krueger et al. |
| 2020/0276111 A1 | 9/2020 | Bley et al. |
| 2020/0289534 A1 | 9/2020 | Peyman |
| 2020/0297530 A1 | 9/2020 | Cohen et al. |
| 2020/0345896 A1 | 11/2020 | Peyman |
| 2020/0375889 A1 | 12/2020 | Hughes et al. |
| 2021/0030766 A1 | 2/2021 | Ghebremeskel et al. |
| 2021/0121397 A1 | 4/2021 | Edelman et al. |
| 2021/0196729 A1 | 7/2021 | Hughes |
| 2021/0251893 A1 | 8/2021 | Blizzard et al. |
| 2021/0308042 A1 | 10/2021 | Ni |
| 2021/0386584 A1 | 12/2021 | Badawi et al. |
| 2022/0000663 A1 | 1/2022 | Haffner et al. |
| 2022/0023095 A1 | 1/2022 | Ghebremeskel et al. |
| 2022/0104967 A1 | 4/2022 | Badawi et al. |
| 2022/0160668 A1 | 5/2022 | Badawi et al. |
| 2022/0168142 A1 | 6/2022 | Saim et al. |
| 2022/0168146 A1 | 6/2022 | Badawi et al. |
| 2022/0168229 A1 | 6/2022 | Kang-Mieler et al. |
| 2022/0218643 A1 | 7/2022 | Blizzard et al. |
| 2022/0313486 A1 | 10/2022 | Heitzmann et al. |
| 2022/0331335 A1 | 10/2022 | Reich et al. |
| 2022/0354695 A1 | 11/2022 | Badawi et al. |
| 2022/0378612 A1 | 12/2022 | Badawi et al. |
| 2023/0218508 A1 | 7/2023 | Thakur et al. |
| 2023/0285281 A1 | 9/2023 | Blizzard et al. |
| 2023/0285282 A1 | 9/2023 | Blizzard et al. |
| 2023/0293347 A1 | 9/2023 | Badawi et al. |
| 2023/0301830 A1 | 9/2023 | Heitzmann et al. |
| 2024/0173251 A1 | 5/2024 | Badawi et al. |
| 2024/0225894 A1 | 7/2024 | Needleman et al. |
| 2024/0350314 A1 | 10/2024 | Badawi et al. |
| 2024/0366424 A1 | 11/2024 | Badawi et al. |
| 2024/0415860 A1 | 12/2024 | Badawi et al. |
| 2025/0221853 A1 | 7/2025 | Badawi et al. |
| 2025/0255750 A1 | 8/2025 | Badawi et al. |
| 2025/0268752 A1 | 8/2025 | O'Keeffe et al. |
| 2025/0302666 A1 | 10/2025 | Badawi et al. |
| 2025/0325401 A1 | 10/2025 | Needleman et al. |

FOREIGN PATENT DOCUMENTS

| | | |
|---|---|---|
| JP | 2002-541976 A | 12/2002 |
| JP | 2003-180730 A | 7/2003 |
| JP | 2005-510317 A | 4/2005 |
| JP | 2005-538809 A | 12/2005 |
| WO | WO-94/13234 A1 | 6/1994 |

(56) References Cited

FOREIGN PATENT DOCUMENTS

| WO | WO-97/11655 | A1 | 4/1997 |
| WO | WO-00/64391 | A1 | 11/2000 |
| WO | WO-00/64393 | A1 | 11/2000 |
| WO | WO-01/97727 | A1 | 12/2001 |
| WO | WO-02/36052 | A1 | 5/2002 |
| WO | WO-03/082139 | A1 | 10/2003 |
| WO | WO-2004/000223 | A2 | 12/2003 |
| WO | WO-2005/016418 | A1 | 2/2005 |
| WO | WO-2005/105197 | A2 | 11/2005 |
| WO | WO-2005/105197 | A3 | 11/2005 |
| WO | WO-2005/107664 | A2 | 11/2005 |
| WO | WO-2005/107664 | A3 | 11/2005 |
| WO | WO-2005/110380 | A1 | 11/2005 |
| WO | WO-2005/117752 | A1 | 12/2005 |
| WO | WO-2006/057859 | A1 | 6/2006 |
| WO | WO-2006/066103 | A2 | 6/2006 |
| WO | WO-2006/066103 | A3 | 6/2006 |
| WO | WO-2006/122165 | A2 | 11/2006 |
| WO | WO-2006/122165 | A3 | 11/2006 |
| WO | WO-2007/084582 | A2 | 7/2007 |
| WO | WO-2008/002377 | A1 | 1/2008 |
| WO | WO-2009/042596 | A2 | 4/2009 |
| WO | WO-2009/042596 | A3 | 4/2009 |
| WO | WO-2009/126569 | A1 | 10/2009 |
| WO | WO-2010/078063 | A1 | 7/2010 |
| WO | WO-2010/135369 | A1 | 11/2010 |
| WO | WO-2011/075481 | A1 | 6/2011 |
| WO | WO-2011/084366 | A2 | 7/2011 |
| WO | WO-2011/084366 | A3 | 7/2011 |
| WO | WO-2011/127064 | A2 | 10/2011 |
| WO | WO-2011/127064 | A3 | 10/2011 |
| WO | WO-2012/071476 | A2 | 5/2012 |
| WO | WO-2012/071476 | A3 | 5/2012 |
| WO | WO-2012/075184 | A2 | 6/2012 |
| WO | WO-2012/075184 | A3 | 6/2012 |
| WO | WO-2012/134528 | A1 | 10/2012 |
| WO | WO-2014/066653 | A1 | 5/2014 |
| WO | WO-2014/130574 | A1 | 8/2014 |
| WO | WO-2015/073571 | A1 | 5/2015 |
| WO | WO-2015/100120 | A1 | 7/2015 |
| WO | WO-2016/115369 | A1 | 7/2016 |
| WO | WO-2017/015604 | A1 | 1/2017 |
| WO | WO-2017/015675 | A1 | 1/2017 |
| WO | WO-2017/040853 | A1 | 3/2017 |
| WO | WO-2017/087902 | A1 | 5/2017 |
| WO | WO-2017184881 | A1 * | 10/2017 ........... A61K 9/0051 |
| WO | WO-2018/058048 | A1 | 3/2018 |
| WO | WO-2018/064648 | A1 | 4/2018 |
| WO | WO-2018/175340 | A1 | 9/2018 |
| WO | WO-2019/018424 | A1 | 1/2019 |
| WO | WO-2019/094702 | A1 | 5/2019 |
| WO | WO-2019/170752 | A1 | 9/2019 |
| WO | WO-2020/028022 | A1 | 2/2020 |
| WO | WO-2020/046299 | A1 | 3/2020 |
| WO | WO-2020/243608 | A1 | 12/2020 |
| WO | WO-2021/087399 | A1 | 5/2021 |
| WO | WO-2021/158968 | A1 | 8/2021 |
| WO | WO-2021/231977 | A1 | 11/2021 |
| WO | WO-2021/255264 | A1 | 12/2021 |
| WO | WO-2022/056392 | A1 | 3/2022 |
| WO | WO-2022/251477 | A1 | 12/2022 |
| WO | WO-2023/107478 | A1 | 6/2023 |

OTHER PUBLICATIONS

Corrected Notice of Allowability mailed on Apr. 25, 2016, U.S. Appl. No. 13/025,112, filed Feb. 10, 2011, 2 pages.
Corrected Notice of Allowability mailed on Sep. 1, 2016, for U.S. Appl. No. 13/445,816, filed Apr. 12, 2012, 2 pages.
Corrected Notice of Allowability mailed on Oct. 12, 2021, for U.S. Appl. No. 16/532,260, filed Aug. 5, 2019, 2 pages.
Extended European Search Report mailed Apr. 22, 2015, for EP Patent Application No. 11 740 372.5, filed Feb. 3, 2011, six pages.

Extended European Search Report mailed on May 17, 2011, for European Patent Application No. 11 162 487.0, filed on May 31, 2007, 6 pages.
Final Office Action mailed on Nov. 1, 2010, for U.S. Appl. No. 11/475,523, filed Jun. 26, 2006, 12 pages.
Final Office Action mailed on Jul. 19, 2012, for U.S. Appl. No. 13/245,811, filed Sep. 26, 2011, 6 pages.
Final Office Action mailed on Feb. 1, 2013, for U.S. Appl. No. 13/020,706, filed Feb. 3, 2011, 6 pages.
Final Office Action mailed on Sep. 15, 2014, for U.S. Appl. No. 13/025,112, filed Feb. 10, 2011, 13 pages.
Final Office Action mailed on Apr. 23, 2015, for U.S. Appl. No. 14/527,292, filed Oct. 29, 2014, 8 pages.
Final Office Action mailed on Aug. 19, 2015, for U.S. Appl. No. 13/445,816, filed Apr. 12, 2012, 6 pages.
Final Office Action mailed on Apr. 6, 2018, for U.S. Appl. No. 15/683,652, filed Aug. 22, 2017, 11 pages.
Final Office Action mailed on Oct. 19, 2018, for U.S. Appl. No. 15/683,652, filed Aug. 22, 2017, 8 pages.
Final Office Action mailed on Apr. 1, 2021, for U.S. Appl. No. 16/532,260, filed Aug. 5, 2019, 8 pages.
International Search Report mailed on Nov. 30, 2007, for PCT Application No. PCT/US2007/013038, filed on May 31, 2007, 4 pages.
International Search Report mailed on Apr. 5, 2011, for PCT Application No. PCT/US2011/023643, filed on Feb. 3, 2011, 2 pages.
Ma, A.K. et al. (2020). "GlaucoMap—Distribution of glaucoma surgical procedures in the United States," Clin. Ophthalmol. 14:2551-2560.
Non-Final Office Action mailed on May 17, 2010, for U.S. Appl. No. 11/475,523, filed Jun. 26, 2006, 10 pages.
Non-Final Office Action mailed on Jan. 26, 2012, for U.S. Appl. No. 12/695,053, filed Jan. 27, 2010, 10 pages.
Non-Final Office Action mailed on Mar. 15, 2012, for U.S. Appl. No. 13/245,811, filed Sep. 26, 2011, 4 pages.
Non-Final Office Action mailed on May 11, 2012, for U.S. Appl. No. 13/020,706, filed Feb. 3, 2011, 5 pages.
Non-Final Office Action mailed on Nov. 9, 2012, for U.S. Appl. No. 13/245,811, filed Sep. 26, 2011, 5 pages.
Non-Final Office Action mailed on Feb. 24, 2014, for U.S. Appl. No. 13/025,112, filed Feb. 10, 2011, 12 pages.
Non-Final Office Action mailed on Feb. 4, 2015, for U.S. Appl. No. 13/445,816, filed Apr. 12, 2012, 6 pages.
Non-Final Office Action mailed on Feb. 23, 2015, for U.S. Patent Application No. 13/025, 112, filed on Feb. 10, 2011, 17 pages.
Non-Final Office Action mailed on Jul. 10, 2015, for U.S. Appl. No. 13/025,112, filed Feb. 10, 2011, 16 pages.
Non-Final Office Action mailed on Oct. 7, 2015, U.S. for U.S. Appl. No. 14/527,292, filed Oct. 29, 2014, 5 pages.
Non-Final Office Action mailed on Dec. 14, 2015, for U.S. Appl. No. 13/445,816, filed Apr. 12, 2012, 7 pages.
Non-Final Office Action mailed on Jun. 7, 2016, for U.S. Appl. No. 14/527,292, filed Oct. 29, 2014, 5 pages.
Non-Final Office Action mailed on Dec. 15, 2017, for U.S. Appl. No. 15/343,147, filed Nov. 3, 2016, 12 pages.
Non-Final Office Action mailed on Aug. 9, 2018, for U.S. Appl. No. 15/182,165, filed Jun. 14, 2016, 9 pages.
Non-Final Office Action mailed on Sep. 20, 2018, for U.S. Appl. No. 15/340,911, filed Nov. 1, 2016, 7 pages.
Non-Final Office Action mailed on Apr. 26, 2022, for U.S. Appl. No. 16/413,466, filed May 15, 2019, 8 pages.
Non-Final Office Action mailed on Jul. 27, 2022, for U.S. Appl. No. 16/526,832, filed Jul. 30, 2019, 8 pages.
Notice of Allowance mailed on Feb. 2, 2011, for U.S. Appl. No. 11/475,523, filed Jun. 26, 2006, 6 pages.
Notice of Allowance mailed on Jun. 11, 2012, for U.S. Appl. No. 12/695,053, filed Jan. 27, 2010, 7 pages.
Notice of Allowance mailed on Apr. 2, 2013, for U.S. Appl. No. 13/245,811, filed Sep. 26, 2011, 6 pages.
Notice of Allowance mailed on May 10, 2013, for U.S. Appl. No. 13/020,706, filed Feb. 3, 2011, 8 pages.

(56)          References Cited

OTHER PUBLICATIONS

Notice of Allowance mailed on Jul. 7, 2014, for U.S. Appl. No. 14/012,963, filed Aug. 28, 2013, 6 pages.
Notice of Allowance mailed on Mar. 1, 2016, for U.S. Appl. No. 13/025,112, filed Feb. 10, 2011, 7 pages.
Notice of Allowance mailed on Jul. 13, 2016, for U.S. Appl. No. 13/445,816, filed Apr. 12, 2012, 7 pages.
Notice of Allowance mailed on Feb. 6, 2019, for U.S. Appl. No. 15/182,165, filed Jun. 14, 2016, 6 pages.
Notice of Allowance mailed on Apr. 15, 2019, for U.S. Appl. No. 15/683,652, filed Aug. 22, 2017, 5 pages.
Notice of Allowance mailed on Apr. 23, 2019, for U.S. Appl. No. 15/340,911, filed Nov. 1, 2016, 5 pages.
Notice of Allowance mailed on Sep. 17, 2021, for U.S. Appl. No. 16/532,260, filed Aug. 5, 2019, 9 pages.
Notice of Allowance mailed on Jun. 8, 2022, for U.S. Appl. No. 16/413,466, filed May 15, 2019, 5 pages.
Quigley, H.A. et al. (2006). "The number of people with glaucoma worldwide in 2010 and 2020," Br. J. Ophthalmol. 90:262-267.
Shaikh, Y. et al. (2014). "Burden of undetected and untreated glaucoma in the United States," Am. J. Ophthalmol. 158:1121-1129.
Tham, Y-C. et al. (2014). "Global prevalence of Glaucoma and Projections of Glaucoma Burden throuh 2040," Ophthalmology 121:2081-2090.
Thorleifsson, G. et al. (2010). "Common variants near CAV1 and CAV2 are associated with primary open-angle glaucoma," Nat. Genet. 42:906-909.
Tielsch, J.M. et al. (1991). "Racial variations in the prevalence of primary open-angle glaucoma," JAMA 266:369-374.
Varma, R. et al. (2004). "Prevalence of open-angle glaucoma and ocular hypertension in Latinos—The Los Angeles Latino Eye Study," Ophthalmology 111:1439-1448.
Wiggs, J.L. et al. (2012). "Common variants at 9p21 and 8q22 are associated with increased susceptibility to optic nerve degeneration in glaucoma," PLoS Genet. 8:e1002654.
Wolfs, R.C.W. et al. (1998). "Genetic risk of primary open-angle glaucoma," Arch. Ophthalmol. 116:1640-1645.
Wormald, R.P.L. et al. (1994). "The African Caribbean eye survey: risk factors for glaucoma in a sample of African Caribbean people living in London," Eye 8(pt. 3):315-320.
Written Opinion mailed on Nov. 30, 2007, for PCT Application No. PCT/US2007/013038, filed on May 31, 2007, 6 pages.
Written Opinion mailed on Apr. 5, 2011, for PCT Application No. PCT/US2011/023643, filed on Feb. 3, 2011, 5 pages.
Ahn, W. et al. (2002). "The "Gauge" System for the Medical Use," Anesth. Analg. 95:1125, with Table 1.
Aragona, P. et al. (2002). "Long Term Treatment with Sodium Hyaluronate-Containing Artificial Tears Reduces Ocular Surface Damage in Patients with Dry Eye," Br. J. Ophthalmol. 86:181-184.
Arestin® (2022). Tips for Use, Bausch Health Companies, Inc., 1 total page.
Bahler, C.K. et al. (2004). "Trabecular bypass stents decrease intraocular pressure in cultured human anterior segments," Am. J. Ophthalmol. 138:988-994.
Balazs, E.A. et al. (1972). "Hyaluronic Acid and Replacement of Vitreous and Aqueous Humor," Modern Problems in Ophthalmology 10:3-21.
Bertram, J.P. et al. (2022). "Sustained delivery of timolol maleate from poly(lactic-co-glycolic acid)/poly(lactic acid) microspheres for over 3 months," J. Microoencapsul. 26:18-26.
Butany, J. et al. (2005). "Coronary artery stents; identification and evaluation," J. Clin. Pathol. 58:795-804.
Chae, J.J. et al. (2021). "Drug-Free, Nonsurgical Reduction of Intraocular Pressure for Four Months after Suprachoroidal Injection of Hyaluronic Acid Hydrogel," Adv. Sci. 8:2001908, 12 total pages.
Chhadva, P. et al. (2017). "Meibomian gland disease: The role of gland dysfunction in dry eye disease," Ophthalmol. 124(11 suppl):S20-S26.

clinicaltrials.gov (2006). A study of the trabecular micro-bypass stent in combination with cataract surgery in subjects with open angle glaucoma, NCT00323284, 6 total pages.
Colombo, A. et al. (2002). "Selection of coronary stents," J. Am. Coll. Cardiol. 40:1021-1033.
Drusedau, M.U.H. et al. (2000). "Viscocanalostomy for primary open-angle glaucoma: The gross Pankow experience," J. Cataract Refract. Surg. 26:1367-1373.
EP Application No. 22 812 314.7, Extended European Search Report mailed Dec. 2, 2024, Sight Sciences, Inc., 8 pages.
Glaukos iStent (2022). iStent inject® W, 9 total pages.
Guerrero, A.H. et al. (2000). "Complications of glaucoma drainage implant surgery," Int. Ophthalmol. Clin. 40:149-163.
PCT Application No. PCT/US2022/031457, International Search Report and Written Opinion mailed Nov. 2, 2022, Sight Sciences, Inc., 15 pages.
PCT Application No. PCT/US2023/081471, International Search Report and Written Opinion mailed Apr. 30, 2024, Sight Sciences, Inc., 11 pages.
PCT Application No. PCT/IB2025/055574, International Search Report and Written Opinion mailed Sep. 17, 2025, Sight Sciences, Inc., 15 pages.
Jacob, J.S. (1985). "Corneal thickness changes following cataract surgery: effect of lens implantation and sodium hyaluronate," British Journal of Ophthalmology 69:567-571.
Jung, H.J. et al. (2013). "Extended release of timolol from nanoparticle-loaded fornix insert for glaucoma therapy," J. Ocul. Pharmacol. Ther. 29:229-235.
Lavik, E. et al. (2016). "Sustained Delivery of Timolol Maleate for Over 90 Days by Subconjunctival Injection," J. Ocul. Pharmacol. Ther. 32:642-649.
Lemp, M.A. et al. (2012). "Distribution of aqueous-deficient and evaporative dry eye in a clinic-based patient cohort: a retrospective study," Cornea 472-478.
Johnson, D.H. et al. (2001). "How does nonpenetrating glaucoma surgery work? Aqueous outflow resistance and glaucoma surgery." J. Glaucoma 10:55-67.
Medline Plus (Feb. 15, 2016). "Dorzolamide and Timolol Ophthalmic," located at https://medlineplus.gov/druginfo/meds/a602022.html, 5 pages.
Minckler, D. et al. (2006). "Aqueous shunts for glaucoma (review," Cochrane Library, 47 total pages.
Myers, T.D. et al. (1999). "Comparison of the Effects of Viscoelastic Agents on Clinical Properties of the Unfolder Lens Injection System," Journal of Cataract and Refractive Surgery 25:953-958.
Nelson, J.D. et al. (2017). "TFOS DEWS II Introduction," Ocul. Surf. 15:269-275.
Nesterov, A.P. (1970). "Role of Blockage of Schlemm's Canal in Pathogenesis of Primary Open-Angle Glaucoma," Am. J. Ophthalmol. 70:691-696.
U.S. Appl. No. 16/943,644, Non-Final Office Action mailed May 10, 2024, Inventor Badawi, David Y. et al., 10 pages.
U.S. Appl. No. 16/943,644, Non-Final Office Action mailed Mar. 19, 2025, Inventor Badawi, David Y. et al., 12 pages.
U.S. Appl. No. 17/866,429, Non-Final Office Action mailed May 27, 2025, Inventor Badawi, David Y. et al., 9 pages.
Razeghinejad, M.R. et al. (2011). "A History of the Surgical Management of Glaucoma," Optom. Vis. Sci. 88:E39-E47.
Samuelson, T.W. (2011). "Randomized evaluation of the trabecular micro-bypass stent with phacoemulsification in patients with glaucoma and cataract," Ophthalmol. 118:459-467.
Schwartz, K.S. et al. (2006). "Glaucoma drainage implants: A critical comparison of types," Curr. Opin. Ophthalmol. 17:181-189.
Sidoti, P.A. et al. (1994). "Glaucoma drainage implants," Curr. Opin. Ophthalmol. 11:85-98.
Summary of Safety and Effectiveness Data, STAARVISCTM (sodium hyaluronate) Premarket Approval Application (PMA) No. P000046, Apr. 18, 2001, 11 total pages.
Stegmann, R. et al. (1999). "Viscocanalostomy for Open-Angle Glaucoma in Black African Patients," Journal of Cataract & Refractive Surgery 25:316-322.
Stegmann, R. (2002). Robert Stegmann, MD: taking on the challenges of ocular trauma and disease, Ocular Surgery News, located

(56) References Cited

OTHER PUBLICATIONS at https://www.healio.com/news/ophthalmology/20120331/robert-stegmann-md-taking-on-the-challenges-of-ocular-trauma-and-disease, 4 total pages.

Stefansson, J. (1925). "American journal of ophthalmology," vol. 8, pp. 681-693.

Wild, G.J. et al. (2001). "Dilation of Schlemm's Canal in Viscocanalostomy: Comparison of 2 Viscoelastic Substances," Journal of Cataract and Refractive Surgery 27:1294-1297.

Yablonski, M.E. (2005). "Trabeculectomy with internal tube shunt—A novel glaucoma surgery," J. Glaucoma 14:91-97.

Zhou, J. et al. (2006). "Trabecular bypass—Effect of Schlemm canal and collector channel dilation," J. Glaucoma 15:446-455.

* cited by examiner

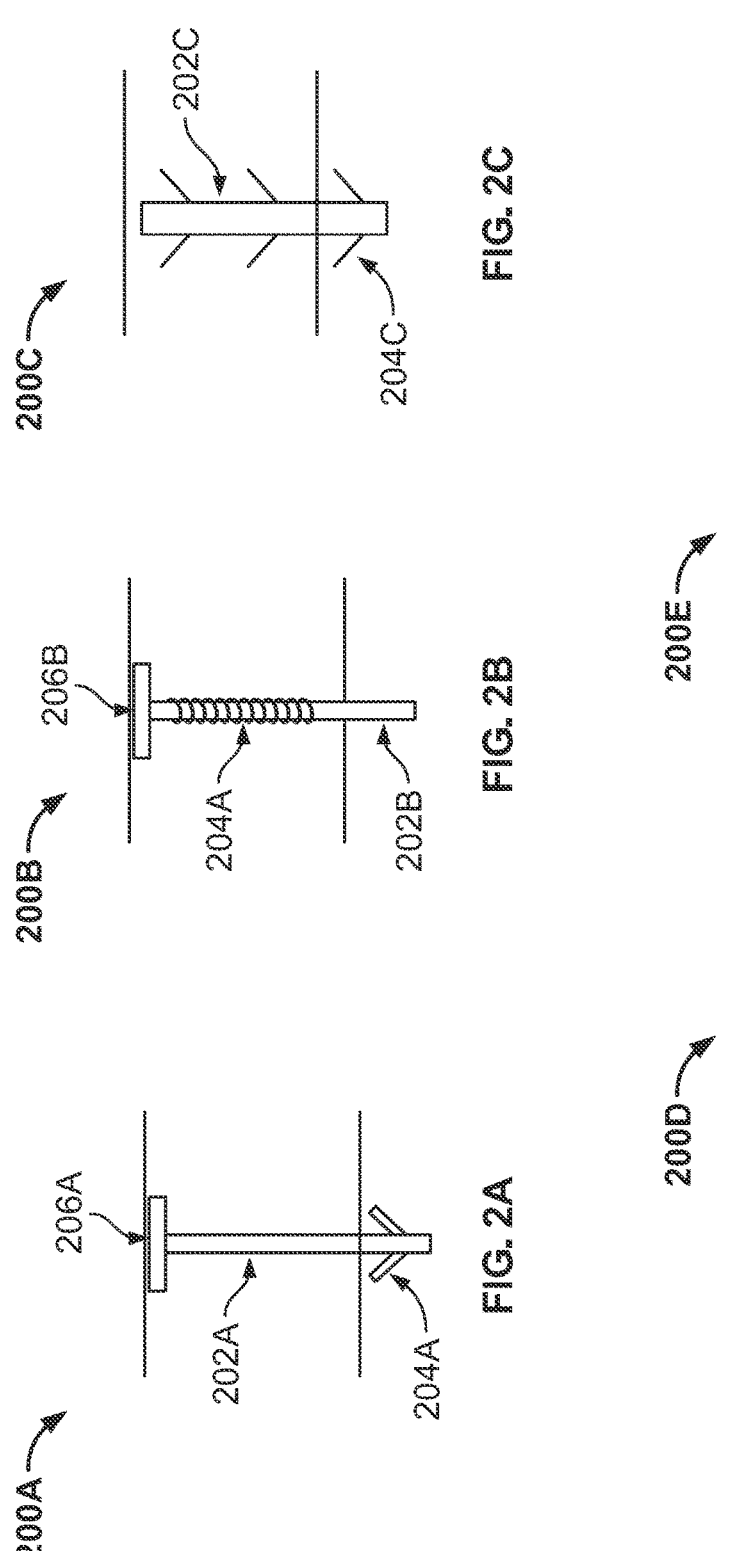
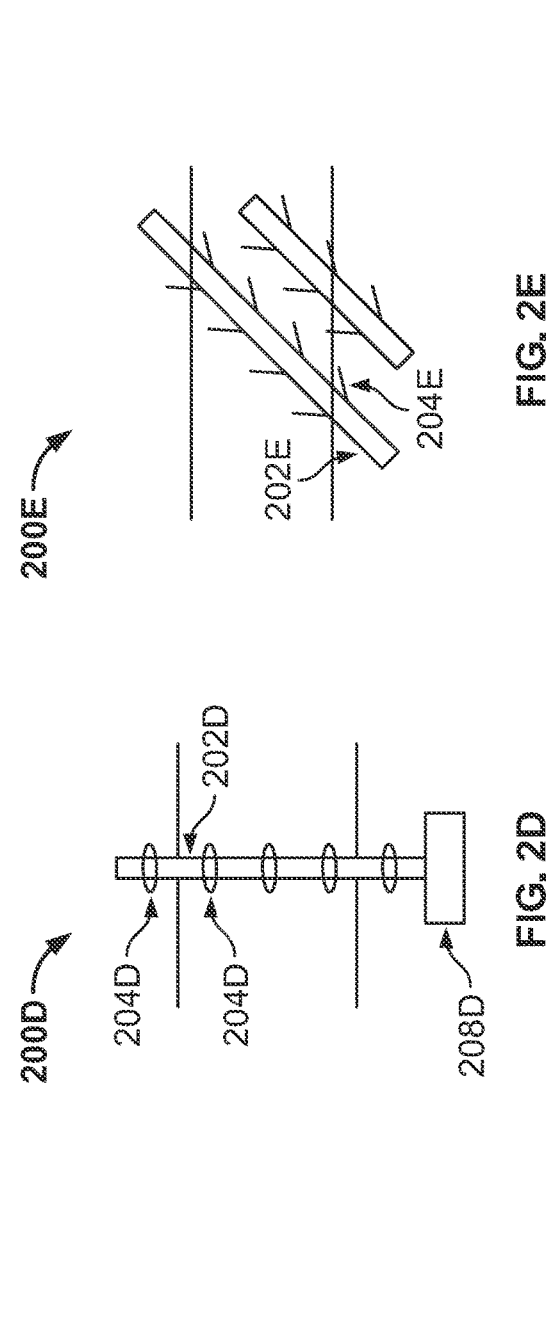
FIG. 2A
FIG. 2B
FIG. 2C
FIG. 2D
FIG. 2E

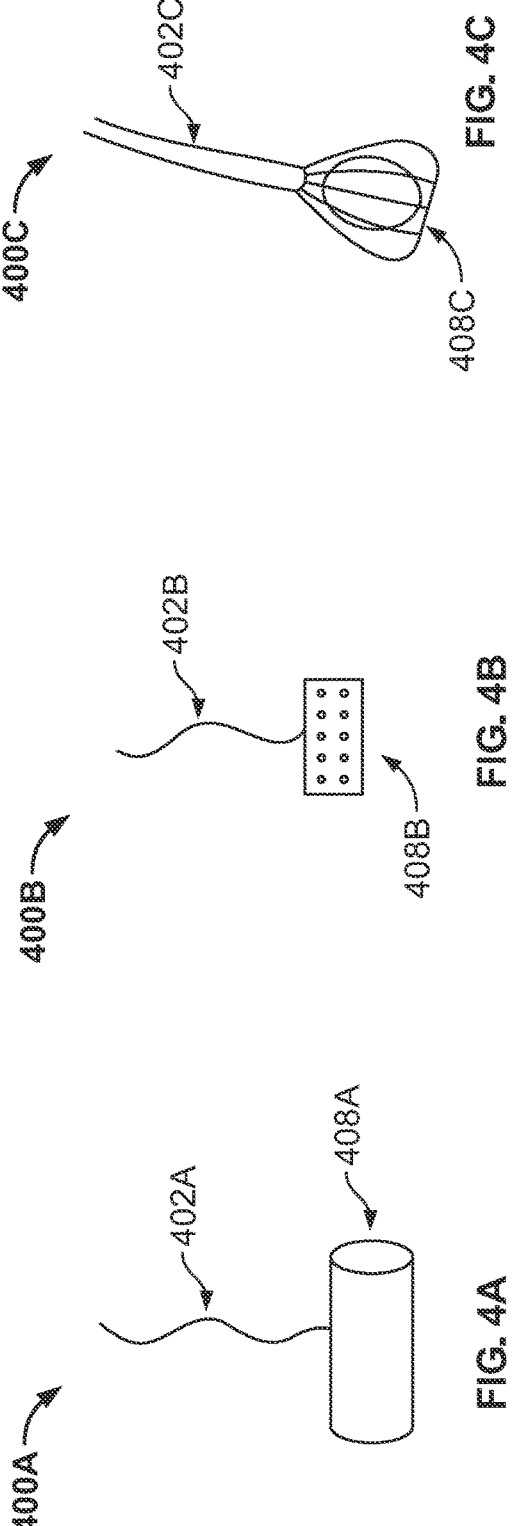
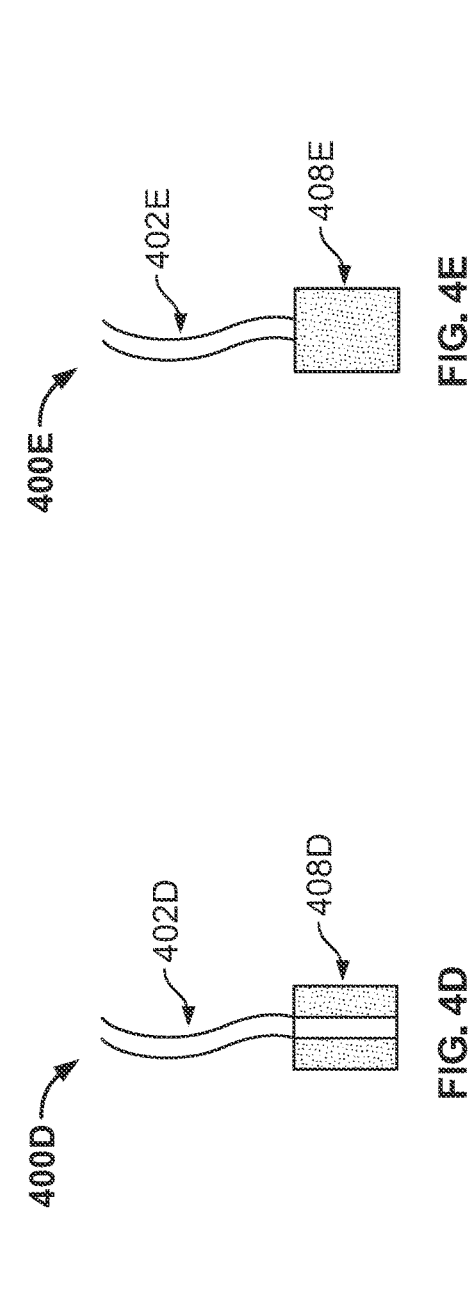
FIG. 4A
FIG. 4B
FIG. 4C
FIG. 4D
FIG. 4E

FIG. 5A
FIG. 5B
FIG. 5C
FIG. 5D
FIG. 5E
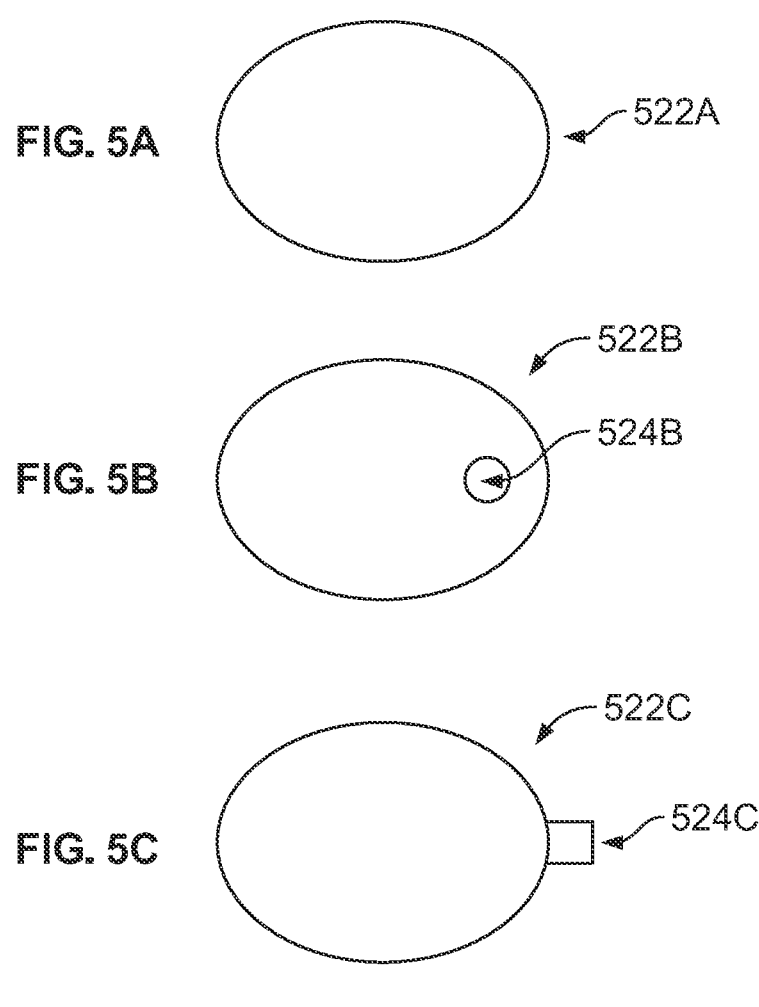
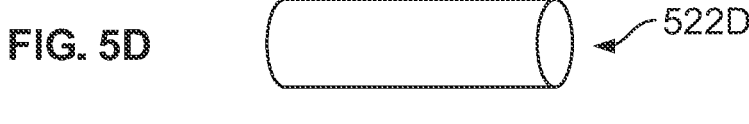
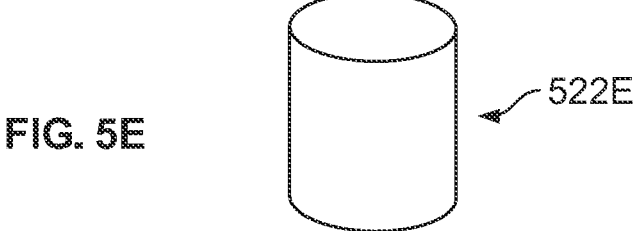

2002

2102

2202

INTRAOCULAR DEVICES, SYSTEMS, AND METHODS

CROSS-REFERENCE TO RELATED APPLICATIONS

This application claims the benefit of U.S. Provisional Application No. 63/194,824 filed May 28, 2021, the disclosure of which is hereby incorporated by reference in its entirety.

TECHNICAL FIELD

This invention relates generally to intraocular implants (e.g., drug-eluting implants) for treating conditions of the eye, and associated methods and systems for treating such conditions of the eye.

BACKGROUND

Glaucoma is a group of optic neuropathies associated with specific structural changes to the optic nerve ultimately leading to irreversible visual field loss. In many cases, this loss of vision is progressive and leads to blindness if untreated. According to the National Eye Institute at the United States National Institutes of Health, glaucoma is the leading cause of irreversible blindness worldwide. In 2020, approximately three million people in the United States carry a diagnosis of glaucoma. Worldwide, that number is 80 million people. By 2040, it is expected that over 110 million people will be living with this potentially blinding condition ("Global Prevalence of Glaucoma and Projections of Glaucoma Burden through 2040", Ophthalmology 2014; 121: 2081-2090). Glaucoma generally falls into two categories: open angle glaucoma and closed angle glaucoma. Open angle glaucoma is approximately seven times more common than the closed angle form in both the U.S. and Europe (Quigley H A, Broman A T. Br. J. Ophthalmol. 2006; 90(3):262-267). The course of both forms of the disease is, typically, a chronic and progressive loss of vision, leading to constriction of the visual field. The ultimate result is permanent blindness. Because it is typically asymptomatic until the disease is significantly advanced, early diagnosis through regular eye exams and early treatment are critical. While the prevalence of glaucoma increases with age, the majority of patients with undiagnosed glaucoma are under 60 years of age (Shaikh Y, Yu F, Coleman A L. Am. J. Ophthalmol. 2014; 158(6):1121-1129).

Risk factors associated with glaucoma include family history, ethnic origin, and age. Having a first degree relative with glaucoma is associated with a significantly increased risk (Wolfs R C, Klaver C C, Ramrattan R S, van Duijn C M, Hofman A, de Jong P T. Arch Ophthalmol. 1998; 116(12):1640-1645). Black and Hispanic individuals have increased prevalence of open angle glaucoma. Additionally, they are often diagnosed with more severe disease. Asian, Southeast Asian, Asian Indian, and Inuit individuals are more often diagnosed with closed angle glaucoma (see e.g., Varma R, Ying-Lai M, Francis B A, et al.; Los Angeles Latino Eye Study Group. Ophthalmology 2004; 111(8): 1439-1448; Tielsch J M, Sommer A, Katz J, Royall R M, Quigley H A, Javitt J. JAMA. 1991; 266(3):369-374; Wormald R P, Basauri E, Wright L A, Evans J R. Eye (Loud). 1994; 8(Pt 3):315-320; and Arkell S M, Lightman D A, Sommer A, Taylor H R, Korshin O M, Tielsch J M. Arch. Ophthalmol. 1987; 105(4):482-485).

Closed angle glaucoma typically results from anatomic obstruction of the anterior chamber angle and its associated drainage channels. The anatomic obstruction prevents aqueous humor from efficiently reaching the drainage channels thereby resulting in increased intraocular pressure. Surgical iridectomy, laser iridotomy, or lensectomy are often considered more definitive surgical options versus more palliative medical therapy such as cholinergic drugs (e.g., pilocarpine eyedrops) to relive obstruction by pupil constriction.

Open angle glaucoma (OAG) is much more common in the U.S., and it accounts for significantly more loss of vision that its closed counterpart. While the exact pathophysiology of OAG is not completely understood, it has been demonstrated that increased intraocular pressure (IOP) correlates with retinal ganglion cell death. There is a relationship between secretion of aqueous humor by the ciliary body and its egress from the eye via conventional trabecular meshwork pathways and the unconventional uveoscleral pathway. This relationship and any resultant imbalances determine IOP. It is felt that an increased resistance to outflow in the trabecular meshwork or more distal aqueous collector channels are associated with increased IOP in OAG. Increased IOP may cause mechanical stress on the lamina cribrosa, where retinal ganglion cell axons exit the eye to coalesce into the optic nerve. IOP-induced stress at the lamina cribrosa can deform, damage, and interfere with the retinal axons leading to irreversible injury and vision loss. While such IOP associated damage typically occurs when the pressure is above the population average pressures, it can occur at lower or "normal" pressure depending on an individual's vulnerability. Conversely, many people with higher-than-average IOP never develop glaucoma. A growing number of studies are identifying genomic loci associated with glaucoma susceptibility. Thus, glaucoma may develop in patients with an intraocular pressure relatively high for their individual susceptibility (see e.g., Thorleifsson G, Walters G B, Hewitt A W, et al. Nat Genet. 2010; 42(10):906-909; and Wiggs J L, Yaspan B L, Hauser M A, et al. PLoS Genet. 2012; 8(4):e1002654). When ganglion cell death does occur in glaucoma, characteristic changes in the optic nerve head and the nerve fiber layer become evident. This eventually is associated with characteristic visual field loss patterns. Prompt referral to an eye care specialist is critical to treat the glaucoma and slow the progression of irreversible damage and subsequent loss of vision. There is no single gold standard test for diagnosing glaucoma. Typically, several criteria are taken into consideration in making the diagnosis of glaucoma. These include age, family history, ethnic background, IOP, corneal thickness, optical coherence tomographic analysis of various retinal tissues, optic nerve head appearance, and peripheral visual field testing.

The primary goal of treatment is to slow progressive optic nerve damage in order to preserve vision and quality of life. Early diagnosis and intervention are critical given that visual loss is irreversible. Reduction of IOP with treatment combined with continuous diagnostic assessments of treatment efficacy are part of the mainstay of glaucoma care.

Initially, treatment is typically comprised of the least number of medications required to adequately reduce IOP. Medications include drugs from the following families of compounds: prostaglandins, beta-adrenergic blockers, alpha-adrenergic agonists, carbonic anhydrase inhibitors, Rho-kinase (ROCK) inhibitors, and cholinergic drugs.

Should medical therapy fail, not be tolerated, or not be possible, other forms of therapy may be added or substitute to medical therapy. For example, laser therapy to the eye in the form of trabeculoplasty, cycloablation (endoscopic or transscleral) may be performed. In more advanced cases or under some circumstances, incisional surgery can be considered. Trabeculectomy, valves, or shunts can be used to help control IOP. Recently, minimally invasive glaucoma surgery or MIGS has become a popular surgical approach to the treatment of glaucoma. Various technologies are being employed to reduce IOP while reducing exposure to surgical risks posed by more invasive treatments like trabeculectomy or valve placement. In 2017, nearly 175,000 surgical procedures were performed. The surgeries included over 20,000 trabeculectomies, 20,000 glaucoma drainage implants, and over 130,000 MIGS procedures (Ma A K, Lee J H, Warren J L, Teng C C. *Clin Ophthalmol.* 2020; 14:2551-2560).

While medical therapy is the preferred initial treatment of OAG in the U.S., it does have many problems. Drops can be cost prohibitive for patients, and patients can forget to regularly use them. Additionally, proper instillation into the conjunctival cul-de-sac may be more difficult, especially in the hands of the elderly or arthritic. Excessive instillation, such as instilling multiple drops, and subsequent wasting of medication is also an issue. However, even with proper instillation of the eyedrops, medication is wasted. For instance, a typical eyedrop may be 60-90 microliters, but the ocular surface can typically hold no more than 10 microliters. The therapeutic ingredients and the preservatives with which they are often combined can lead to ocular surface disease, discomfort, inflammation, dry eye, and reduced corneal sensitivity, all of which can irritate the eye and further reduce compliance. Multiple eyedrop medications can also lead to confusion and misuse of the medications. All of these factors combine to create problems with the mainstay of glaucoma therapy-drugs. However, medications do avoid a lot of the more serious complications that can occur with surgery.

Surgical therapy of glaucoma is typically reserved as a second line therapy in the U.S. That is gradually changing with microinvasive glaucoma surgery (MIGS) becoming more mainstream. Nonetheless, glaucoma surgery carries its own risks. One of the more problematic complications is bacterial endophthalmitis, which is a potentially visually devastating ocular infection. However, there are many other complications of glaucoma surgery, including failure, hypotony, hemorrhage, malignant glaucoma, progression, hyphema, retinal detachment, and many others. Moreover, there are long term complications with trabeculectomy plus antimetabolite and glaucoma drainage devices.

While glaucoma has been covered in more detail here, many other ocular diseases are being successfully treated with drugs. In addition to being used to medically treat various ocular diseases, drugs are also often used as an adjunct in the surgical treatment of ocular diseases. They are used to treat ocular surface disease, corneal disease, scleral disease, uveal disease, vitreous disease, and chorioretinal disease.

Age-related macular degeneration (AMD) is a common cause of vision loss in the U.S., and it is globally the third leading cause of blindness. It is associated with degeneration of the retinal pigment epithelium and Bruch's membrane. This itself can lead to overlying retinal damage and visual loss. Unlike the aforementioned "dry" degeneration, further degeneration and resulting in growth of neovascularization from the underlying choriocapillaris can lead to significant visual loss. This latter process is called "wet" macular degeneration. One of the more common forms of treatment is regular intravitreal injections of antibodies or drugs targeting vascular endothelial-derived growth factor (VEGF).

Patients often need to receive such injections with anti-VEGF drugs, typically antibody-derived therapeutics, including ranibizumab, aflibercept, or bevacizumab every 4-8 weeks to control their wet macular degeneration. There are significant issues with cost, complications, and associated morbidity with this mainstay of treatment.

Other retinal diseases require drug treatment, including macular edema, vascular occlusions, diabetic retinopathy, retinal degenerations, and retinal dystrophies. Uveal diseases can affect the choroid, ciliary body, and iris. Examples include iritis and other forms of uveitis which can respond well to various drugs such as steroids. Steroids are often given as oral treatments or as topical therapy. More aggressive cytotoxic agents and chemotherapy can be employed for more severe cases like Behcet's disease.

The vitreous can also be a location for ocular disease. It may harbor vision obstructing opacities or hemorrhage. In other instances, it may accumulate inflammatory cells in the setting of vitritis which can also lead to visual loss.

The lens in the eye is subject to a number of diseases. The most common are age related. Lens opacity or cataract often requires surgical correction in the form of cataract surgery. While many drugs have been used to slow cataract formation, none have so far proven to be significantly effective. After cataract surgery, a variety of drugs are often used to reduce likelihood of infection or inflammation.

The cornea can become opaque, scarred, or deformed because of diseases such as herpes zoster or simplex infection, keratitis, keratoconus, or other corneal degenerations. Additionally, transplanted corneas can suffer from immune mediated rejection.

Scleral disease can result from immune processes or infections. In fact, one of the most common ocular diseases is myopia or nearsightedness, and it is believed that the sclera plays a critical role in axial length and refractive state of the eye. Dilute topical atropine which may work by inducing cycloplegia, or paralysis of the ciliary body, has been shown to reduce development of axial myopia in children. Complex pathways likely account for the development of myopia in children. There is great interest in this area given the large percentage of the world's population that is affected.

Drugs can be administered for these, and other, ocular diseases in various ways. While there are systemic routes of administration such as oral or intravenous drug administration, the eye is particularly well suited to local administration because of its location on the surface of the body. Thus, local routes of drug administration are preferred in the majority of cases. This allows limited exposure of the rest of the body to drug and reduces the amount of drug needed. Currently, the most common route of drug administration for glaucoma is a topical eyedrop approach. Such topically administered drugs typically diffuse across the cornea and into the eye. For retinal diseases, drug injection is a common route.

Given the above-described difficulty in treating diseases such as, for example, glaucoma and age-related macular degeneration, there is a need for safer, more effective, and convenient treatments which address the shortcomings of the current standards of care.

SUMMARY

Intraocular implants for treating a condition of the eye and methods of their use are disclosed herein. In some variations, the intraocular implant comprises: an elongate implant body comprising a first end and a second end, wherein the elongate implant body is configured to be positioned at least partially in the sclera such that the first end of the elongate implant body is positioned in the sulcus or anterior chamber; at least one anchoring element coupled to or formed from the elongate implant body; and a drug, wherein the implant is configured to deliver the drug to the eye.

In some variations, the intraocular implant for treating a condition of the eye comprises an elongate implant body configured to be positioned intramurally in one or more of the sclera, the cornea, and the limbus; and a drug-eluting matrix configured to release a drug to the eye, wherein the drug-eluting matrix coats an exterior surface of the elongate implant body or is contained within an interior chamber of the elongate implant body.

In some variations, an intraocular implant comprises a spherical or rod-shaped implant body configured to be positioned entirely in the sclera; wherein the spherical or rod-shaped implant body comprises an erodible drug-eluting matrix.

In some variations, an intraocular implant comprises an implant body configured to be positioned partially or entirely in the limbus. The implant body may comprise an erodible drug-eluting matrix.

Also disclosed herein are methods of treating a condition in the eye of a subject. In some variations, the method comprises advancing a drug-eluting implant through the conjunctiva and the sclera of the eye of the subject; positioning a portion of the drug-eluting implant in the sclera and a first end of the implant in the sulcus; and delivering a drug from the drug-eluting implant to the sulcus of the subject to reduce a symptom of the condition of the eye.

Methods of treating a condition of the eye of a subject may also involve advancing a drug-eluting implant through the sclera of the eye and positioning the implant fully intramurally, with at least a portion in the limbus. In this way, a drug may be delivered to a tissue or structure of the eye, such as the anterior chamber, to reduce a symptom of the condition of the eye.

Also disclosed herein are methods of place a drug-eluting implant at least partially within the limbus of an eye of a subject. This placement may involve advancing the distal tip of a cannula containing the implant into an anterior chamber of the eye and retracting the cannula to release the implant at least partially within the limbus.

BRIEF DESCRIPTION OF THE DRAWINGS

FIGS. 2A-2J shows a variety of exemplary intraocular implants.

FIGS. 4A-4E show exemplary variations of housings of intraocular implants comprising a drug.

FIGS. 5A-5E show exemplary reservoirs for use in intraocular implants.

FIG. 23A shows an exemplary pre-procedure setup, FIG. 23B shows an exemplary approach of a cannula of a delivery device toward the sclera, FIG. 24E shows advancement of the distal tip of the cannula into the anterior chamber, FIG. 24F shows retraction of the cannula to release the drug-eluting implant intramurally, and FIG. 24G shows an exemplary final position of the drug-eluting implant.

FIG. 24C and FIG. 24D show the concentrations of bimatoprost and the bimatoprost acid metabolite, respectively, for three pigs (A3, A4, and A5) implanted with the limbal implant in an animal study.

DETAILED DESCRIPTION

Figure 1:
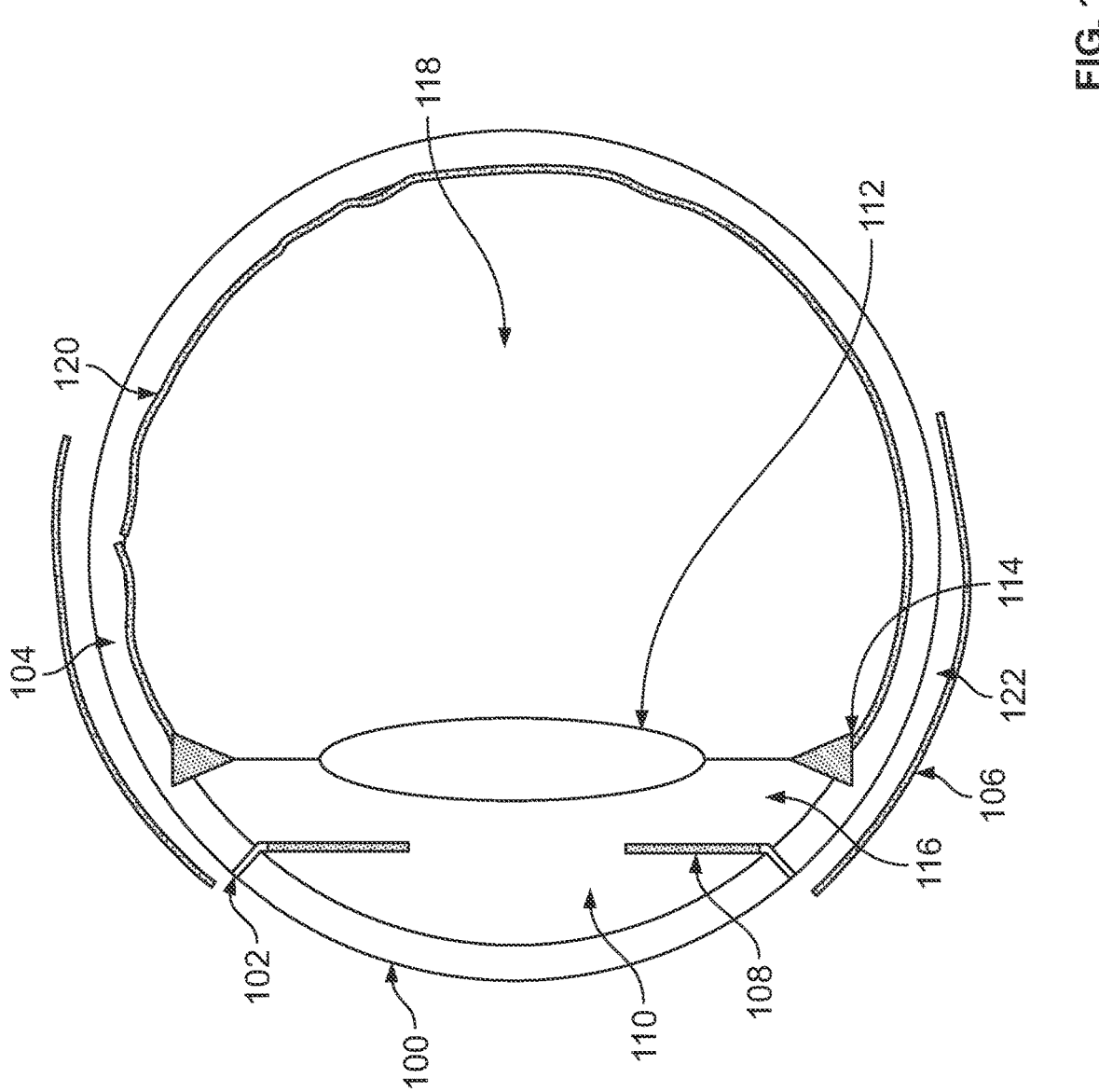
FIG. 1 shows a cross-sectional view of the anatomy of a normal human eye.

Described herein are devices, systems, and methods for treating conditions of the eye (e.g., glaucoma, macular degeneration, and others as described herein). Generally, such devices are intended to be implanted in the eye (e.g., within one or more of the sclera, cornea, limbus, and ciliary sulcus) to release one or more drugs to one or more regions impacted by a disease or condition of the eye. For instance, the devices described herein may be drug-eluting implants. In some instances, the devices may be positioned with at least one end extending into the posterior chamber (e.g., within the sulcus, within the sulcus and partially extending into the remainder of the posterior chamber). For example, in some variations, the devices may be positioned within the sclera or partially within the sclera and the subconjunctival space, with one end extending into the sulcus. In other variations, the devices may be positioned intramurally within the eye. As used herein, intraocular implants (e.g., a drug-eluting implant) may be positioned intramurally when they are embedded fully within one or more tissues of the eye (e.g., sclera, limbus, cornea). In some variations, the intraocular implants may be positioned fully intramurally such that they are fully within the sclera, fully within the limbus, partially in the limbus and partially in the sclera, or partially in the limbus and partially in the cornea.

The devices described herein may generally comprise intraocular implants (e.g., a drug eluting implant) for treating one or more conditions of the eye. The intraocular implants may comprise implant bodies, such as, for example, elongate implant bodies, that may deliver one or more drugs to the eye, and/or that may be coupled to a housing or reservoir that may contain and deliver one or more drugs to the eye. For example, in some variations, the implants may comprise a drug-eluting matrix configured to release one or more drugs into the eye. The intraocular implants may further comprise at least one anchoring element, which may be coupled to the implant body and/or may be formed from the implant body itself. The anchoring element may be configured to secure the intraocular implant in the desired position within the eye. In some variations, and as will be discussed in more detail herein, the implant body may comprise a filament, a rectangular prism, a sheet, a sphere, a spheroid, an ovoid, a cylinder (e.g., a cylindrical capsule, a cylindrical rod), a coil, a screw, and/or a tubular body. In some variations, an implant body may have one or more sharpened, pointed, and/or triangular-shaped ends. An implant body may be configured as a needle, for instance a microneedle. Systems described herein may generally comprise one or more intraocular implants and one or more delivery devices configured to deliver the intraocular implants to an eye of a subject. Moreover, in some instances, one or more intralocular implants (e.g., two, three, four, or more) and one or more delivery devices (e.g., two, three, four, or more) may be packaged as a kit, and the kit may contain the same number of intraocular implants as delivery devices, or a different number of intraocular implants and delivery devices. In some instances, an intraocular implant may be preloaded in a corresponding delivery device, while in other variations, one or more implants may be provided separately from a delivery device, and the implant may be loaded into or otherwise positioned within a delivery device (e.g., within a cannula of a delivery device) by a user. In some variations, multiple implants may be delivered sequentially. In some variations, one or more implants may be delivered simultaneously. For instance, 2, 3, 4, 5, 6, 7, 8, 9, 10, or more implants may be delivered sequentially or simultaneously.

Methods for treating conditions of the eye may generally comprise advancing a drug-eluting implant into the eye, positioning at least a portion of the drug-eluting implant in a location in the eye, and delivering the one or more drugs from the implant to the implant location or another location in the eye to treat the condition of the eye and/or reduce one or more symptoms associated with the condition of the eye. For example, in some variations, methods may generally comprise advancing a drug-eluting implant through the conjunctiva and the sclera of the eye, positioning a portion of the implant in the sclera and a first end of the implant in the sulcus, and delivering a drug from the implant to the sulcus to treat the condition of the eye and/or to reduce one or more symptoms of the condition of the eye. In some variations, methods may generally comprise advancing a drug-eluting implant through the conjunctiva and the cornea of the eye, positioning a portion of the implant in the cornea and a first end of the implant in the anterior chamber, and delivering a drug from the implant to the anterior chamber to treat the condition of the eye and/or to reduce one or more symptoms of the condition of the eye. The implant may partially reside in the iridocorneal angle of the anterior chamber. In some variations, the first end of the implant may reside in the iridocorneal angle of the anterior chamber. In other variations, methods may generally include advancing a drug-eluting implant through one or more of the sclera, limbus and cornea of the eye, positioning the implant entirely within one or more of the sclera, limbus, cornea, and suprachoroidal space, and delivering a drug from the implant to the anterior chamber of the eye to treat the condition of the eye and/or reduce one or more symptoms associated with the condition of the eye. In other variations, methods may generally include advancing a drug-eluting implant through the sclera and limbus of the eye, positioning the implant with one end of the implant in the sclera and one end in the limbus, and delivering a drug from the implant, via diffusion through the limbal tissue, to the anterior chamber of the eye to treat the condition of the eye and/or reduce one or more symptoms associated with the condition of the eye. In some variations, the drug-eluting implant may comprise one or more sharp, pointed, and/or triangular-shaped ends. For example, in some variations, the drug-eluting implant may be in the form of a needle or microneedle. In some instances, the pointed, sharpened and/or triangular-shaped end(s) may assist in placing the implant within the eye such that the implant may at least partially serve as its own delivery system (e.g., the implant may advance through one or more tissues of the eye by means of its one or more sharp, pointed, and/or triangular-shaped ends). Additionally or alternatively, such implants may be advanced using a delivery device. Conditions of the eye may include, but are not limited to, ocular surface diseases, corneal diseases, scleral diseases, uveal diseases, vitreous diseases, optic nerve diseases, choroidal diseases, and retinal diseases.

Generally, implantation of the intraocular implants described herein may be performed in a doctor's office by general ophthalmologists and thus do not require costly surgery performed by a specialist. Moreover, because the implants are at least partially embedded (e.g., at least partially embedded in the sclera, fully embedded in the sclera, cornea, limbus, or a combination thereof) in portions of the eye other than the anterior chamber, use of the implants described may greatly minimize the risk of endothelial cell loss that can occur as a result of free movement of devices (e.g., implants or portions thereof) in the anterior chamber. Some implants are fully embedded in a tissue of the eye and do not extend into the anterior or posterior chambers. The sclera is a tough, dense, collagenous wall this is considered relatively impermeable to various chemicals, however intramural (e.g., fully intramural, partially intramural) implants described herein may provide targeted release of drugs through various tissues of the eye to the desired location, including through the sclera.

Additionally, implants that partially or completely reside in the posterior chamber (e.g., within the sulcus, within the sulcus and partially extending into the remainder of the posterior chamber) may utilize naturally occurring currents (e.g., anterior flowing currents, posteriorly flowing currents), that may deliver a drug to different portions of the eye. For example, it has been shown that aqueous humor produced at the ciliary body and released into the ciliary sulcus and/or posterior chamber can travel anteriorly into the anterior chamber where it travels via convection currents. Thus, in some variations, the implants described herein may be positioned outside of the anterior chamber, thus avoiding the risks associated with conventional implants positioned at least partially within the anterior chamber, and may deliver one or more drugs to the front of the eye (e.g., the anterior chamber). Additionally, newer evidence shows that there is likely a posterior current to aqueous flow into the vitreous and across the retina and retinal pigment epithelium. Although this accounts for a minority of aqueous flow relative to anterior flowing currents, drugs released into the ciliary sulcus from the devices described herein may be able to reach other target anatomy via posterior flows.

Accordingly, the devices, systems, and methods described herein may provide effective treatment for many conditions of the eye while avoiding the costs and consequences of utilizing formal operating rooms, decreasing the total amount of drug needed, reducing or eliminating systemic drug exposure through spatially targeted delivery, decreasing or eliminating the need for frequent injections or daily eyedrops, and increasing patient compliance with suggested treatment regimens by eliminating repeated administration of eye drops or injections used in conventional treatments. The devices, systems, and methods described herein may deliver a much smaller amount of drug to target tissue without compromising on efficacy, and thus drug and preservative side effects may be reduced.

Anatomy

For context, FIG. 1 shows a partial cross-sectional view of the anatomy of a normal human eye. The eye can be conceptualized as a fluid filled sphere. Anteriorly, it is bounded by the cornea (100), a three-layered clear tissue that allows entry of light, and functions like a protective window allowing for entry of light into the eye. The periphery of the cornea (100) is known as the corneal limbus ("limbus") (102) which defines the junction with the sclera (104). The limbus (102) contains stem cells for the ocular surface, contains numerous aqueous outflow pathways, and is highly vascularized.

The sclera (104) is the opaque, tough, protective, outer layer of the eye. Like the cornea it is essentially avascular. Overlying the sclera (104) is the conjunctiva (106), the thin, clear tissue that overlies the sclera (104) and the inside of the eyelids. By contributing mucus and tears, it helps lubricate the ocular surface. In addition, it is vascularized, and it helps contribute to ocular immune responses. The space below the conjunctiva is the subconjunctival space (122).

Posterior to the cornea, is the iris (108), or the colored part of the eye. It is an annular structure which can adjust its aperture (pupil) to regulate the amount of light entering the eye. Bright light causes constriction of the pupil thereby limiting exposure to excessive light or resulting glare. Under dim lighting, the pupil opens to capture more of the available light.

The anterior chamber angle (110), which is filled with aqueous humor, resides between the iris and cornea. At its periphery, there is the anterior chamber angle (110), where aqueous drains out of the eye through the trabecular meshwork and Schlemm's canal.

Behind the iris (108) is the lens (112). The normal lens is transparent, and it focuses light on the retina to create a clear image. With age or disease, the lens (112) may cloud, and this is known as cataract. The lens (112) is suspended in the eye by fibers known as lens zonules. One end of the zonules attach around the equator of the lens (112). The other end of the zonules attaches to the ciliary body (114). Contraction and relaxation of the ciliary body alter load on the zonules thereby resulting in increased curving of the lens or flattening of the lens (112). This is the primary mechanism our eyes use for focusing.

The ciliary body (114) not only contains muscles that apply load to the zonules, but it is also responsible for secreting aqueous humor which travels through the ciliary sulcus (116), the peripheral part of the posterior chamber. Implants or devices residing in the ciliary sulcus or peripheral posterior chamber avoid the visual axis and thus do not interfere with vision. Aqueous humor flows into the ciliary sulcus and posterior chamber into the pupil and ultimately into the anterior chamber (110). Research has also shown that aqueous humor currents can also drive fluid and substances through the vitreous and through the retina. In other words, the currents are bidirectional. The posterior chamber is the space in the eye behind the iris and in front of the lens. At its periphery, it is bounded by the ciliary sulcus (116). The ciliary sulcus (116) is the space between the front of the ciliary body (114) and the posterior surface of the iris. This part of the posterior chamber is typically 12 mm in diameter.

The vitreous humor (118) is the gelatinous substance filling the central cavity of the eye. Its volume is approximately 4-4.5 mL. It is bounded by the retina peripherally and posteriorly. Anteriorly, it is bounded by Berger's space, which separates the vitreous cavity from the lens centrally and by the canal of Petit, also known as spatia zonularis, which separates it from the lens peripherally. The retina is the photosensitive nerve layer lining the back of the eye. In humans, the retina has ten layers, with the outermost, or closest to the sclera (104), being the retinal pigment epithelium. This layer has been implicated in macular degeneration.

Between the sclera and the retina is a part of the uvea known as the choroid (120). It is a high flow, low resistance vascular layer that nourishes and oxygenates the outer two thirds of the retina. It has also been implicated in macular degeneration. The macula is a region of the retina that accounts for high contrast, crisp vision. It is the functional center of the retina and gives humans their central vision. For example, the ability to read or recognize faces clearly is dependent on the macula. Macular degeneration affects this area, and thus can have devastating impact on vision. The optic nerve is the coalescence of approximately 1 million retinal axons carrying visual information from the eye to vision centers in the brain.

Intraocular Implants

In general, the devices described herein comprise intraocular implants for treating one or more conditions of the eye by delivering one or more drugs to the eye. The intraocular implants may comprise an implant body, such as an elongate implant body, one or more anchoring elements, and a drug. The implant body may comprise a first end and a second end and may be configured to be positioned in the eye with the first end in the same, or a different location, as the second end. For example, in some variations, the implant body may be configured to be implanted within the eye such that the first end is positioned in the sulcus or anterior chamber and the second end is positioned in or outside the sclera. For example, in some variations, the implant body may be configured to be implanted within the eye such that the first end is positioned in the sulcus or anterior chamber and the second end is positioned in the sclera or in the subconjunctival space. In other variations, the implant body may be configured to be positioned intramurally within the eye, such as, entirely positioned within the sclera, the cornea, the limbus, or a combination thereof.

As will be described in more detail herein, the implant body may comprise an anchoring element configured to retain the implant within the eye and maintain the implant in the desired position within the eye. The anchor element may be formed from the implant body and/or may be coupled to the implant body. In some variations, the intraocular implants described herein may comprise a plurality of anchoring elements, such as, for example, two, three, four, five, six, seven, or more, including all ranges therein.

The intraocular implants may further comprise one or more drugs. In some variations, the implant body may comprise the one or more drugs, such within a chamber in the implant body and/or within a drug-eluting matrix forming the implant body or coating an exterior surface thereof. In other variations, the intraocular implants may comprise a separate housing coupled to the implant body that may contain or otherwise deliver the drug to the eye. Regardless, the intraocular implants may be drug-eluting or otherwise configured to deliver, administer, or provide one or more drugs to the eye.

Implant Body

In general, the implant bodies disclosed herein may be rounded (e.g., spherical, spheroid, ovoid) and/or elongate. Elongate implant bodies may comprise, for instance, filaments, sheets, rods, cylindrical capsules, coils, screws, and/or tubular bodies. Thus, implant bodies may have a variety of cross-sectional shapes, including, for example, circular, oval, square, and rectangular. In general, the implant body may comprise a first end and a second end and the implant body, or a portion of the implant body, may be hollow to accommodate, for instance, a drug, a solution of a drug, a slurry of the drug, an emulsion of the drug, a drug-eluting matrix, or a drug reservoir. Thus, in some variations, the implant body may comprise a reservoir or cavity between the first and second ends that contains one or more drugs. Alternatively, the implant body, or a portion of the implant body, may be solid. In some variations, all or a portion of the implant body may be coated with a drug-eluting matrix. For example, in some variations, the entire external surface of the implant body may be coated with the drug-eluting matrix or only a portion (e.g., one third, one half, two-thirds, a proximal end or portion, a distal end or portion, or the like) of the implant body may be coated. The implant body may have exterior or interior surface modifications that increase adhesion of a drug or drug-eluting matrix to the surface. In some variations, an implant body may have one or more sharpened, pointed, and/or triangular-shaped ends (e.g., a first end, a second end, or both first and second ends). For example, an implant body may be configured as a needle, for instance a microneedle. In some variations, an implant body may be sharp, configured such that it may pierce a tissue of the eye (e.g., sclera) without the aid of a delivery device. In some instances, such implants (e.g., implants in the form of microneedles) may allow for less invasive and/or less painful implantation than other implant designs.

In some embodiments, the implant body does not comprise a lumen for flow of aqueous humor therethrough. Put another way, in some variations, the intraocular implants described herein may not be used to shunt fluid from one location within the eye to another.

The implant bodies described herein may comprise a variety of materials suitable for use in a human subject. In some embodiments, the implant body may comprise one or more biocompatible materials, such as biocompatible polymers or plastics, polymer composites, ceramics or ceramic composites, glass or glass composites, metals, alloys (e.g., shape-memory alloys, superelastic alloys) or combinations or derivatives of these materials. Examples of biocompatible metals and metal alloys include stainless steel, gold, silver, titanium, tantalum, platinum and alloys thereof, cobalt and chromium alloys, and nickel-titanium alloys such as Nitinol. Examples of biocompatible polymers include poly(lactic-co-glycolic acid) (PLGA), poly(lactic acid) (PLA), poly (glycolic acid) (PGA), high density polyethylene (HDPE), poly(styrene-block-isobutylene-block-styrene) (SIBS), polyurethane, polycarbonate, polypropylene, polymethyl-methacrylate (PMMA), polybutylmethacrylate, polyesters, polytetrafluoroethylene (PTFE), silicone, acrylic polymers, polyvinyl alcohol, polyvinyl pyrrolidone, polyvinyl chloride, ethyl vinyl acetate, collagen, collagen derivatives, flexible fused silica, polyolefins, NYLON® polymers, polyimide, polyacrylamide, fluorinated elastomers, and copolymers and blends thereof. The intraocular implant or implant body may be fully or partially erodible (e.g., biodegradable), and may, for instance, comprise poly(D,L-lactide), poly(D, L-lactide-co-glycolide), poly(D,L-lactide)acid, and polyethylene glycol 3350. Put another way, in some variations, the entire intraocular implant or the entire implant body may be fully erodible (e.g., biodegradable). The rate of elution of a drug from an erodible intraocular implant or implant body described herein may be controlled by selecting an appropriate erodible material (e.g, a polymer) with predictable release characteristics (e.g., rate of release). In some embodiments, the implant body may comprise an erodible drug-eluting matrix with variable erosion rates. For example, in some variations, a first end or portion of the implant body may have a first erosion rate (e.g., the rate at which the drug-eluting matrix is degraded or absorbed) and a second end or portion of the implant body may have a second, different erosion rate. Thus, elution of a drug from an implant or implant body described herein may have a constant or variable rate. In some embodiments, the first erosion rate may be higher than the second erosion rate, or vice versa. In some variations, the implant body may comprise one or more layers, each layer comprising an erodible drug-eluting matrix. They layers may have the same erosion rates, or one or more layers may have different erosion rates. In some variations, the implant body may contain a drug or erodible drug-eluting matrix. In some embodiments, the implant body may comprise an erodible material (e.g., polymer), the erosion rate of which can be tuned by selecting an appropriate material (e.g., polymer). In some variations, the implant body may have a first erosion rate (e.g., the rate at which the housing dissolves), and a drug-eluting matrix contained within may have a second erosion rate (e.g., the rate at which the drug-eluting matrix is degraded or absorbed). In some embodiments, the second erosion rate may be higher than the first erosion rate. Thus, the drug may elute faster than the housing erodes.

In some embodiments, the implant body may be a needle or microneedle. In some embodiments the needle or microneedle may have a length that is similar or equal to the thickness of the sclera (e.g., 0.5 mm to 1 mm), such that it may fully reside in the sclera. In some variations, the needle or microneedle may have a length that is greater than the thickness of the sclera, or less than the thickness of the sclera. In some embodiments, the implant body may extend from the sclera into the anterior chamber, sulcus, or posterior chamber. In some embodiments, a needle or microneedle implant body may be biodegradable, as described herein.

In some embodiments, the implant body may comprise a filament or suture. The implant body may, for instance, comprise a filament or suture comprising a polymer. The filament or suture may comprise a single fiber or may comprise a plurality of fibers, such as, for example, a plurality of braided fibers. In some variations, it may be useful to utilize a filament or suture with braided fibers to strengthen the filament or suture against breakage by mechanical force, such as, during extraction of the implant from the eye. In certain embodiments, the filament or suture may comprise polytetrafluoroethylene (PTFE), polypropylene, polyimide, polyester, or nylon.

In some variations, an implant body configured for placement within the eye may comprise a spherical or rod-shaped implant body configured to be positioned entirely in the sclera. In these variations, the spherical or rod-shaped implant body may comprise an erodible drug-eluting matrix and/or a reservoir containing a drug or drug-eluting matrix. In some variations, all or a portion of the spherical or rod-shaped implant body may be coated with a drug-eluting matrix. In certain variations, the spherical or rod-shaped implant body may comprise an exterior shell and an interior chamber. The interior chamber may accommodate, for instance, a drug, a solution of a drug, a slurry of the drug, an emulsion of the drug, a drug-eluting matrix, or a drug reservoir. In some variations, the implant body may comprise fenestrations in the shell or the shell may be porous to deliver a drug from the interior chamber of the implant body to the eye.

The implant bodies described here may be configured for placement within the eye. For example, the implant bodies may comprise a size and shape suitable for placement and retainment within one or more structures of the eye. For example, in some variations, the implant body may reside partially in the sclera with a first end residing in the sulcus, vitreous, or anterior chamber and a second end residing in the subconjunctival space. In certain variations, the implant body may reside partially in the sclera with a first end residing in the sulcus, vitreous, or anterior chamber and a second end residing in the sclera. In some variations of the implant bodies described herein, when a portion of the implant resides in the anterior chamber, said portion may reside in the iridocorneal angle. For instance, in some variations, the implant body may reside partially in the sclera, cornea, or limbus (e.g., a second end residing in the sclera, cornea, or limbus) with a first end residing in the iridocorneal angle.

In certain variations, the implant body may reside fully within the cornea, such as, for example, with a first end and a second end residing in the cornea. In certain variations, the implant body may reside fully within the sclera, such as, for example, with a first end and a second end residing in the sclera. In certain variations, the implant body may reside partially within the limbus (e.g., the implant body traverses the limbus), with a first end residing in the cornea, a central portion residing in the limbus, and a second end residing in the sclera. In certain variations, the implant body may reside partially within the limbus, with a first end residing in the sclera, a central portion residing in the limbus, and a second end residing in the cornea. In certain variations, the implant body may reside fully intramurally, with a first end residing in the limbus and a second end residing in the sclera. In certain variations, the implant body may reside fully intramurally, with a first end residing in the sclera and a second end residing in the limbus. In certain variations, the implant body may reside fully intramurally, with a first end residing in the limbus and a second end residing in the cornea. In certain variations, the implant body may reside fully intramurally, with a first end residing in the cornea and a second end residing in the limbus. In some variations, the implant body may reside fully within the suprachoroidal space. In some variations, the implant body resides partially within the suprachoroidal space and partially within the sclera (e.g., a first end in the suprachoroidal space and a second end in the sclera, or a first end in the sclera and a second end in the suprachoroidal space). In some variations, the implant body resides partially within the suprachoroidal space and partially within the anterior chamber (e.g., a first end in the suprachoroidal space and a second end in the anterior chamber, or a first end in the anterior chamber and a second end in the suprachoroidal space). In some variations, the implant body is spherical or rod-shaped and resides fully within the sclera, cornea, or limbus.

In some variations, the implant body of the intraocular devices (e.g., an implant, a drug-eluting implant) described herein may comprise a length (or major axis) or width (or minor axis) of between about 10 μm and about 20 mm. In some embodiments, the implant body of the intraocular implants described herein may comprise a length (or major axis) or width (or minor axis) of between about 0.1 mm and about 20 mm, between about 0.1 mm and about 5 mm, between about 0.1 mm and about 4 mm, between about 0.1 mm and about 3 mm, between about 0.1 mm and about 2 mm, between about 0.1 mm and about 1.5 mm, between about 0.1 mm and about 1 mm, between about 0.1 mm and about 0.5 mm, between about 0.5 mm and about 5 mm, between about 0.5 mm and about 4 mm, between about 0.5 mm and about 3 mm, between about 0.5 mm and about 2 mm, between about 0.5 mm and about 1 mm, between about 1.0 mm and about 5.0 mm, between about 1.0 mm and about 4.0 mm, between about 1 mm and about 3 mm, between about 1 mm and about 2 mm, between about 1 mm and about 1.5 mm, between about 1 mm and about 20 mm, between about 2 mm and about 20 mm, between about 2 mm and about 18 mm, between about 2 mm and about 16 mm, between about 2 mm and about 14 mm, between about 2 mm and about 12 mm, between about 2 mm and about 10 mm, between about 2 mm and about 8 mm, between about 2 mm and about 6 mm, between about 2 mm and 4 mm, between about 4 mm and about 20 mm, between about 4 mm and about 18 mm, between about 4 mm and about 16 mm, between about 4 mm and about 14 mm, between about 4 mm and about 12 mm, between about 4 mm and about 10 mm, between about 4 mm and about 8 mm, between about 4 mm and about 6 mm, between about 6 mm and about 20 mm, between about 6 mm and about 18 mm, between about 6 mm and about 16 mm, between about 6 mm and about 14 mm, between about 6 mm and about 12 mm, between about 6 mm and about 10 mm, between about 6 mm and about 8 mm, between about 8 mm and about 20 mm, between about 8 mm and about 18 mm, between about 8 mm and about 16 mm, between about 8 mm and about 14 mm, between about 8 mm and about 12 mm, between about 8 mm and about 10 mm, between about 10 mm and about 20 mm, between about 10 mm and about 18 mm, between about 10 mm and about 16 mm, between about 10 mm and about 14 mm, between about 10 mm and about 12 mm, between about 12 mm and about 20 mm, between about 12 mm and about 18 mm, between about 12 mm and about 16 mm, between about 12 mm and about 14 mm, between about 14 mm and about 20 mm, between about 14 mm and about 18 mm, between about 14 mm and about 16 mm, between about 16 mm and about 20 mm, between about 16 mm and about 18 mm, or between about 18 mm and about 20 mm (including all sub-ranges and values therein). In some embodiments, the implant body length or width of the intraocular devices described herein may be about 1 mm, about 1.5 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, or about 20 mm (including all sub-ranges and values therein).

In some variations, a portion of an implant residing within a cavity of the eye (e.g., anterior chamber, posterior chamber (e.g., sulcus)) may comprise a length (or major axis) of between about 0.1 mm and 5 mm, between about 0.1 mm and 0.5 mm, between about 0.1 mm and 1 mm, between about 0.1 mm and 4 mm, between about 0.1 mm and 3 mm, between about 0.1 mm and 2 mm, between about 0.1 mm and 1.5 mm, between about 0.5 mm and 5 mm, between about 0.5 mm and 4 mm, between about 0.5 mm and 3 mm, between about 0.5 mm and 2 mm, between about 0.5 mm and 1 mm, between about 1 mm and 5 mm, between about 1 mm and 4 mm, between about 1 mm and 3 mm, between about 1 mm and 2 mm, between about 2 mm and 5 mm, between about 2 mm and 4 mm, between about 2 mm and 3 mm, between about 3 mm and 5 mm, between about 3 mm and 4 mm, or between about 4 mm and 5 mm (including all sub-ranges and values therein). In some embodiments, the implant body of the intraocular devices described herein may be about 0.1 mm, about 0.5 mm, about 1 mm, about 1.5 mm, about 2 mm, about 3 mm, about 4 mm, or about 5 mm.

In some variations, a portion of an implant or implant body residing partially intramurally (e.g., cornea, sclera, limbus), or an implant residing wholly intramurally (e.g., cornea, sclera, limbus), may comprise a length (or major axis) of between about 0.1 mm and about 10 mm, between about 0.1 mm and about 5 mm, between about 0.1 mm and about 4 mm, between about 0.1 mm and about 3 mm, between about 0.1 mm and about 2 mm, between about 0.1 mm and about 1.5 mm, between about 0.1 mm and about 1 mm, between about 0.1 mm and about 0.5 mm, between about 0.5 mm and about 5 mm, between about 0.5 mm and about 4 mm, between about 0.5 mm and about 3 mm, between about 0.5 mm and about 2 mm, between about 0.5 mm and about 1 mm, between about 1 mm and about 1.5 mm, between about 1 mm and about 5.0 mm, between about 1 mm and about 4.0 mm, between about 1 mm and about 3 mm, between about 1 mm and about 2 mm, between about 1 mm and about 10 mm, between about 2 mm and about 10 mm, between about 2 mm and about 8 mm, between about 2 mm and about 6 mm, between about 4 mm and about 10 mm, between about 4 mm and about 8 mm, between about 4 mm and about 6 mm, between about 6 mm and about 10 mm, between about 6 mm and about 8 mm, between about 8 mm and about 10 mm. In some embodiments, the implant body of the intramural intraocular devices described herein may be about 1 mm, about 1.5 mm, about 2 mm, about 3 mm, about 4 mm, about 5 mm, about 6 mm, about 7 mm, about 8 mm, about 9 mm, or about 10 mm (including all sub-ranges and values therein).

In some embodiments, the implant body of the intraocular implant or implant bodies described herein have a width (or minor axis) of about 0.1 mm, 0.2 mm, 0.3 mm, 0.4 mm, 0.5 mm, 1.0 mm, 2.0 mm, or 3.0 mm. In some embodiments, the implant or implant body of the intraocular devices may have a width (or minor axis) of between about 0.1 mm and about 2 mm, between about 0.1 mm and about 1.5 mm, between about 0.1 mm and about 1.0 mm, between about 0.1 mm and about 0.5 mm, between about 0.5 mm and about 2 mm, between about 0.5 mm and about 1.5 mm, between about 0.5 mm and about 1.0 mm, between about 1.0 mm and about 2.0 mm, between about 1.0 mm and about 1.5 mm, between about 1.5 mm and about 2.0 mm, between about 0.25 mm and about 1.0 mm, between about 0.1 mm and about 0.5 mm, or between about 0.2 mm and about 0.3 mm (including all sub-ranges and values therein). In certain embodiments, the implants or implant bodies described herein may have a widths of about 0.1 mm, 0.2 mm, 0.3 mm, 0.4 mm, or 0.5 mm.

In some embodiments, the implant body of the intraocular devices described herein are spheres, spheroids, or ovoids, and may have a diameter (or minor axis) of about 0.1 mm, 0.2 mm, 0.3 mm, 0.4 mm, 0.5 mm, 1.0 mm, 2.0 mm, or 3.0 mm. In some embodiments, the implant body of the intraocular devices may have a diameter (or minor axis) of between about 0.1 mm and about 2 mm, between about 0.1 mm and about 1.5 mm, between about 0.1 mm and about 1.0 mm, between about 0.1 mm and about 0.5 mm, between about 0.5 mm and about 2 mm, between about 0.5 mm and about 1.5 mm, between about 0.5 mm and about 1.0 mm, between about 1.0 mm and about 2.0 mm, between about 1.0 mm and about 1.5 mm, between about 1.5 mm and about 2.0 mm, between about 0.25 mm and about 1.0 mm, between about 0.1 mm and about 0.5 mm, or between about 0.2 mm and about 0.3 mm (including all sub-ranges and values therein). In certain embodiments, the implants or implant bodies described herein may have a diameter (or minor axis) of about 0.1 mm, 0.2 mm, 0.3 mm, 0.4 mm, or 0.5 mm.

By way of example, an implant body positioned in a tissue of the eye (e.g., sclera) may be coated with a drug or drug-eluting matrix between the first end of the implant body and the tissue. In some instances, an implant body positioned in a tissue of the eye (e.g., sclera) may be coated with a drug or drug the entire length of the implant (i.e., between the first end and the second end). Accordingly, an implant body positioned in a tissue may only be coated with drug on the portion of the implant body between the first end and the tissue (e.g., the portion fully within the sulcus, fully within the anterior chamber, or fully within the vitreous cavity). In the case of an intraocular implant comprising a housing, the interior, exterior, or both interior and exterior portions of the housing may be coated or filled with a drug or drug-eluting matrix.

The drug-eluting implant may be any suitable size or shape to securely reside at least partially within a limbus of the eye without extending into the anterior chamber. In some variations of the methods described herein, the drug-eluting implant comprises an elongate implant body comprising a first and a second end. The elongate implant body may, for instance be cylindrical, a rectangular prism, a sheet, or any other suitable shape described herein Because the implant bodies described herein may be designed to be removable, in some variations, an implant body may be configured to be retrieved from the eye and may additionally comprise a removal feature configured to be grasped for removal of the implant from the eye. For example, in some variations, the removal feature may comprise a wire, filament, suture, tab, or other structure coupled to the implant body or housing. In these variations, methods may comprise engaging the removal feature of the intraocular implant with an instrument (e.g., forceps) and removing the implant from the eye using the removal feature. In some variations, an implant body (e.g., filament, suture) is also a removal feature. The removal feature may be configured to be positioned in a tissue of the eye (e.g., embedded in the sclera, cornea, or limbus) or may be configured to be positioned either partially or wholly outside of a tissue of the eye (e.g., in the subconjunctival space)

Anchoring Elements

An intraocular implant for treating a condition of the eye may further comprise at least one anchoring element coupled to, or formed from, the implant body. The anchoring element may be any structural feature suitable for holding the intraocular implant in place, preventing the implant body from becoming dislodged from a portion of the eye (e.g., from the sclera, the cornea, the limbus, the sulcus). In variations in which the intraocular implant is implanted partially in the sulcus, the anchoring element may prevent the implant from falling entirely into the sulcus or entirely into the subconjunctival space. Anchoring elements may be present on any portion of the implant body, including any portion of the implant body residing within the sclera, within the sulcus, between the first end of the elongate implant body and the sclera, or within the subconjunctival space. Suitable anchoring elements may comprise knots, beads, barbs, crossbars, heads, enlarged (e.g., rounded) or extended portions of an implant body, or any other feature configured to maintain placement and/or orientation of an intraocular implant and/or implant body within the eye.

Anchoring elements may be expandable such that they remain folded or stowed prior to implantation and/or during removal of the implant from the eye and deploy upon implantation. For example, one or more anchoring elements may have a first compressed or low-profile, undeployed configuration or position and a second expanded, deployed configuration or position. The anchoring elements may be in the first, undeployed, position during advancement of the intraocular implants into the desired position in the eye, and the anchor elements may transition to the deployed position during or after implantation (e.g., during or after release of the implants from a delivery device). Upon proper positioning of the implant, the anchoring elements may be in the expanded, deployed configuration and may assist in securing the implant in the appropriate location, position and orientation. In some variations, expandable anchoring elements may comprise barbs (e.g., with sharpened distal tips) or crossbars, which may extend from the elongate implant body when in the expanded configuration. The barbs and/or crossbars may extend from the implant body at any suitable angle relative to a longitudinal axis of the implant body, such as, for example, between 20 degrees and 160 degrees, including all values and sub-ranges therein. In some variations, the barbs and/or crossbars may extend at about a 45 degree, about a 90 degree, or between about a 45 degree and about a 90-degree angle relative to the longitudinal axis of the implant body. Anchoring elements may be comprised of shape-memory metal, shape-memory alloys, or shape-memory polymers which may change shape upon delivery (e.g., expand to secure the position of the implant body). An anchoring element may expand upon delivery due to fluid absorption. Anchoring elements may additionally be erodible. In some embodiments comprising erodible anchoring elements, the erodible anchoring elements may erode at a different rate (e.g., faster, slower) than another erodible element of the intraocular implant (e.g., a housing).

In some instances, an anchoring element may be a portion of the implant body. For example, in some variations, the anchoring element may be an enlarged portion of the implant body (e.g., a thread or suture). For example, the first end of the implant body may be larger (e.g., in diameter or in width) than a central portion and/or second end of the implant body and/or a second end of the implant body may be larger (e.g., in diameter or in width) than a central portion and/or a first end of the implant body. In some variations, both ends of the implant body may be larger than a central portion of the implant body. Put another way, one or both ends of the implant body may be deliberately enlarged to minimize potential movement. Additionally, in some embodiments, the enlarged portion(s) (e.g., enlarged first end, enlarged second end) may be fully erodible. Having an enlarged portion/anchoring element that is fully erodible may be advantageous as it may allow for easier removal of the remainder of the implant body once the erodible portion has fully dissolved (e.g., the intraocular implant can be retrieved by a non-erodible portion of the implant body or other non-erodible portion of the intraocular implant). In some variations, the anchoring element may be a portion of the implant body that changes shape upon implantation/delivery to the eye, and/or that expands upon implantation/delivery to the eye (e.g., by gaining moisture). In variations comprising a portion of the implant body that serves as an anchoring element (e.g., one or more enlarged ends, shape-changing portion, expanding portion), the anchoring element (e.g., more enlarged ends, shape-changing portion, expanding portion) may reside in any of the locations described herein, such as, for example, in the sulcus, the anterior chamber, the cornea, the sclera, the limbus, or the subconjunctival space.

In some variations, the implant body may not comprise an anchoring element and the entire implant body may be used to anchor the intraocular implant. For example, in some variations, the entire implant body may expand (e.g., by gaining moisture) to secure the implant in place. Additionally or alternatively, the implant body, and thus the intraocular implant, may be secured by positioning the implant or a portion of the implant (e.g., the implant body) within a channel or cavity created in a tissue prior to implantation that has a smaller diameter or width than the diameter or width of the portion of the implant positioned therein after implantation (e.g., implant body).

In some variations, an intraocular implant may comprise a plurality of anchoring elements. For example, in some variations, the intraocular implant may comprise two, three, four, five, six, or more anchoring elements, each of which may assist in retaining the intraocular implant in the appropriate position and orientation within the eye. In these variations, the plurality of anchoring elements may be the same, or one or more of the anchoring elements may be different from one or more of the remaining anchoring elements. Each anchoring element may be independently positioned on any portion of the implant body in order to prevent the implant body from becoming dislodged (e.g., from the sclera). Utilizing multiple anchoring elements may, for instance, allow for precisely controlling the depth or location of implantation of the intraocular implant. Suitable positions for the anchoring elements include, for instance, at a first end of the implant body, at a second end of the implant body, on a proximal portion of the implant body, on a distal portion of the implant body, between the first and second ends of the implant body (e.g., equally or unequally spaced along a length of the implant body). In some variations, one or more of the anchoring elements may be positioned along the implant body a distance corresponding to the thickness of the sclera such that one or more anchoring elements may be positioned on one side of the sclera and one or more anchoring elements may be positioned on the opposite side of the sclera.

In use, one or more anchoring elements may be positioned in various portions of the eye. For example, in some variations, one or more of the anchoring elements may be positioned within the sclera. In some variations, one or more of the anchoring elements may be positioned in the subconjunctival space. In some variations, one or more of the anchoring elements may be positioned in the suprachoroidal space. In variations in which one or more anchoring elements is positioned along a length of the implant body (i.e., between the ends of the implant body), once implanted, one or more anchoring elements may be positioned along a length of the implant body between the first end of the implant body and the sclera and/or along a length the implant body between the sclera and the second end of the implant body.

When a plurality of anchoring elements is employed, the anchoring elements may be positioned within the same structure in the eye (e.g., the sclera) or within different structures in the eye (e.g., one or more in the sclera, one or more in the subconjunctival space). For example, in some embodiments, one or more anchoring element may be positioned within the sclera and one or more other anchoring elements may be positioned between the first end or second end of the implant and the sclera. In some instances, one or more anchoring elements may be positioned between the second end of the implant body and the sclera and one or more other anchoring elements may be positioned between the first end of the elongate implant body and the sclera. In some embodiments, the at least one anchoring element comprises a plurality of beads or barbs positioned along a length of the implant body. A plurality of beads of barbs may serve to simultaneously anchor the elongate implant body at multiple locations (i.e., in the subconjunctival space, within the sclera, and in the sulcus). A plurality of anchoring element may also be used for intraocular implants positioned entirely intramurally. For instance, for implant bodies positioned entirely within the cornea, one or more anchoring elements may be positioned along the implant body entirely within the cornea. In some embodiments, the implant body may be positioned partially in the cornea and partially in the limbus, and one or more anchoring elements may be positioned along the portion of the implant body within the cornea and/or the portion of the implant body within the limbus. In some embodiments, the implant body may be positioned partially in the sclera and partially in the limbus, and one or more anchoring elements may be positioned along the portion of the implant body within the sclera and/or the portion of the implant body within the limbus. In some embodiments, the implant body may be positioned partially in the cornea, partially in the limbus, and partially in the sclera, and one or more anchoring elements may be positioned along the portion of the implant body within the sclera and/or the portion of the implant body within the limbus and/or the portion of the implant body within the cornea. In some embodiments, the implant body may be positioned fully in the suprachoroidal space, and one or more anchoring elements may be positioned along the portion of the implant body within the suprachoroidal space. In some embodiments, the implant body may be positioned partially in the suprachoroidal space and partially in the anterior chamber, and one or more anchoring elements may be positioned along the portion of the implant body within the suprachoroidal space and/or along the portion of the implant body within the anterior chamber.

Housing

The intraocular implant described herein may further comprise a separate housing coupled to the implant body (such as, for example, to an end of the implant body), that is configured to deliver one or more drugs to the eye. The housing may take any form suitable for delivery of drug to the eye, such as, for example, a canister, a coil, a bag, and/or a cage. The housing may comprise a shell with a cavity or interior chamber containing one or more drugs, may be formed from a drug-eluting matrix, and/or an external surface of the housing may be coated with a drug-eluting matrix. In some variations, the housing may be a canister comprising a shell and a hollow interior chamber. The interior chamber may accommodate, for instance, a drug, a solution of a drug, a slurry of the drug, an emulsion of the drug, a drug-eluting matrix, or a drug reservoir. The canister may have any suitable cross-sectional shape, such as, for example, circular, oval, square, triangular or the like.

In variations comprising an interior chamber, to facilitate the release of drug, the housing may comprise one or more openings from which drug may elute from the interior chamber and/or the housing may be porous (e.g., made from a material porous to the drug). For example, in some variations, the housing may comprise fenestrations in the shell or the shell may be porous to deliver a drug from the interior chamber of the housing to the eye. The size, shape, and quantity of fenestrations and/or the porosity may be selected to achieve a desired drug release profile. In some variations, the housing may comprise a porous bag. In some instances, the housing may comprise first and second ends, and one or both of the ends may be open such that drug may be delivered through the open end(s). In variations comprising an interior chamber, both ends may be closed, such that drug is delivered through openings in the shell, and/or one or both ends may be open such that drug is delivered either through one or both ends, or through one or both ends and openings in the shell. In some embodiments, one or both ends of the housing may be partially closed and partially open. For example, a first end of the housing may comprise a first opening and/or a second end of the housing may comprise a second opening. In variations in which the housing comprises a canister, the canister may comprise a first canister end and a second canister end. The first and second canister ends may each be open or have openings, may each be closed, and the canister body or shell may have openings, or either end may be open or have openings while the other end is closed. Any of the aforementioned openings may be sealed with a membrane permeable or semi-permeable to the drug.

In some embodiments, the housing may comprise a non-erodible housing. In some embodiments, the housing may comprise a non-erodible housing that is coated or filled with a drug-eluting matrix. The drug eluting matrix may be erodible or non-erodible. For instance, in some variations, the housing may comprise a non-erodible bag, sac, cage, or canister that contains a drug or erodible drug-eluting matrix. In some variations, the housing may comprise an erodible bag, sac, cage, canister, or other container that contains a drug or erodible drug-eluting matrix. In some embodiments, the housing may comprise an erodible material (e.g., polymer), the erosion rate of which can be pre-determined by selecting an appropriate material (e.g., polymer). In some variations, the housing may have a first erosion rate (e.g., the rate at which the housing dissolves), and a drug-eluting matrix contained within the housing may have a second erosion rate (e.g., the rate at which the drug-eluting matrix is degraded or absorbed). In some embodiments, the second erosion rate may be higher than the first erosion rate. Thus, the drug may elute faster than the housing erodes.

Figures 2F, 2G, 2H, 2I, 2J:
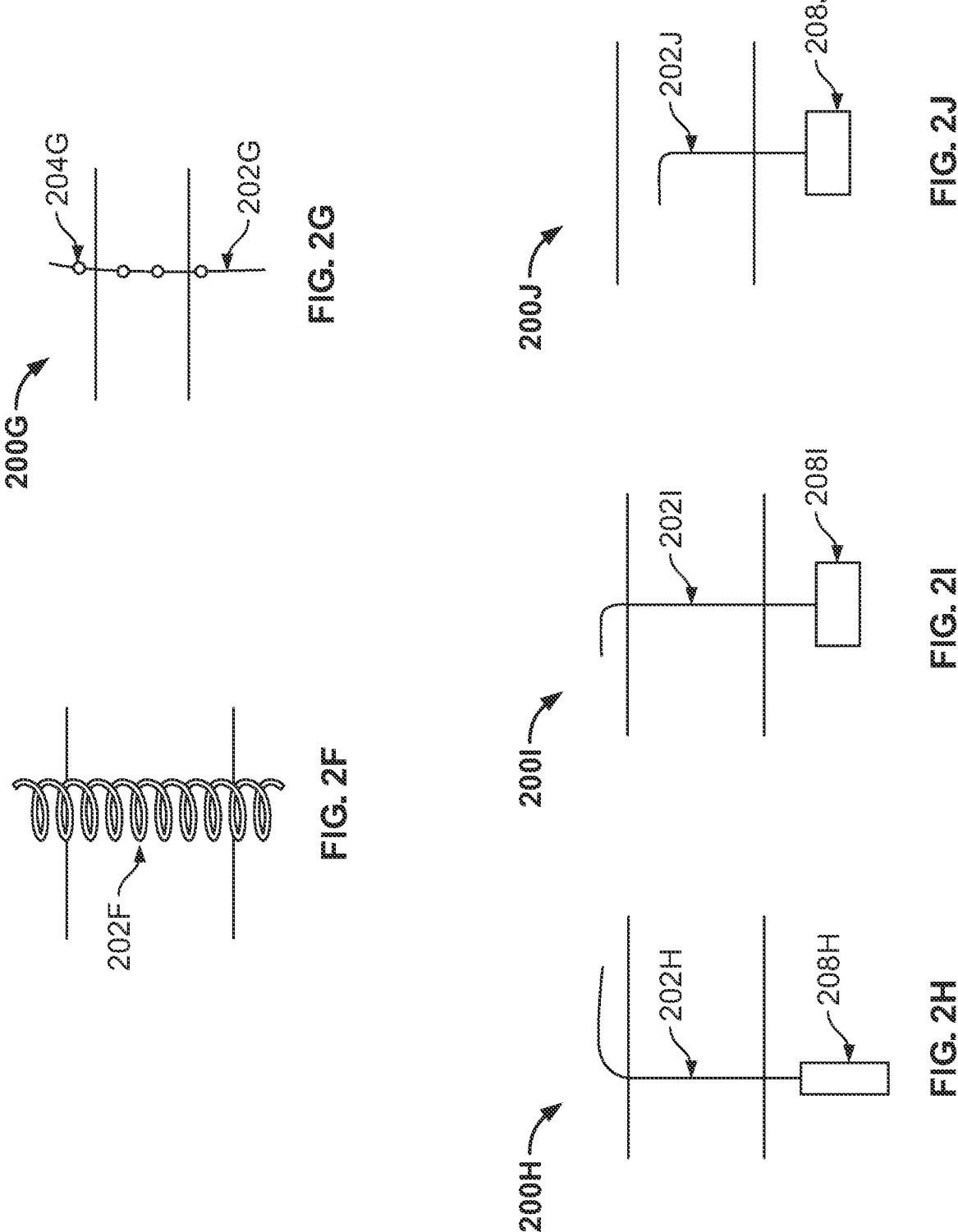

As described herein, the housing may be attached to the implant body in any suitable orientation. For instance, the elongate implant body may comprise a first longitudinal axis and the housing may comprise a second longitudinal axis. In some variations, the housing may be coupled to the implant body such that the first longitudinal axis is parallel with the second longitudinal axis, while in other variations, the housing may be coupled to the implant body such that the first longitudinal axis is transverse to the second longitudinal axis. An intraocular implant comprising an implant body and a housing with parallel longitudinal axes is depicted in FIG. 2H and an intraocular implant comprising an implant body and a housing with transverse longitudinal axes is depicted in FIG. 2I. In variations in which the longitudinal axes are transverse, the angle between the longitudinal axes may be, for example, about 90 degrees, between about 85 and about 90 degrees, between about 80 and about 85 degrees, etc.

When intraocular implants comprise a housing, the housing may be positioned in any location described herein to which delivery of drug is desired. For example, the housing may be positioned inside the sulcus or anterior chamber, or within a mural tissue or combination of mural tissues (e.g., sclera, limbus, cornea).

In some variations, the intraocular implants described herein may be refillable (or a reservoir containing the drug contained therein may be replaceable) so that a single intraocular implant may provide treatment for a longer duration. For example, in some variations, an intraocular implant (e.g., implant body, housing) may comprise a refillable or replaceable reservoir (e.g., coupled or attached to an implant body, within an implant body, within a housing) containing the drug. Thus, once the bolus of drug initially contained within the intraocular implant at implantation has eluted to or otherwise been delivered to the eye, the reservoir may be refilled with a second bolus of drug or replaced with a second reservoir containing a second bolus of drug. In some variations, the first bolus of drug may be the same as the second bolus of drug, while in other variations, the first and second (or subsequent) boluses of drug may be different (e.g., may contain different active ingredients, may contain different volumes of drug, etc.). The drugs in the intraocular implants described herein may be replaced and/or refillable any suitable number of times, such as, for example, two, three, four, five or more. Additionally, the drugs may be replaced and/or refilled in-situ (e.g., while the intraocular implant remains positioned within the eye), or the intraocular implant may be removed from the eye, the drug may be refilled or replaced, and the intraocular implant may be re-inserted into the eye. In variations in which the intraocular implant (e.g., implant body, housing) is refillable, the intraocular implant may be refilled, for instance, by injecting a drug, drug-eluting matrix, drug slurry, or the like by needle through a port, opening, or fenestration. For instance, an implant may be refilled from a syringe, catheter, or the like under topical anesthesia.

In some cases, it may be advantageous for the drug of the intraocular implants described herein to be integrated into a material forming a portion of the intraocular implant (e.g., implant body, housing) such that the intraocular implant comprises a drug-eluting matrix. As used herein, a "drug-eluting matrix" refers to a material impregnated with a drug, where the drug is released from the material when positioned within the eye. In some variations, the drug may be released slowly from the material over a set period of time. The drug-eluting matrix may, for instance, comprise a polymer impregnated with the drug, where the drug is released from the polymer while implanted within the eye. In certain embodiments, the drug-eluting matrix may be erodible such that it dissolves or disintegrates within a predetermined period of time inside the subject, safely, into non-toxic or biocompatible components. The drug-eluting matrices described herein may form a coating on, or a filler within, a structure of the intraocular implants described herein. For instance, in some embodiments, the implant body may comprise a hollow interior chamber containing the drug-eluting matrix and the implant body may further comprise fenestrations (e.g., openings) through a wall of the implant body to deliver the drug from the drug-eluting matrix in the interior chamber to the eye. Additionally or alternatively, all or a portion of the intraocular implant may comprise a drug-eluting matrix in the form of a coating. For instance, in some embodiments, the intraocular implants may comprise a coating on only a first portion of the implant (e.g., on only the implant body, on only a portion of the implant body, on only a housing, on only a portion of a housing) and a second portion of the implant may remain uncoated (e.g., a second portion of the implant body, a portion of the housing). In some embodiments, the first portion of the implant is between the first end of the implant body and the sclera Drugs The intraocular implants may comprise one or more drugs (e.g., two, three, four, five, or more) useful for treating the condition of the eye. In some embodiments, the condition of the eye may be glaucoma, AMD, retinal diseases (e.g., retinal vascular disease), nerve disease, corneal disease, lens diseases, uvea diseases, vitreous diseases, surface diseases, lid diseases, or ocular infections. In some embodiments, the drug may comprise a drug suitable for treating glaucoma, and diseases of the retina, lens, cornea, uvea, vitreous, iris, ciliary body, sclera, or ocular surface. Such drugs include, but are not limited to, steroids (e.g., prednisolone, prednisone, cortisone, cortisol, triamcinolone, or shorter acting steroids), anti-VEGF agents, prostaglandins, nitric oxide-releasing drugs, nitric oxide donors, beta blockers, miotics, carbonic anhydrase inhibitors, ROCK inhibitors, parsympathomimetics, sympathomimetics, alpha 2 adrenergic agonists, antimetabolites (e.g., fluoruracil mitomycin C), antibiotics, steroids, non-steroidal anti-inflammatory drugs (NSAIDs), antifungals, immunosuppressants (e.g., cyclosporine), vitreous hemorrhage drugs, collagenases, vitreous floater treatments, pupil dilators, pupil constrictors, heparin, other anticoagulants, fibrinolytic compounds, and monoclonal antibodies or other biologics. In certain embodiments, the drug is a nitric oxide-releasing drug in combination with a prostaglandin or other glaucoma drug (e.g., to target multiple mechanisms of action). In certain embodiments, the drug is useful for lowering intraocular pressure. In certain embodiments, the drug may suppress production of aqueous humor. In some embodiments, the drug may increase the drainage of aqueous humor through a trabeculocanalicular pathway and/or a uveoscleral pathway. In some embodiments, the drug is latanoprost, travoprost, bimatoprost, ranibizumab, aflibercept, bevacizumab, brolucizumab, riboflavin, unoprostone, or corticosteroid.

As described below, drugs suitable for delivery by the implants described herein may diffuse from the location of implantation in one tissue of the eye (e.g., sclera, cornea, limbus) to another location in the eye (e.g., anterior chamber, posterior chamber). To enhance this diffusion from the implant location to another location in the eye, the drugs described herein may be administered together with the application of one or more penetration enhancers. Penetration enhancers may include, for instance, compounds such as cyclodextrins, chelating agents, crown ethers, bile acids, bile salts, surfactants, cell-penetrating peptides, and amphiphilic compounds. Such penetration enhancers may be combined with the drug to treat a condition of the eye being administered by an intraocular implant described herein, or they may be administered separately. In some variations, a first intraocular implant delivers a drug to treat a condition of the eye, and a second intraocular implant delivers a penetration enhancer. In other variations, one intraocular implant delivers both a drug to a treat a condition of the eye and a penetration enhancer. Penetration enhancers may also be non-compound penetration enhancers, which are applied separately and in addition to the implant. For instance, a non-compound penetration enhancer may include electrical currents, iontophoresis, ultrasound, or microneedles. These may, for instance, be applied to a tissue of the eye to increase penetration of a drug delivery by an intraocular implant described herein. Selection of the appropriate penetration enhancer may depend upon the properties of the drug being administered (e.g., molecular weight, hydrophobicity/lipophilicity). An appropriate penetration enhancer may be selected for enhancing penetration of a drug through a specific tissue (e.g., cornea, sclera).

Currently available treatments for eye disorders such as glaucoma use medicated drops that persist for less than 24 hours. For AMD and retinal diseases, certain other ocular injections provide delivery of drugs to eye tissues for a few weeks or a few months. In contrast, the intraocular implants described herein allow for the continuous or semi-continuous delivery of one or more drugs for days or weeks, and/or months or years. In some embodiments, the drug is delivered to the eye over a predetermined period of time, such as, for example, over at least about 1, 2, 3, 6, 9, 12, 18, 24, 30, 36, 48, 60, or 72 months (including all values and sub-ranges therein). For example, in some variations, the intraocular implant is configured to for sustained-release of drug to the eye for between about 1 month and about 3 months, about 2 months and about 4 months, about 1 month and about 6 months, about 6 months and about 9 months, about 6 months and about 12 months, about 12 months and about 18 months, about 12 months and about 24 months, about 24 months and about 36 months, about 12 months to about 72 months or about 1 month to about 72 months. In certain embodiments, the period of time is at least about 1 year, 5 years, 10 years, 15 years, 20 years or between about 1 year and about 5 years, about 1 year and about 10 years, about 5 years and about 10 years, about 5 years and about 15 years, about 10 years and about 20 years, about 5 years and about 20 years or about 1 year and about 20 years.

The implants described herein may be biodegradable. In some variations, one or more implants may be delivered to one or more tissues of the eye when one or more implants degrades within the eye. For instance, a new implant may replace a partially or fully degraded implant every month, every 3 months, every 6 months, every 12 months, every 18 months, every 2 years, every 3 years, or more, or at any interval therein.

As discussed previously, in variations in which the intraocular implant is positioned at least partially within the sulcus, the drug delivered from the intraocular implant may be taken up by anterior and/or posterior flowing currents such that it may be delivered to the anterior and/or posterior chambers of the eye. In these variations, an end of the implant body (e.g., first end, second end) may be configured to elute drug (e.g., may have a drug-eluting coating, may have one or more openings to allow for delivery of drug from within the implant body) and this end may be positioned within the sulcus. In some variations, the drug may be delivered to the anterior chamber, the posterior chamber (e.g., the sulcus and/or remainder of the posterior chamber), the cornea, the iris, the lens, the pupil, the cornea, the retina, or the vitreous body. In variations in which the intraocular implant is positioned intramurally, the drug may be delivered through the sclera to the anterior chamber, through the sclera to the posterior chamber, through the cornea to the anterior chamber, through the cornea to the posterior chamber, through the limbus to the anterior chamber, or through the limbus to the posterior chamber.

Implant Locations

Intraocular implants may reside in a tissue of the eye, wherein an implant body resides at least partially in the sclera, and a first end of an implant body resides in the posterior chamber (e.g., within the sulcus, within the sulcus and partially extending into the remainder of the posterior chamber), anterior chamber, Berger's space, Canal of Petit, or Canal of Hannover. For example, in some variations, the implant body may reside partially in the sclera with a first end residing in the sulcus or anterior chamber and a second end residing in the subconjunctival space (e.g., the implant body traverses the sclera). In certain variations, the implant body may reside partially in the sclera with a first end residing in the sulcus or anterior chamber and a second end residing in the sclera (e.g., the implant body does not reside in the subconjunctival space). In some variations, the implant body may reside partially in the sclera with a first end residing in Berger's space, the Canal of Petit, or the Canal of Hannover, and a second end residing in the subconjunctival space (e.g., the implant body traverses the sclera). In certain variations, the implant body may reside partially in the sclera with a first end residing in Berger's space, the Canal of Petit, or the Canal of Hannover, and a second end residing in the sclera. It should be understood that intraocular implants or implant bodies described herein as positioned in or residing within the sulcus may or may not extend out of the sulcus into the remainder of the posterior chamber. For example, in some variations implant bodies positioned or residing within the sulcus may have an end positioned within the sulcus such that the implant body does not extend beyond the sulcus into the remainder of the posterior chamber. For example, in some variations, implants may only extend less than about 1 mm, less than about 0.5 mm, about 0.5 mm, about 1.0 mm, or between about 0.5 mm and about 1.0 mm into the sulcus and does not extend beyond the sulcus into the remainder of the posterior chamber.

In other variations, implant bodies positioned or residing within the sulcus may traverse or partially reside in the sulcus but may extend into the remainder of the posterior chamber such that an end of the implant body resides just beyond the sulcus in the posterior chamber. For example, in some variations, implants may only extend less than about 2 mm, less than about 1 mm, less than about 0.5 mm, less than about 0.25 mm, between about 2 mm and about 0.25 mm, between about 2 mm and about 0.5 mm, between about 2 mm and about 1 mm, between about 1 mm and about 0.25 mm, between about 1 mm and about 0.5 mm, or between about 0.5 mm and about 0.25 mm beyond the sulcus into the posterior chamber.

The intraocular implants or portions thereof (e.g., implant bodies, housings) described herein may be positioned such that they avoid damaging endothelial cells. Implants may, for instance, be positioned partially within the posterior chamber (e.g., within the sulcus, within the sulcus and partially extending into the remainder of the posterior chamber) as described in greater detail herein. Implants may also be positioned partially within the anterior chamber, however, implants positioned partially in the anterior chamber may extend into the anterior chamber to a depth that would not damage the endothelial cells. For example, in some variations, implants may only extend less than about 2 mm, less than about 1 mm, less than about 0.5 mm, less than about 0.25 mm, between about 2 mm and about 0.25 mm, between about 2 mm and about 0.5 mm, between about 2 mm and about 1 mm, between about 1 mm and about 0.25 mm, between about 1 mm and about 0.5 mm, or between about 0.5 mm and about 0.25 mm into the anterior chamber.

Intraocular implants may also reside fully intramurally (e.g., embedded or positioned entirely within a tissue or tissues of the eye), such as, for example, the cornea, sclera, limbus, or a combination thereof. In certain variations, the implant body may reside fully within the cornea, such as, for example, with a first end and a second end residing in the cornea. In certain variations, the implant body may reside fully within the sclera, such as, for example, with a first end and a second end residing in the sclera. In certain variations, the implant body may reside partially within the limbus, with a first end residing in the cornea, a second end residing in the sclera, and a portion therebetween residing in the limbus. In certain variations, the implant body may reside partially within the limbus, with a first end residing in the sclera, a second end residing in the cornea, and a portion therebetween residing in the limbus. In certain variations, the implant body may reside fully intramurally, with a first end residing in the limbus and a second end residing in the sclera. In certain variations, the implant body may reside fully intramurally, with a first end residing in the sclera and a second end residing in the limbus. In certain variations, the implant body may reside fully intramurally, with a first end residing in the limbus and a second end residing in the cornea. In certain variations, the implant body may reside fully intramurally, with a first end residing in the cornea and a second end residing in the limbus.

It may be beneficial for intraocular implants or implant bodies to have one portion and/or end residing at least partially intramurally and another portion and/or end to reside outside of the eye (e.g., in the subconjunctival space). In some variations, an implant resides partially in the sclera and partially outside the eye (e.g., in the subconjunctival space). In some variations, an implant resides partially in the limbus and partially outside the eye (e.g., in the subconjunctival space).

It may also be beneficial for intraocular implants or implant bodies residing fully intramurally to interface with an interior structure of the eye. For instance, in some variations, an implant may be fully embedded within the sclera such that a first end of the implant or implant body penetrates the inner scleral wall but does not protrude into the anterior chamber. In some variations, an implant may be embedded at least partially in the limbus, partially in the limbus and partially in the sclera, or partially in the limbus and partially in the cornea, without protruding into the anterior chamber, but may interface with an interior structure or cavity of the eye (e.g., anterior chamber). In other words, one tissue (e.g., limbus) may interface with another structure or cavity of the eye (e.g., anterior chamber, cornea, sclera). In some variations, an implant may be partially or fully embedded within the limbus, such that a first end of the implant or implant body penetrates the limbus but does not protrude into the anterior chamber. As described above, positioning an implant in this manner may avoid damaging endothelial cells (e.g., corneal endothelial cells).

An intramural implant residing at least partially in the limbus may reside 100% within the limbus. In some variations, an intramural implant residing at least partially in the limbus may reside 1-10%, 10-20%, 20-30%, 30-40%, 40-50%, 50-60%, 60-70%, 70-80%, 80-90%, or 90-100% within the limbus. In some variations, an intramural implant may reside about 5%, 10%, 20%, 30%, 40%, 50%, 60%, 70%, 80%, or 90% within the limbus. An intramural implant may also, for example, reside (by length of the implant body) approximately ⅓ in the cornea and ⅔ in the limbus, ⅔ in the cornea and ⅓ in the limbus, ⅓ in the limbus and ⅔ in the sclera, ⅔ in the limbus and ⅓ in the sclera, or ⅓ in each of the cornea, limbus, and sclera. An implant may also reside ½ in the cornea and ½ in the limbus, or ½ in the limbus and ½ in the sclera. In some variations, an implant resides about 10% in the limbus and 90% in the cornea and/or sclera; about 20% in the limbus and about 80% in the cornea and/or sclera; about 30% in the limbus and 70% in the cornea and/or sclera; about 40% in the limbus and about 60% in the cornea and/or sclera; about 50% in the limbus and 50% in the cornea and/or sclera; about 60% in the limbus and about 40% in the cornea and/or sclera; about 70% in the limbus and 30% in the cornea and/or sclera; about 80% in the limbus and about 20% in the cornea and/or sclera; or about 90% in the limbus and 10% in the cornea and/or sclera. It should be understood that "X % within the cornea and/or sclera" encompasses any sub-combination therein (e.g., where X % is 60%, the corresponding values may be 30% in the sclera and 10% in the cornea, or any other combination adding up to 40%).

Exemplary Intraocular Implants

Turning now to the figures, FIGS. 2A-2G depict variations of intraocular implants comprising implant bodies and, in some variations, one or more anchoring elements. FIGS. 2H-2J depict variations of intraocular implants comprising implant bodies and a separate, drug-eluting housing. It should be appreciated that any of the intraocular implants depicted in FIGS. 2A-2J may comprise any of the anchoring elements described herein, and may further comprise a drug-eluting housing, even if not depicted in the variations shown in FIGS. 2A-2J.

FIGS. 2A-2E depict intraocular implants (200A-200E) comprising an implant body in the form of an elongate cylindrical member (202A-202E). Each of the elongate cylindrical members (202A-202E) may be tubular, such that each has a lumen or cavity therein, or each may be solid. One or more drugs may be contained within the elongate cylindrical member (202A-202E) (e.g., within a reservoir in the cavity or lumen of the elongate cylindrical member, within a drug-eluting matrix forming the elongate cylindrical member) and/or all or a portion of the elongate cylindrical member (202A-202E) may be coated with a drug-eluting matrix containing one or more drugs. FIG. 2F depicts an intraocular implant (200F) comprising an implant body (202F) in the form of a coil and FIG. 2G depicts an intraocular implant (200G) comprising an implant body (202G) in the form of a filament.

As described herein, the intraocular implants may comprise one or more anchoring elements, variations of which can be seen in FIGS. 2A, 2B, 2C, 2D, 2E, and 2G. Starting with FIG. 2A, implant body (202A) may comprise a first anchoring element (204A) and a second anchoring element (206A). The first anchoring element (204A) may comprise one or more (e.g., two, three, four, or more) expandable arms at or near a first end of the implant body (202A) and the second anchoring element (206A) may comprise a flat or curved head (e.g., with a circular shape) or crossbar at or near a second end of the implant body (202A). In some variations, the intraocular implant (202A) may have a configuration similar to a dry-wall screw or anchor (tubular body with expandable arms and head). In this variation, in use, the head or crossbar may be positioned on a first side of tissue (e.g., sclera) and the expandable arms may be positioned on a second, opposite side of the tissue (e.g., sclera). In other variations, the head or crossbar may be sunken into the tissue, such that a top surface of the head or crossbar is aligned with the surface of the tissue.

Moving to FIG. 2B, the implant body (202B) of the intraocular implant (200B) may comprise a first anchoring element (204B) and a second anchoring element (206B). The first anchoring element (204B) may comprise threads or a coil positioned along all or a portion of the length of implant body, and the second anchoring element (206B) may comprise a flat or curved head (e.g., with a circular shape) or crossbar at or near a second end of the implant body (202B). In some variations, the implant body (202B) may be tubular, and the threads or coil may be positioned within tissue (e.g., within the sclera), and the head or crossbar may be positioned on a first side of tissue (e.g., sclera). In other variations, the head or crossbar may be sunken into the tissue, such that a top surface of the head or crossbar is aligned with the surface of the tissue.

As depicted in FIG. 2C, the implant body (202C) of the intraocular implant (200C) may comprise one or more (e.g., two, three, four, or more) anchoring elements (204C) along the length of the implant body (202C). The anchoring elements (204C) may comprise crossbars or barbs. The crossbars or barbs may be positioned within a tissue (e.g., sclera), on a first side of a tissue (e.g., sclera), on a second, opposite side of the tissue (not depicted) or a combination thereof. In some variations, the crossbars or barbs may be positioned on a first side of a tissue and within a tissue.

As depicted in FIG. 2D, the implant body (202D) of the intraocular implant (200D) may comprise one or more (e.g., two, three, four, or more) anchoring elements (204D) along the length of the implant body (202D) and the anchoring elements (204D) may comprise beads. The beads may be positioned within a tissue (e.g., sclera), on a first side of the tissue (e.g., sclera), and/or on a second, opposite side of the tissue (e.g., sclera). In some variations, the beads may be positioned on a first side of a tissue on a second, opposite side of a tissue, and within the tissue, as depicted in FIG. 2G. The intraocular implant (202D) may further comprise a housing (208) coupled to the implant body (202D) carrying one or more drugs, as described in detail herein. In some variations, the implant body may reside partially in the sulcus, partially in the sclera, and partially in the subconjunctival space, and the housing (208D) may be attached to a first end of the implant body. In this variation, the housing (208D) may be positioned in the sulcus.

As depicted in FIG. 2E, the implant body (202E) of the intraocular implant (200E) may be positioned in a tissue (e.g., sclera) at an acute or obtuse angle. The implant body (202E) may comprise one or more (e.g., two, three, four, or more) anchoring elements (204E) along the length of the implant bodies (202E). The anchoring elements (204E) may comprise crossbars or barbs. In use, the crossbars or barbs may be positioned within a tissue (e.g., sclera), on a first side of the tissue (e.g., sclera), and/or on a second side of the tissue. In some variations, the crossbars or barbs are positioned on a first side of the tissue and within the tissue. The implant body may be angled within a tissue to prevent the implant body from moving within or out of the tissue.

As depicted in FIG. 2F, the implant body (202F) of the intraocular implant (200F) may comprise a coil. The coil may comprise a lumen or cavity partially or fully therethrough, or may be solid. In variations comprising a lumen or cavity (e.g., may be hollow), one or more drugs may be contained within the lumen or cavity of the coil and/or all or a portion of a coil may be coated with a drug-eluting matrix containing one or more drugs. The coiled implant body (202F) may be positioned within a tissue (e.g., sclera). In some variations, a first end of the coiled implant body (202F) may be positioned on a first side of a tissue (e.g, sclera), and a second end of the coiled implant body (202F) may be positioned on a second side of the tissue. In some variations, a first end of the coiled implant body (202F) may be positioned on a first side of a tissue (e.g., sclera), and a second end of the coiled implant body (202F) may be positioned within the tissue.

FIG. 2G depicts an intraocular implant (200G) comprising an implant body (202G) in the form of a filament or suture. In some variations, all or a portion of the implant body (202G) may be coated with or may comprise a drug-eluting matrix containing one or more drugs. In some variations, the intraocular implant (200G) may comprise one or more anchoring elements (204G) (e.g., a bead, a knot). The anchoring elements may be positioned anywhere along the length of the implant body and in some variations, such as those comprising knot anchoring elements, the knots may be formed from the implant body itself (e.g., may be knots formed in the suture or filament at one or more locations along its length). In use, the anchoring elements may be positioned along a length of the implant body (202G) between a first end of the implant body and the sclera, along a length of the implant body (202G) within the sclera, along a length of the implant body (202G) between the sclera and a second end of the implant body (202G), or any combination thereof.

FIGS. 2H-2J depict intraocular implants (200H-200J) comprising implant bodies in the form of filaments or sutures. The intraocular implants (200H-200J) each further comprise a housing (208H-208J) coupled to the implant body (202H-202J). One or more drugs may be contained within the housings (208H-208J) coupled to the implant bodies (202H-202J) (e.g., within a reservoir in the housing, within a drug-eluting matrix within the housing). In some variations, all or a portion of the housings (208H-208J) may be coated with a drug-eluting matrix containing one or more drugs. FIG. 2H depicts an intraocular implant (200H) with the implant body (202H) residing partially in the sulcus, partially in the sclera, and partially in the subconjunctival space. The housing (208H) is attached to a first end of the implant body (202H) such that the longitudinal axes of the housing (208H) and the implant body (202H) are parallel. FIG. 2I depicts an intraocular implant (200I) with the implant residing partially in the sulcus, partially in the sclera, and partially in the subconjunctival space. The housing (208I) is attached to a first end of the implant body (202I) such that the longitudinal axis of the housing (208) is transverse (e.g., perpendicular) to the longitudinal axis of the implant body (202I). FIG. 2J depicts an intraocular implant (202J) with the second end of the implant body (202J) residing entirely in the sclera and a first end of the implant body (202J) residing in the sulcus. The housing (208J) is attached to a first end of the implant body (202J) such that the longitudinal axis of the housing (208J) is transverse to the longitudinal axis of the implant body (202J). In some variations, the intraocular implants (202H-202J) may comprise one or more anchoring elements (e.g., a bead, a knot). The anchoring elements may be positioned anywhere along the implant body, including, when in use, along a length of the implant body (202H-202J) between the housing (208H-208J) and the sclera, along a length of the implant body (202H-202J) within the sclera, along a length of the implant body (202H-202J) between the sclera and a second end of the implant body (202H-202J), or any combination thereof.

Figures 3A, 3B, 3C, 3D:
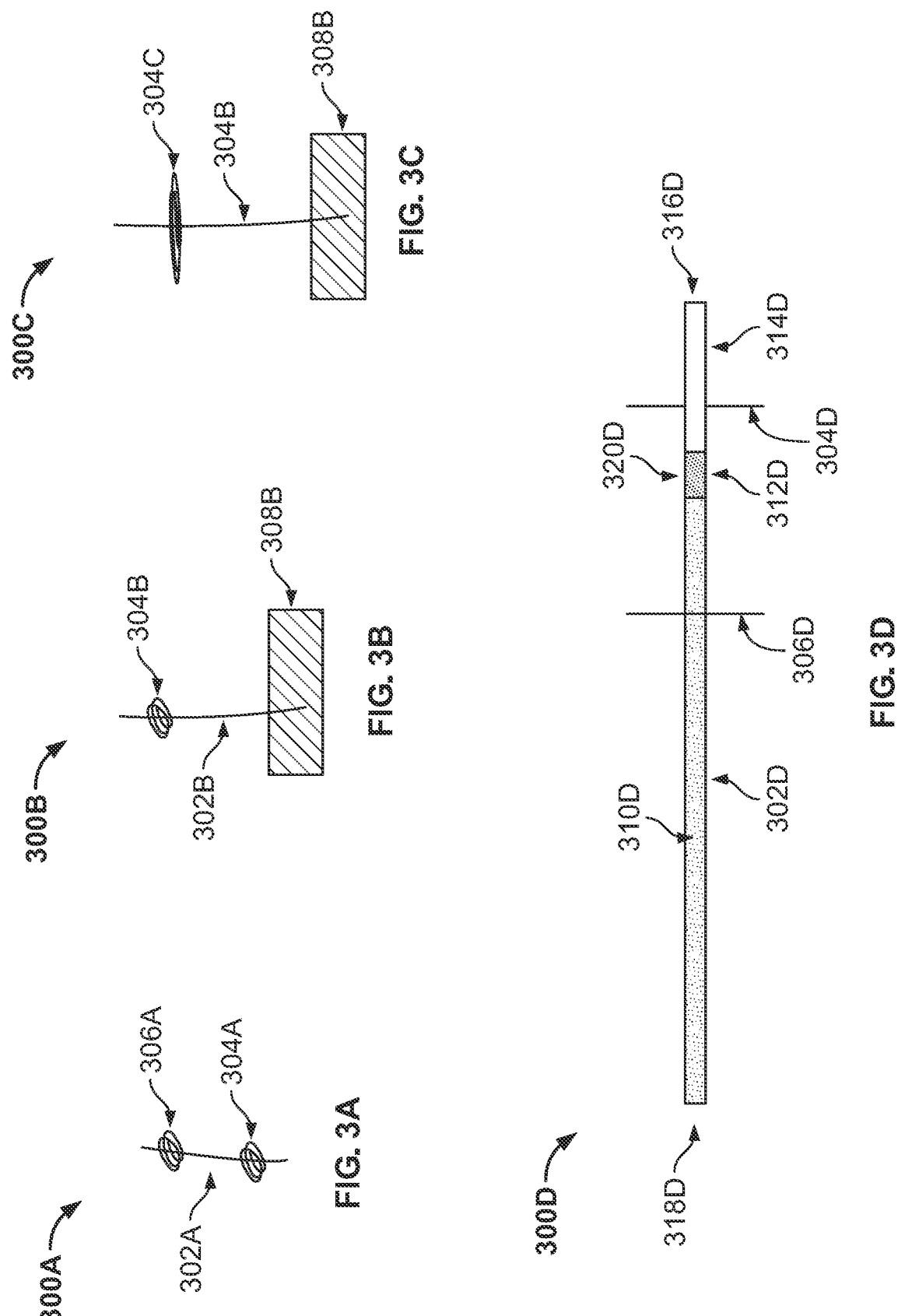
FIGS. 3A-3C show exemplary intraocular implants comprising different anchoring elements.
FIG. 3D shows an exemplary intraocular implant comprising a lumen and a drug reservoir.

FIG. 3A depicts an intraocular implant (300A) comprising an implant body (302A), a first anchoring element (304A) and a second anchoring element (306A). The first and second anchoring elements (304A, 306A) each comprise a knot or bead positioned at or near each end of the implant body (302A). In some instances, the first anchoring element (304A) (e.g., the anchoring element positioned at or near the first end of the implant body) may be erodible, while the implant body (302A, 302B, 302C) and second anchoring element (306A) may be non-erodible. FIG. 3B depicts an intraocular implant (300B) comprising an implant body (302B), a first anchoring element (304B), and a housing (308B). The first anchoring element (304B) comprises a knot or bead positioned at or near the second end of the implant body (302B). The housing (308B) is positioned at or near the first end of the implant body (302B). FIG. 3C depicts an intraocular implant (300C) comprising an implant body (302C), a first anchoring element (304C), and a housing (308C). The first anchoring element (304C) comprises a crossbar (which may be formed from, e.g., a suture or a filament) positioned at or near the second end of the implant body (302C). The housing (308C) is positioned at or near the first end of the implant body (302C). In FIGS. 3A, 3B, and 3C, the anchoring element (304A, 304B, 304C) is positioned in the subconjunctival space (knot or bead, and filament, respectively), and a housing (308B or 308C), which may, in this variation, also serve to anchor the intraocular implant in addition to deliver drug, is positioned in the sulcus.

FIG. 3D shows another variation of an intraocular implant. As shown there, the intraocular implant (300D) may comprise an elongate implant body (302D) comprising a lumen (310D) at partially therethrough, a stopper (312D), a cavity (314D) containing a drug, a solution of a drug, a slurry of the drug, an emulsion of the drug, or a drug-eluting matrix, a first end (316D) and a second end (318D). The cavity (314D) may be positioned at or near the first end (316D) of the implant body (302D) and the first end (316D) may be fully or partially open to allow delivery of the drug in the cavity to the eye. The second end (318D) may also be fully or partially open to allow passage of a delivery device (e.g., a guidewire) into the lumen (310D) of the elongate implant body (302D).

A stopper (312D) may be positioned between the lumen (310D) and the cavity (316D) containing the drug, and may be configured to assist in delivery of the implant using the delivery device. For example, in some variations, the stopper (312D) may be solid. The stopper (312D) may be formed integrally with the elongate implant body (302D), or may be formed separately and positioned within the lumen (312D) of the implant body (302D) to form an end of the lumen (320D). In some variations, the stopper (312D) may directly separate the lumen (310D) and the cavity (314D). In some variations, the elongate implant body (302D) may comprise a single lumen entirely therethrough, which may be formed into the lumen (310D) and the cavity (314D) by placement of the stopper (312D) within the single, through body lumen.

Thus, in some variations, the diameters of the lumen (310D) and the cavity (316D) may be the same. In other variations, the diameter of the lumen (310D) may be larger than or smaller than the diameter of the cavity (316D). The solid stopper (1312D) between the first and second hollow ends of the elongate implant body allows for contact with a delivery device or a portion of a delivery device. In some embodiments, a guidewire or pusher makes contact with the stopper during advancement and/or positioning of the implant within the eye. In some variations, the elongate implant body (302D) may comprise polymer (e.g., nylon or polypropylene) and/or may be in the form of a filament or suture.

The intraocular implant (300D) may further comprise anchoring elements (304D and 306D). The anchor elements (304D and 306D) may be positioned on either side of the stopper (e.g., proximal to and distal to the stopper). In some variations, one or more anchoring elements (304D and 306D) may be aligned with the cavity (314D) containing the drug (e.g., the anchoring element may be positioned along the implant body (302D) at a location in which the implant body (302D) contains drug therein). In some variations, the anchoring elements (304D and 306D) may comprise expandable arms, which may serve as crossbar anchoring elements. The expandable arms may be configured such that they expand during or after implantation of the elongate implant body, and may be configured to prevent the elongate implant body from significantly moving relative to (e.g., back through) the sclera.

FIGS. 4A-4E show exemplary variations of intraocular implants (400A-400E) comprising implant bodies (402A, 402B, 402C, 402D, 402E) with housings (408A, 408B, 408C, 408D, 408E) comprising a drug coupled to an end thereof. FIG. 4A shows a housing (408A) comprising a reservoir containing a drug. FIG. 4B shows a housing (408B) comprising fenestrations in a sidewall thereof for controlled release of a drug contained therein. FIG. 4C shows a housing (408C) in the form of a cage. The cage contains a reservoir comprising the drug. FIG. 4D shows a housing (408D) with an internal surface coated with or containing a drug. FIG. 4E shows a housing (408E) with an external surface coated with a drug.

As described in more detail herein, the intraocular implant devices may comprise a reservoir containing a drug. The reservoir containing the drug may be attached directly to the implant body, may be positioned within the implant body, or may be positioned within a housing coupled to the implant body. Reservoirs can take many forms, including but not limited to, blisters, balloons, or cylinders, which may themselves be removable and replaceable. In some embodiments, a reservoir may comprise one or more delivery ports through which a drug may be injected. Thus, the intraocular implants described herein may be refillable. Exemplary reservoirs (522A, 522B, 522C, 522D, and 522E) suitable for use in or with the disclosed implants are highlighted in FIGS. 5A-5E. FIG. 5A depicts a blister or balloon reservoir (522A) configured to receive a drug injected directly therein. In some variations, the reservoir may be refilled once or multiple times, e.g., by multiple injections. FIG. 5B depicts a blister or balloon reservoir (522B) with a port (524B), flush with the surface of the reservoir, for receiving a drug within the reservoir (522B) by injection or similar means. FIG. 5C depicts a reservoir (522C) with a port (524C) extending from the surface of the reservoir that can dock with a refilling needle. FIGS. 5D and 5E show cylindrical reservoirs (522D, 522E).

Exemplary Implant Locations

Figure 7:
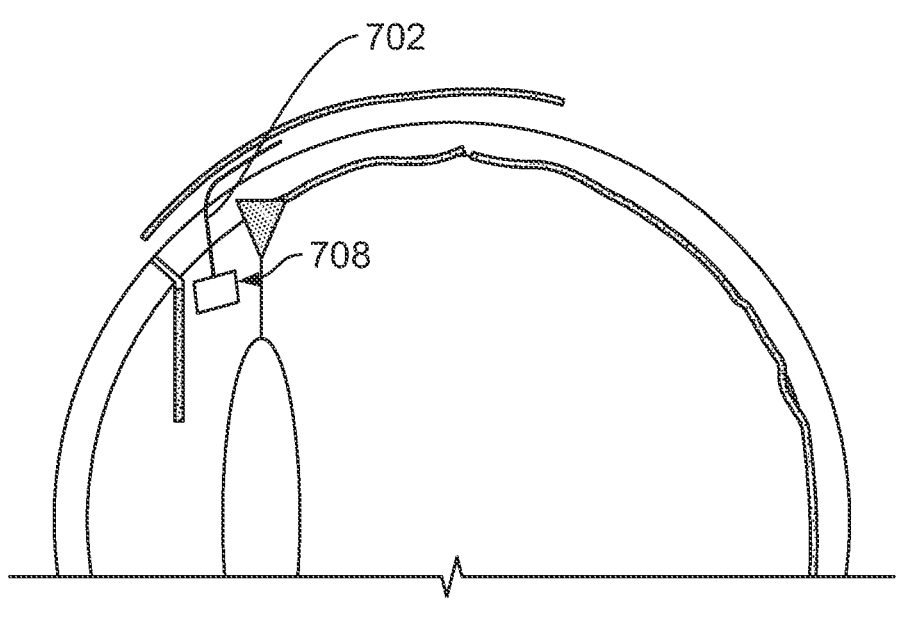
FIG. 7 shows an exemplary intraocular implant with a drug-eluting reservoir or housing positioned in the sulcus and a second end positioned in the subconjunctival space.
Figure 8:
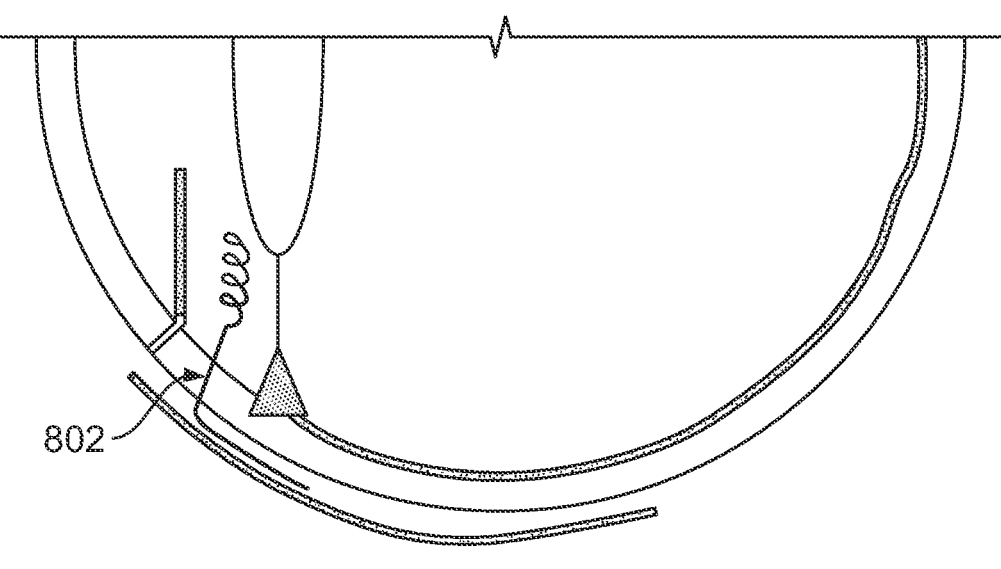
FIG. 8 shows another exemplary intraocular implant with a first end positioned in the sulcus and a second end positioned in the subconjunctival space.
Figure 9:
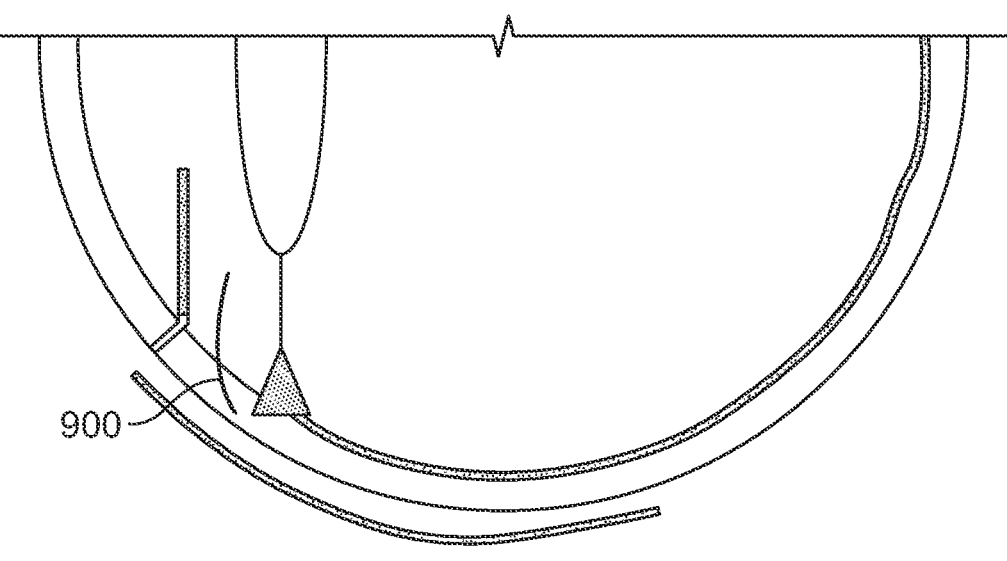
FIG. 9 shows an exemplary intraocular implant with a first end positioned in the sulcus and a second end positioned entirely in the sclera.

As discussed in detail herein, the intraocular implants may be configured to be advanced into the eye and positioned to deliver drug to various portions of the eye. For example, in some variations, the intraocular implants may be configured to be positioned at least partially in a tissue of the eye. In some instances, the intraocular implant may be positioned at least partially within the sclera (104). FIGS. 6-11 depict exemplary locations for the intraocular implants described herein within the eye. FIG. 9 depicts an intraocular implant (900) comprising an implant body configured to be advanced into the eye through the sclera and positioned such that the second end of the implant body is positioned entirely within the sclera.

In certain embodiments, the intraocular implants may be positioned within the eye such that one end of the implant (e.g., a non-drug-eluting end) is outside of the sclera, while the other end of the implant (e.g., a drug-eluting end) is positioned within the sulcus. FIGS. 2A-2J depict intraocular implants with implant bodies (202A-202J) positioned at least partially in the sclera. In some embodiments, the second end of the implant body may be configured to be positioned in the subconjunctival space.

Figure 6:
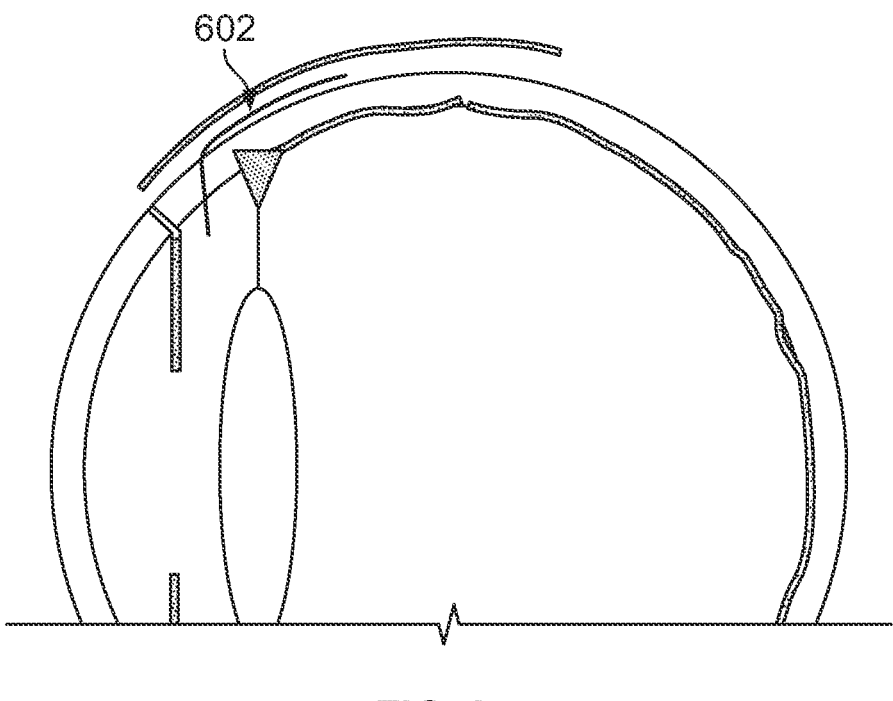
FIG. 6 shows an exemplary intraocular implant with a first end positioned in the ciliary sulcus, an extension of the posterior chamber, and a second end positioned in the subconjunctival space.
Figure 16:
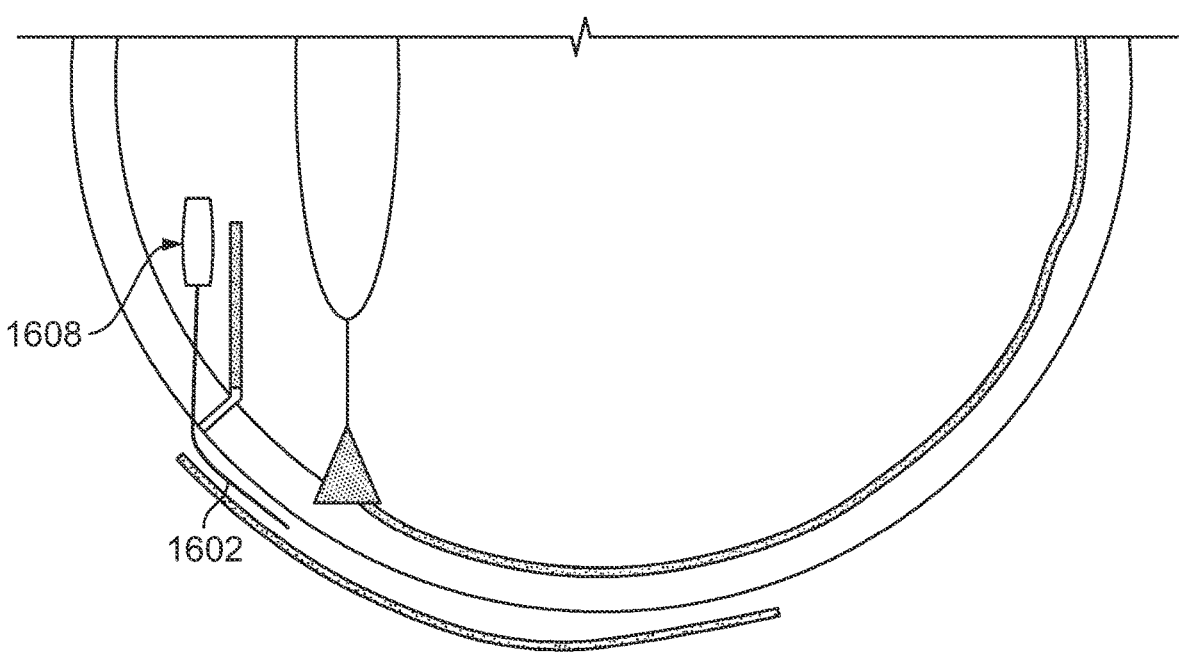
FIG. 16 shows an exemplary implant body traversing the cornea with a drug-eluting reservoir or housing positioned within the anterior chamber.

In some embodiments, an intraocular implant may comprise an implant body, where the first end of the implant body is positioned in the sulcus or anterior chamber and the second end of the implant body is positioned in the subconjunctival space. This is depicted in FIG. 6. In certain embodiments, an intraocular implant may comprise an implant body, where the first end of the implant body comprises a drug-eluting reservoir or housing and may be positioned in the sulcus, and where the second end of the implant body may be positioned in the subconjunctival space. An example of this is depicted in FIG. 7, which shows an implant body (702) traversing the sclera, where the drug-eluting reservoir or housing (708) is positioned within the sulcus of the posterior chamber. FIG. 16 depicts an implant body (1602) traversing the cornea, where the drug-eluting reservoir or housing (1608) is positioned within the anterior chamber.

Figure 17:
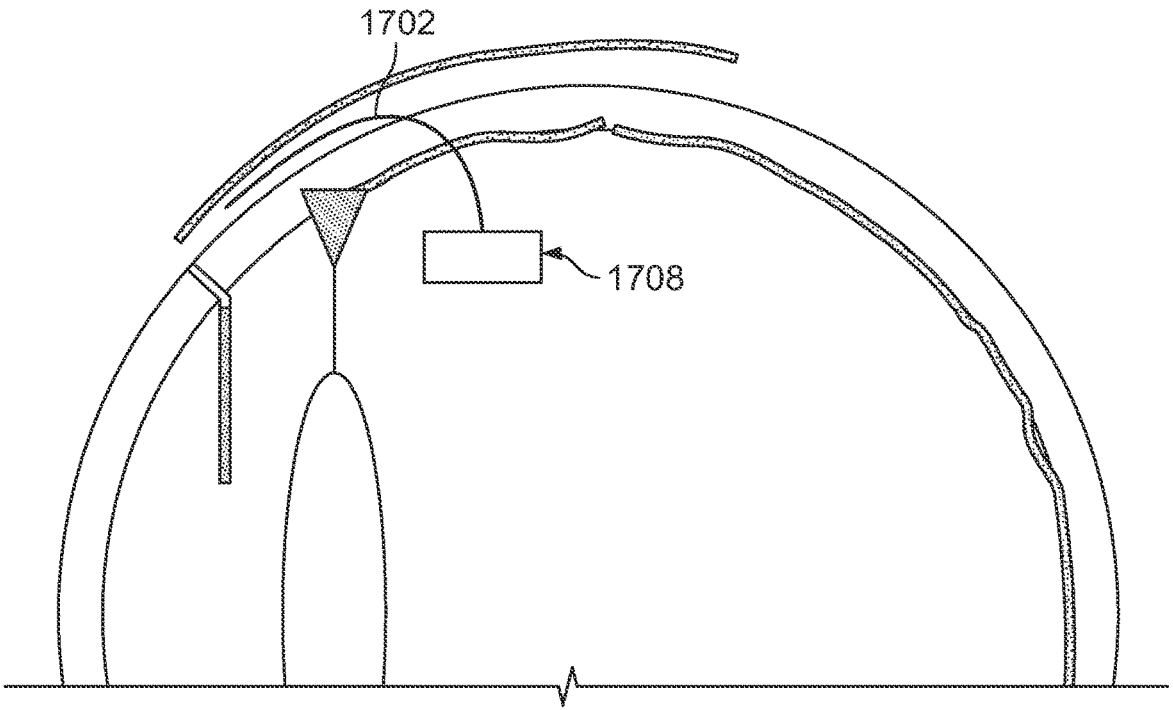
FIG. 17 shows an exemplary intraocular device with an implant body traversing the sclera and a drug-eluting reservoir or housing positioned within the vitreous.

In some embodiments, an intraocular implant may comprise an implant body, where the first end of the implant body is positioned in the vitreous and the second end of the implant body is positioned in the subconjunctival space. In certain embodiments, an intraocular implant may comprise an implant body, where the first end of the implant body comprises a drug-eluting reservoir or housing and may be positioned in the vitreous, and where the second end of the implant body may be positioned in the subconjunctival space. This is depicted in FIG. 17, where the implant body (1702) transverses the sclera, and the drug-eluting reservoir or housing (1708) is positioned within the vitreous.

Figures 18, 19:
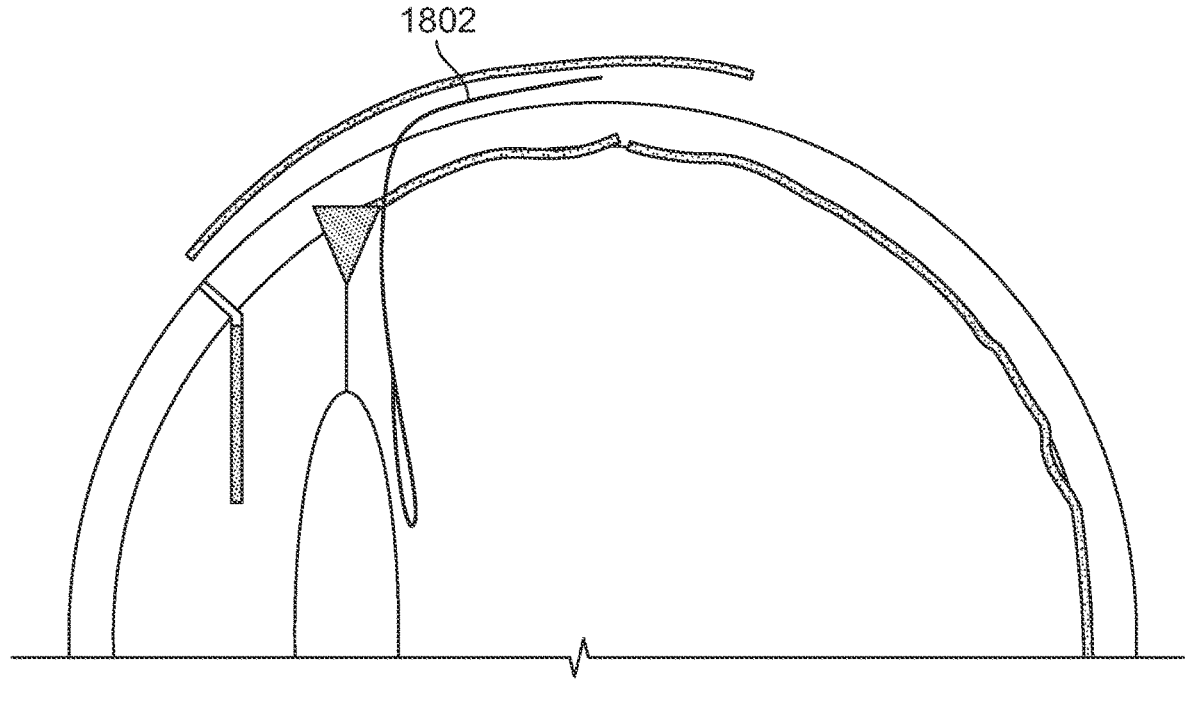
FIG. 18 shows an exemplary spherical intraocular device with an implant body traversing the sclera, where the first end of the implant body resides in Berger's Space.
FIG. 19 shows an exemplary spherical intraocular device with an implant body traversing the sclera, where the first end of the implant body resides in the Petit's Canal.

In some embodiments, an intraocular implant may comprise an implant body, where the first end of the implant body is positioned in Berger's space or the Canal of Petit, and the second end of the implant body is positioned in the subconjunctival space. FIG. 18 depicts an implant body (1802) traversing the sclera, where the first end of the implant body (1802) resides in Berger's Space. FIG. 19 depicts an implant body (1902) traversing the sclera, where the first end of the implant body (1902) resides in the Canal of Petit.

In certain embodiments, an intraocular implant may comprise an implant body, where the first end of the implant body comprises a coil and is positioned in the sulcus, and where the second end of the implant body is positioned in the subconjunctival space. An example of this is depicted in FIG. 8, which shows an implant body (802) traversing the sclera, where the first end of the coiled implant body is positioned in the sulcus). In some embodiments, an intraocular implant may comprise an implant body, where the first end of the implant body is positioned in the sulcus and the second end of the implant body is positioned entirely in the sclera. FIG. 9 depicts an implant body (900) positioned in the sclera and the sulcus, with the second end of the implant body (900) residing inside the sclera and the first end of the implant body (900) residing in the sulcus.

Figure 10:
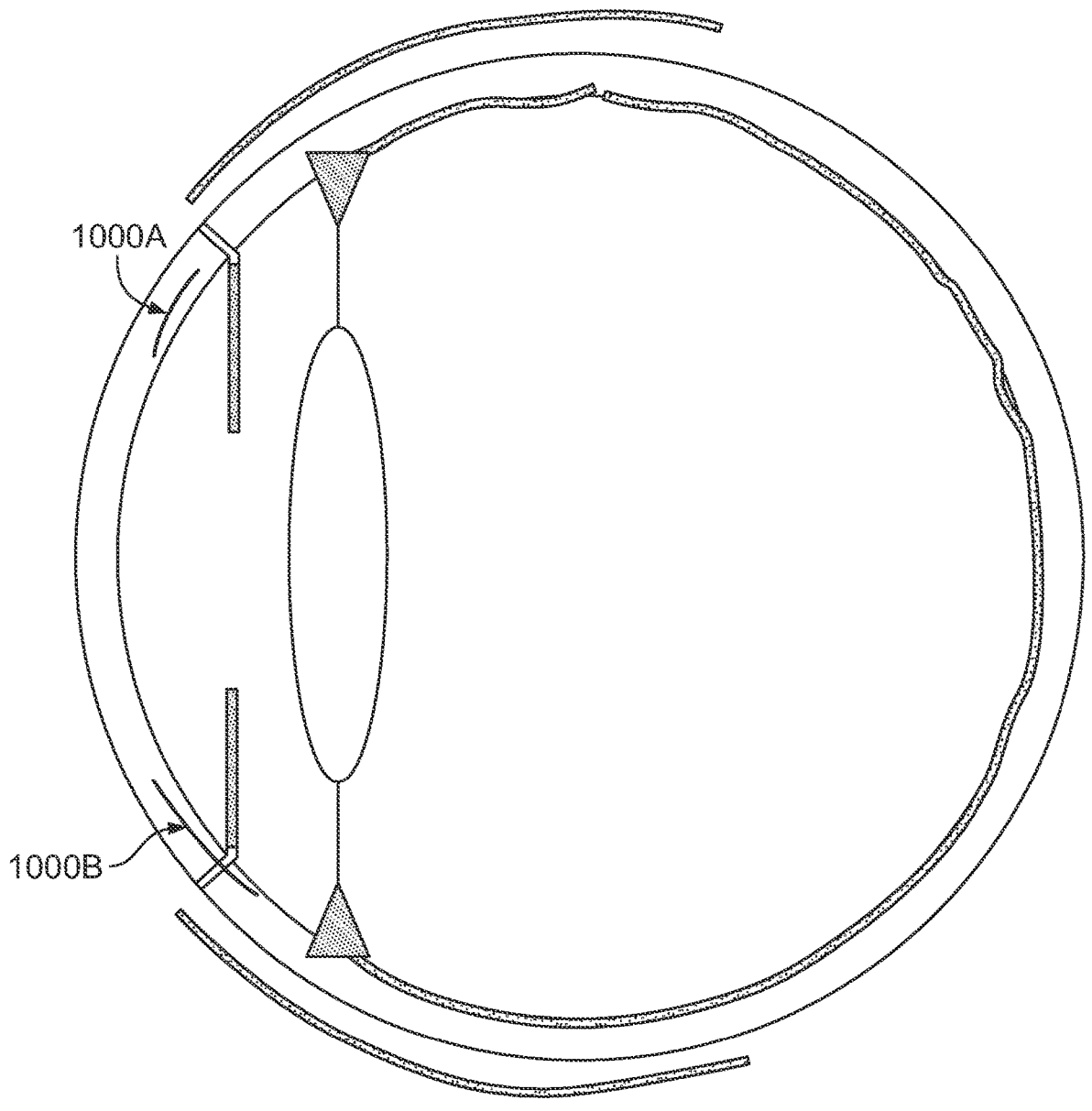
FIG. 10 shows an exemplary intraocular implant positioned entirely in the sclera and an exemplary intraocular device positioned entirely in the cornea, limbus, and sclera.

Also described herein are intraocular implants that are configured to be positioned intramurally in one or more of the sclera, the cornea, and the limbus. In certain variations, the implant body may reside fully within the cornea, with a first end and a second end residing in the cornea. In certain variations, the implant body may reside partially within the limbus, with a first end residing in the cornea and a second end residing in the sclera. In certain variations, the implant body may reside partially within the limbus, with a first end residing in the sclera and a second end residing in the cornea. These arrangements are depicted in FIG. 10, where a first implant body (1000A) is positioned entirely in the cornea and a second implant body (1000B) is positioned partially in the limbus, with one end residing in the cornea and one end residing in the sclera.

Figure 21:
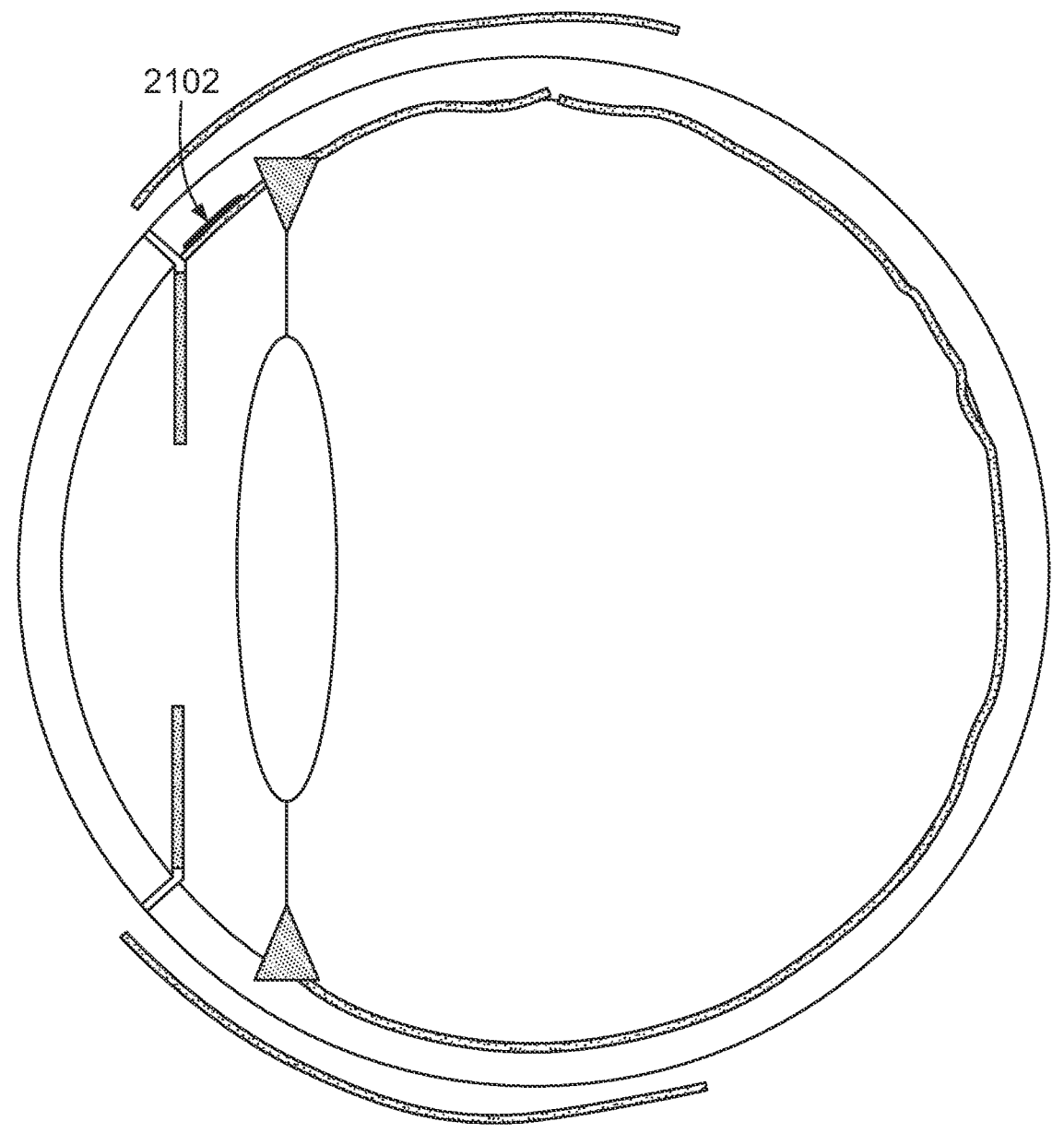
FIG. 21 shows an exemplary intraocular implant residing fully within the suprachoroidal space.
Figure 22:
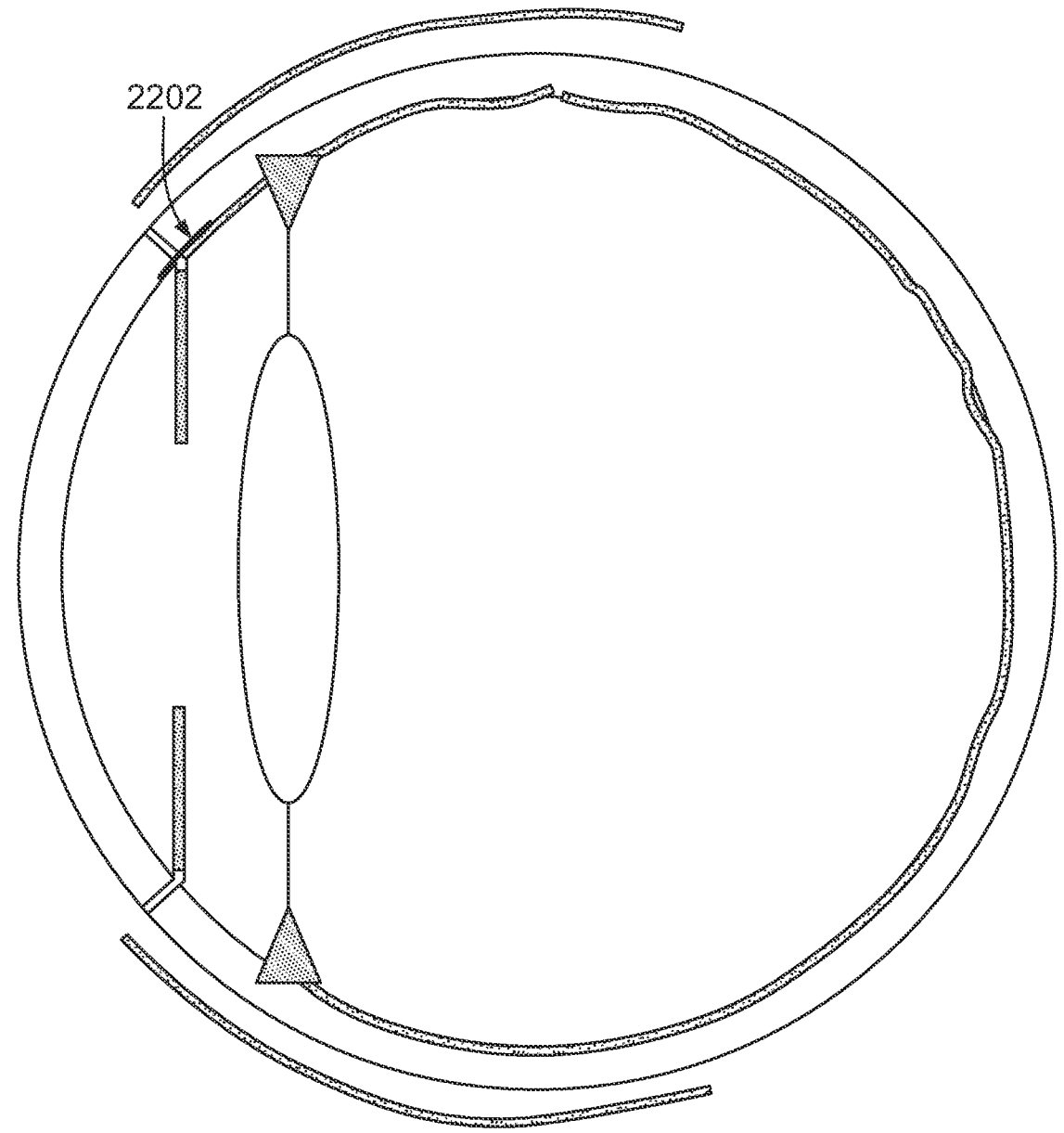
FIG. 22 shows an exemplary intraocular implant residing partially within the suprachoroidal space, where the first end resides in the anterior chamber.

Also described herein are intraocular implants that are configured to be positioned partially or fully within the suprachoroidal space. FIG. 21 depicts an intraocular implant comprising an implant body (2102), where the intraocular implant resides fully in the suprachoroidal space. FIG. 22 depicts an intraocular implant comprising an implant body (2202) positioned partially in the suprachoroidal space and partially in the anterior chamber. In particular, one end of the implant body (2202) resides in the suprachoroidal space and the other end resides in the anterior chamber.

Figure 11:
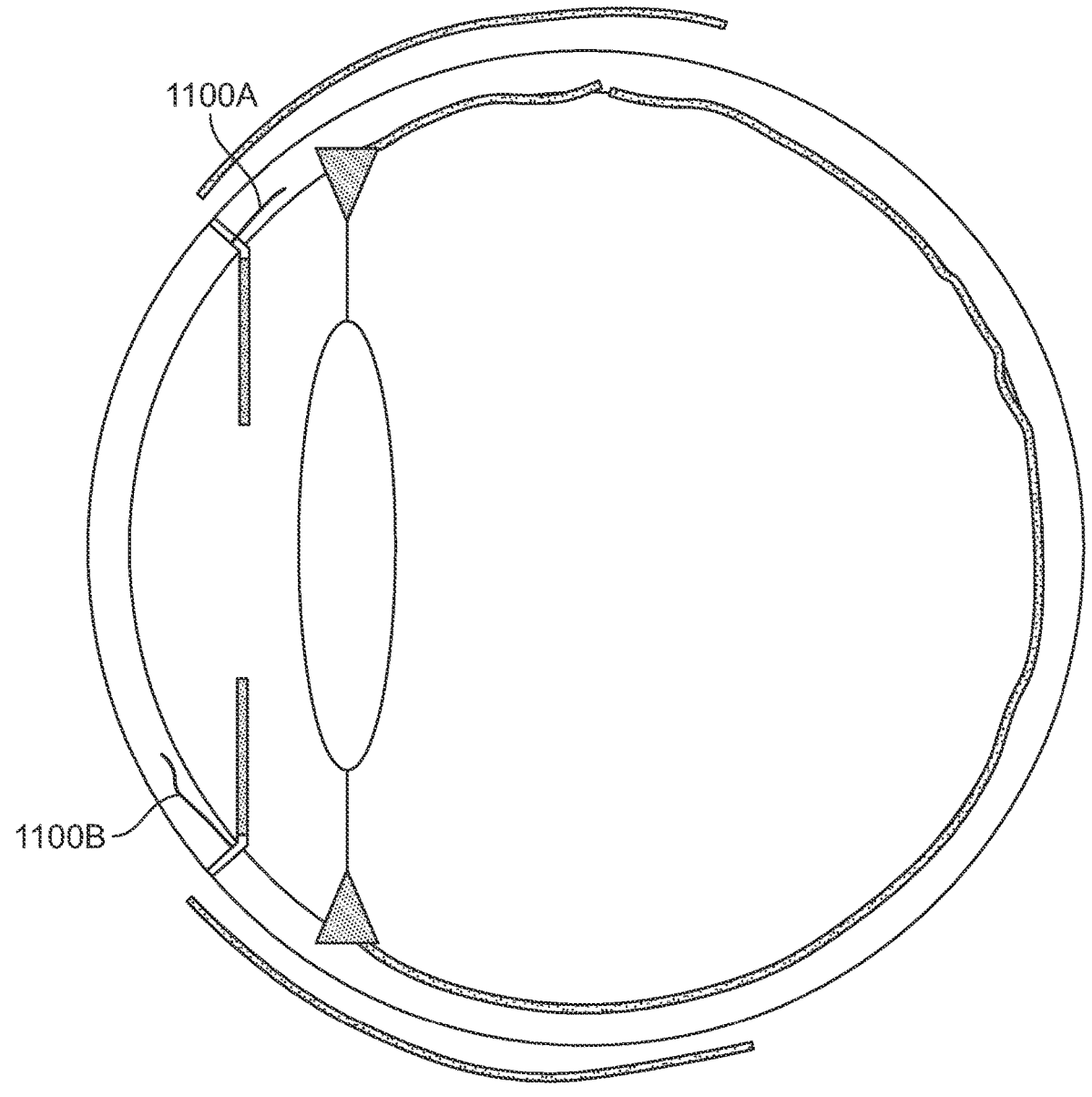
FIG. 11 shows an exemplary intraocular implant positioned entirely in the limbus and cornea and an exemplary intraocular implant positioned entirely in the limbus and sclera
Figure 20:
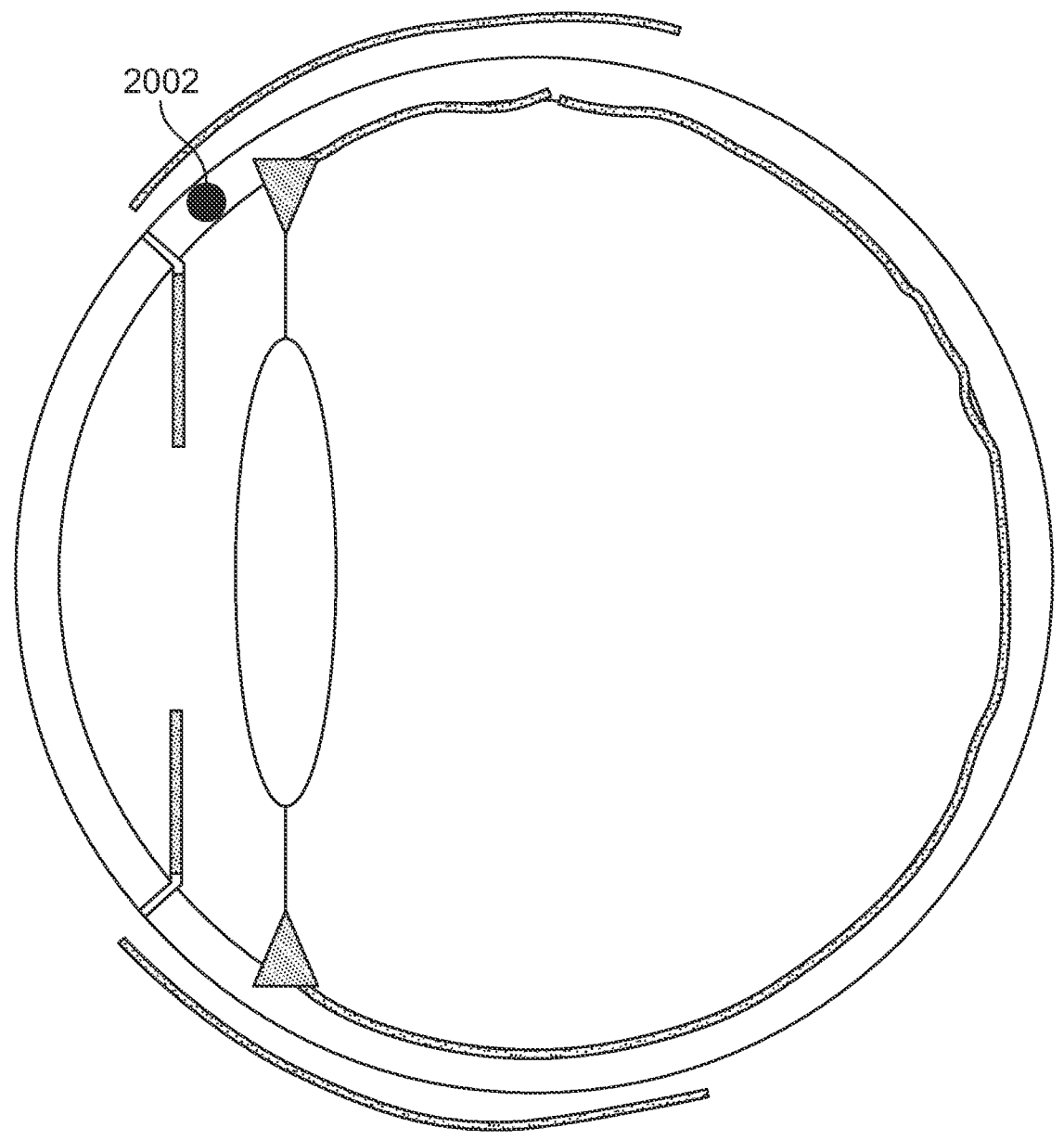
FIG. 20 shows a spherical implant body residing fully within the sclera.

In certain variations, the implant body may reside fully intramurally, with a first end residing in the limbus and a second end residing in the sclera. In certain variations, the implant body may reside fully intramurally, with a first end residing in the sclera and a second end residing in the limbus. Such configurations are depicted in FIG. 11, which depicts a first implant body (1100A) residing partially in the sclera and partially in the limbus. In certain variations, the implant body may reside fully intramurally, with a first end residing in the limbus and a second end residing in the cornea. In certain variations, the implant body may reside fully intramurally, with a first end residing in the cornea and a second end residing in the limbus. Such configurations are also depicted in FIG. 11, which also depicts a second implant body (1100B) residing partially in the cornea and partially in the limbus. In some variations, the implant body may be spherical, spheroid, or ovoid and may reside intramurally, such as fully in the sclera. FIG. 20 depicts an intraocular implant comprising a spherical implant body (2002), where the intraocular implant resides fully in the sclera.

Intraocular implants of this type may release the drug directly into the intramural tissue (e.g., a wall of tissue in the eye), where it will diffuse through the intramural tissue to ultimately reach the site of disease. In some cases, the drug diffuses into the uvea, retina, anterior chamber or the posterior chamber. For example, an intramural implant may elute or otherwise deliver a drug (e.g., bimatoprost, latanoprost) into the tissue of the eye, and the drug may dissolve by diffusion into the anterior segment of the eye or uveoscleral tissue, where it may act to reduce a symptom of a condition of the eye or treat a condition of the eye (e.g., lower intraocular pressure). In another example, an intramural implant may elute or otherwise delivery a drug (e.g., dexamethasone) into the tissue of the eye and the drug may diffuse into intraocular spaces (e.g., posterior chamber). In this example, at least some of the drug may ultimately reach the retina, where it may act to reduce a symptom of a condition of the eye or treat a condition of the eye (e.g., reduce macular edema in diabetes or after vein occlusion). In some cases, the intramural implants may be well suited to deliver low-molecular weight drugs (e.g., prostaglandins), which may diffuse quickly through the intramural tissue (e.g., sclera) to a target location in the eye (e.g., anterior or posterior chamber). Higher-molecular weight (e.g., 10 kDa to 200 kDa, or 10 kDa to 500 kDa) drugs (proteins, antibodies) may also diffuse through a mural tissue, although at a lower rate. Administration of higher-molecular weight drugs via the implants described herein to an intramural tissue may result in diffusion to the anterior or posterior chamber. In some variations, an implant (e.g., and intramural implant) may elute drug to the ocular surface (e.g., subconjunctival space, or exterior surface of the eye).

For intramural implantation, the implant body can take a number of forms. For instance, the implant body may comprise a sphere, spheroid, ovoid, rod, filament, or capsule, any of which, may, in some variations, comprise an interior chamber. In some variations, the implant body may comprise a sheet.

It should be appreciated that any of the intraocular implants described herein may be positioned in any of the anatomical locations/positions described herein.

Delivery Devices

Also described herein are delivery devices configured to house the intraocular implants during advancement and to position the intraocular implants at the desired location within the eye of a subject. The delivery devices described herein may be single-handed, single-operator controlled devices such that a user may deliver the intraocular implants described herein without assistance. A delivery device described herein may deliver a drug (e.g., as a solid, liquid, emulsion) directly into a tissue of the eye, alternatively or in addition to an implant.

Figures 12, 13:
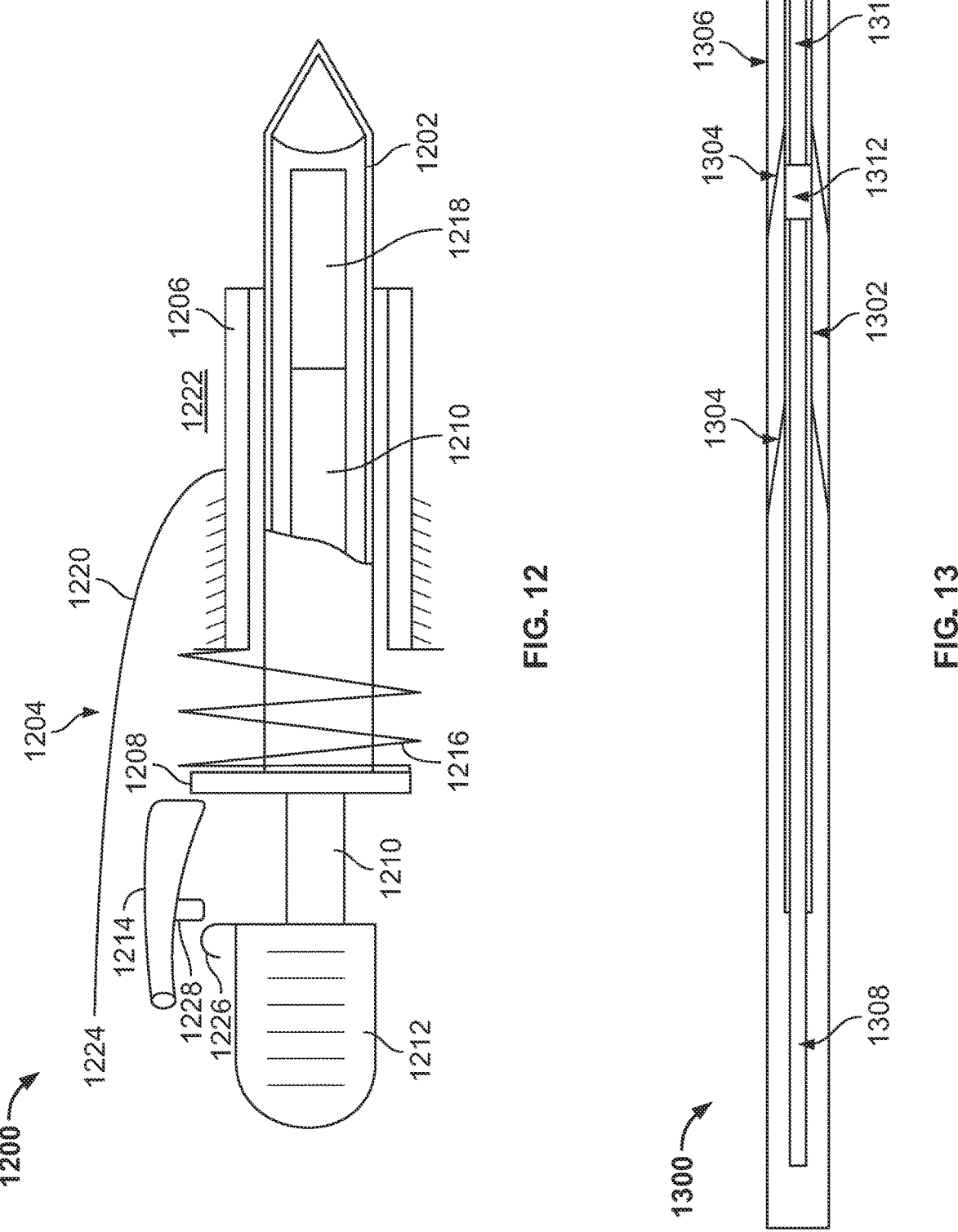
FIG. 12 is a cross-sectional view of an exemplary delivery device used to deliver an intraocular implant into the eye of a subject.
FIG. 13 shows an exemplary intraocular device delivery device.

FIG. 12 is a cross-sectional view of an exemplary ocular delivery device with an intraocular implant positioned therein. As shown there, the delivery device (1200) may comprise a cannula (1202) coupled to a handle (1204). The delivery device (1200) may further comprise a tissue stop (1206) coupled to the handle (1204) and slideably coupled to the cannula (1202). In some variations, the tissue stop (1206) may be positioned around the cannula (1202). For example, the tissue stop (1206) may comprise a tube with a lumen therethrough, and the cannula (1202) may be slideably positioned within the lumen of the tissue stop or housing (1206). The handle (1204) may comprise a pusher or push rod (1210), an actuator (1212) (e.g., a slider, a button, a knob, or the like) for the push rod, a spring (1216), a spring stop (1208) and a spring actuator (1214). The spring (1216) may be coupled between the spring stop (1208) and the tissue stop (1206). The handle (1204) may comprise a grip portion and a housing (1220) comprising a proximal end (1222) and a distal end (1224). In some variations, the grip portion may be raised, depressed, grooved, or otherwise textured in certain areas, which may assist a user in holding the handle during an implantation procedure and/or may improve user comfort. The cannula may be slideably coupled to and may extend from, the distal end (1224) of the housing (1220). The tissue stop (1206), which may be configured to assist a user in properly positioning the intraocular implant and in controlling penetration depth of the implant, may also be coupled to the housing (1220), and may allow the cannula (1202) to slideably move within the housing (1220). As mentioned above, the delivery device (1200) may comprise a push rod actuator (1212), which may be fixedly coupled to the push rod (1210) to advance the push rod (1210) relative to the cannula (1202) (and tissue stop (1206)) and release the implant (1218) from the delivery device (1200). The delivery device (1200) may also include a spring actuator (1214), which may be releasably coupled to the spring (1216) via the spring stop (1208), and releasably engaged with the push rod actuator (1212). The spring (1216) may initially be in a compressed configuration, and may be sandwiched between the spring stop (1208) and the tissue stop (1206) or a portion of the handle housing (1220). For example, a first end of the spring may be fixedly coupled to the spring stop (1208) and a second end of the spring may be fixedly coupled to the tissue stop (1206) (as depicted) or a portion of the handle housing (1220). When the push rod actuator (1212) is advanced or otherwise deployed, a portion of the push rod actuator (1212) may contact a portion of the spring actuator (1214), which may release the spring (1216) from the compressed position, thereby retracting the spring stop (1208) and the cannula fixedly coupled thereto (1202). For example, prior to implantation, the spring actuator (1214) may be in an engaged position, in which it constrains the movement of the spring (1216). Upon advancement of the push rod (1210) via the push rod actuator (1212), a first engagement feature (e.g., projection or protuberance) (1226) on the push rod actuator (1212) may contact a second engagement feature (e.g., projection or protuberance) (1228) on the spring actuator (1214), which may push or otherwise displace the spring actuator (1214) from the engaged position to a disengaged position in which the spring actuator (1214) no longer constrains the position of the spring stop (1208). When the spring actuator (1214) is moved from the engaged position to the disengaged position, energy stored in the spring (1216) is released, and the spring (1216) lengthens, pushing the spring stop (1208) and, thus the cannula (1202) fixedly attached thereto, proximally (away from the implant (1218)). In addition to disengaging the spring actuator (1214), advancement of the push rod actuator (1212) advances the push rod (1210) relative to the cannula (1202), thereby pushing the implant (1218) positioned within a lumen of the cannula (1202) out of the delivery device and delivering the implant (1218) to the eye. In this manner, the delivery device (1220) may be configured to simultaneously or approximately simultaneously deliver the implant (1218) and retract the cannula (1202) relative to the handle housing (1220). The delivery device may be configured for delayed delivery of the implant.

Accordingly, to deliver the implant to the eye, the delivery device (1200) with the implant (1218) preloaded therein may be advanced to a desired location within the eye with the cannula in an extended position by advancing the handle housing (1220). The tissue stop (1206) may be placed against tissue (e.g., sclera) at or near a target location, and the actuator (1212) may be advanced or otherwise activated (e.g., pressed, turned, etc.), thereby advancing the push rod (1210) and disengaging the spring actuator (1214). Upon disengagement of the spring actuator (1214), the spring (1216) may lengthen, retracting the cannula (1202) while the implant (1218) is delivered to the target location. After the energy in the spring (1216) has been released and the spring (1216) has lengthened, the cannula (1202) may be in a retracted position. The delivery device (1200) may then be withdrawn from the eye with the cannula in the retracted position, leaving the implant (1218) behind.

The cannula (1202) may be configured to provide easy and minimally traumatic access to a mural tissue (i.e., the sclera, the limbus, the cornea), or to the sulcus via the sclera. Cannulas in the delivery devices described herein may comprise distal tips that are blunt, sharpened, tapered, or beveled. In some variations, the cannula may comprise a needle. In some variations, cannulas may comprise a cutting surface. The cannula may be made from any suitable material with sufficient stiffness to allow it to be advanced through the sclera or another mural tissue. For example, the cannula may be formed of a metal such as stainless steel, nickel, titanium, aluminum, or alloys thereof, or a polymer.

The spring (1202) may be formed of a metal, such as stainless steel, nickel titanium, aluminum, or alloys thereof. Alternatively, it may be formed from a plastic or polymer with suitable rigidity and elasticity. The spring (1216) may be attached to the spring stop (1208) and tissue stop (1206) or handle housing (1220) by any suitable means, such as, for example, by an adhesive, a fitting, welding, or the like.

The actuator (1212) may be configured to reversibly engage the spring actuator (1214) in any manner suitable for controlled and predictable release of the energy in the compressed spring (1216). For instance, the actuator (1212) may comprise a ratchet system such that a portion of the actuator (1212) may advance in discrete steps until reaching the spring actuator (1214), which may then be triggered. This configuration may provide a user with more control over the implantation procedure and greater predictability as to when the implant (1218) may be released from the cannula (1202). As mentioned herein, the actuator (1212) may comprise a slider, a knob, a button, or the like. The spring actuator (1214) may, for instance, comprise a cantilever arm. In some variations, the spring actuator (1214) may be configured to recompress the spring for implant removal.

Suitable markings, colorings, or indicators may be included on any portion of the device to help identify the location or position of the end of the cannula, tissue stop, the push rod, the intraocular implant, or any other element of the delivery device.

In some variations, a guidewire and cannula system may be used to deliver the intraocular implants described herein. For instance, FIG. 13 shows an exemplary intraocular implant delivery device (1300) comprising a cannula (1306) and a guidewire (1308). An intraocular implant may be positioned within the cannula (1306) and delivered to the eye using the guidewire (1308). For example, a hollow elongate implant body (1302) may be preloaded or otherwise positioned within the cannula (1306). The implant may comprise a solid stopper (1312) between the first and second hollow ends of the elongate implant body (1302). The solid stopper (1312) may provide a contact surface for the guidewire (1308), such that after advancement of the guidewire through the cannula (1306) and implant body (1302), the guidewire may contact the stopper (1312) to advance and/or position the implant. In this variation, the first end of the elongate implant body may comprise a lumen (1310), which may house a drug, a solution of a drug, or a drug-eluting matrix. The implant (1300) may additionally comprise collapsible anchoring elements (1304) that may expand upon insertion into the tissue and/or removal of the cannula (1306). It should be appreciated the cannula utilized in this delivery device may have any of the features of any of the cannulas described herein.

Figure 14:
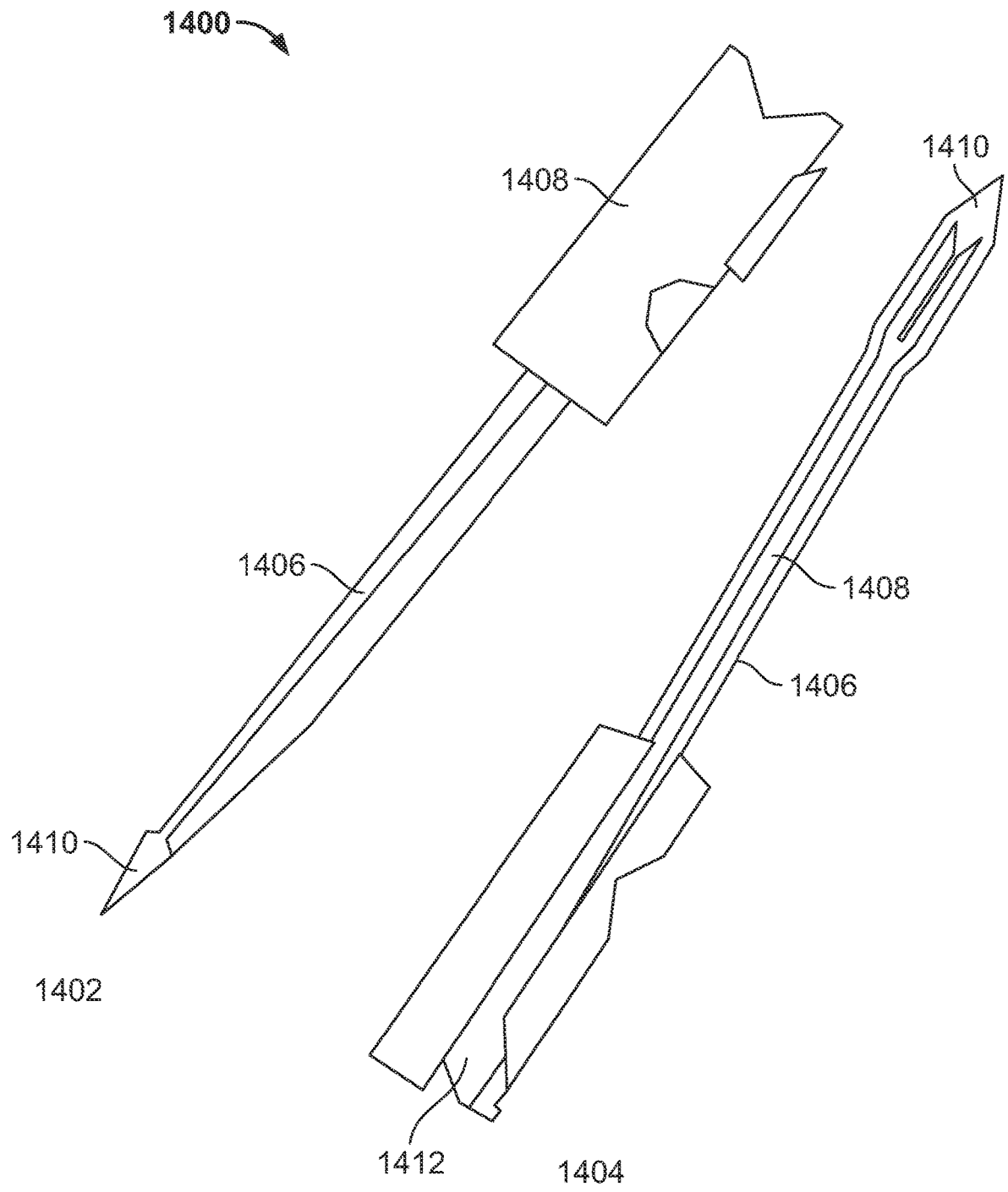
FIG. 14 shows another variation of an exemplary delivery device suitable for implanting intraocular devices.

FIG. 14 depicts posterior (1402) and anterior (1404) views of a variation of a delivery device (1400) suitable for delivering an intraocular implant described herein. The delivery device (1400) may comprise a cannula (1406) disposed within a handle (1408). The cannula (1406) may have a lumen (1408) running the length of the needle, configured for an intraocular implant to be delivered therethrough. The cannula (1406) may have a sharpened distal tip (1410). The cannula (1406) may have a longitudinal slot (1412) to facilitate positioning of an implant with a cap or anchoring element. The cannula (1406) may be made from any suitable material with sufficient stiffness to allow it to be advanced through the sclera or another mural tissue. For example, the cannula may be formed of a metal such as stainless steel, nickel, titanium, aluminum, or alloys thereof, or a polymer.

The human sclera ranges from approximately 0.4 mm to approximately 1 mm thick in various places, and the limbus is approximately 1.5 mm to approximately 2 mm thick. The delivery devices described herein may be configured to deliver an intraocular implant within this depth range. For instance, a guidewire used for delivering an intraocular implant described herein may be configured to deliver an intraocular implant to a depth of about 0.1 mm, about 0.2 mm, about 0.3 mm, about 0.4 mm, about 0.5 mm, about 0.6 mm, about 0.7 mm, about 0.8 mm, about 0.9 mm, or about 1.0 mm (including all values and sub-ranges therein) within an intramural tissue of the eye as measured from the external surface of the conjunctiva. The delivery devices described herein may push an implant in place to a specific tissue depth. A needle or cannula of a device described herein, or a needle or cannula separate from the devices described herein, may be used to create a scleral opening, and the intraocular implant may be delivered by a delivery device or system. Alternatively, a channeling instrument, similar to a corneal separator for intracorneal rings, or a femtosecond laser, may be used to create or prepare a tunnel, channel, or cavity for subsequent device implantation.

Further, as described above, and in the methods below, it may be beneficial to deliver an implant fully intramurally in the eye with at least a portion of the implant residing in a limbus, or an implant partially within a tissue and partially within a cavity of the eye. Precisely delivering the implant to a desired location is important in order to specifically target a treat certain tissues or structures of the eye.

Delivering the implant may be accomplished by advancing the implant into the eye using a delivery device described herein. The implant may be disposed within a cannula (e.g., a needle), and for instance, may be offset from the distal tip of a cannula so the operator of the delivery device knows the location of the implant within the eye during the implantation procedure, for instance, while advancing a cannula of the device. The implant may then be released from the delivery device in the proper location.

Precise delivery of an implant may be accomplished by positioning the implant (e.g., disposed within a delivery device) within the eye. In order to assist in such positioning, the delivery device or a portion thereof (e.g., a cannula) may be configured to visually indicate (e.g., via markings or indicators as described above) to a user how far to advance the delivery device to achieve a desired implant delivery depth (e.g., how far to advance the delivery device into the eye to achieve a particular implant placement within the eye). Additionally or alternatively, the relative position of the implant in the delivery device, in combination with the markings, or other individual indicators, can be adjusted depending on a combination of the length of the implant and the desired final positioning of the implant (e.g., fully in the limbus, partially in the limbus and partially in the sclera, partially in the limbus and partially in the cornea, etc.).

For example, in some variations, the implant may be positioned within a cannula of a delivery device such that the implant is offset from a distal tip of the cannula by a predetermined amount. The predetermined amount may correspond to the distance that the distal tip of the cannula is observed to advance into the anterior chamber during delivery. For instance, if the implant is disposed in a cannula 1.0 mm from the distal tip of the cannula, the operator of the delivery device may advance the distal tip of the cannula 1.0 mm or less into the anterior chamber. The cannula may be withdrawn to position the implant in the desired location. When the cannula is withdrawn, the implant thereby resides in a target tissue or structure of the eye (e.g., fully intramurally and does not protrude into the anterior chamber). In variations of the devices described herein, withdrawing the cannula comprises activating an actuator. In some variations, the actuator is coupled to the handle of a delivery device. Additionally or alternatively, the whole delivery device may be withdrawn without actuation of any additional component (e.g., a cannula with a guidewire is removed from the tissue of the eye in one motion). It should be appreciated that in some variations, the delivery device, or a portion thereof, does not extend into the anterior chamber of an eye.

Accordingly, the drug-eluting implant may be positioned for implantation within the delivery device at a desired distance from a distal tip of a cannula, depending on the length of the implant and/or the desired intramural location. For example, the implant may be disposed within a cannula at a distance from the distal tip of the cannula sufficient to allow implantation in the intramural tissue or tissues without protruding into the anterior chamber. In some variations of the devices and methods described herein, the implant (e.g., as measured by one end of an elongate implant body, or the central point of a sphere or spheroid) is disposed about 0.1 mm to 1 mm, about 0.2 mm to about 1 mm, about 0.3 mm to about 1 mm, about 0.4 mm to about 1 mm, about 0.5 mm to about 1 mm, about 0.6 mm to about 1 mm, about 0.7 mm to about 1 mm, about 0.8 mm to about 1 mm, about 0.9 mm to about 1 mm, about 0.1 mm to 0.9 mm, about 0.2 mm to about 0.9 mm, about 0.3 mm to about 0.9 mm, about 0.4 mm to about 0.9 mm, about 0.5 mm to about 0.9 mm, about 0.6 mm to about 0.9 mm, about 0.7 mm to about 0.9 mm, about 0.8 mm to about 0.9 mm, about 0.1 mm to 0.8 mm, about 0.2 mm to about 0.8 mm, about 0.3 mm to about 0.8 mm, about 0.4 mm to about 0.8 mm, about 0.5 mm to about 0.8 mm, about 0.6 mm to about 0.8 mm, about 0.7 mm to about 0.8 mm, about 0.1 mm to 0.7 mm, about 0.2 mm to about 0.7 mm, about 0.3 mm to about 0.7 mm, about 0.4 mm to about 0.7 mm, about 0.5 mm to about 0.7 mm, about 0.6 mm to about 0.7 mm, about 0.1 mm to 0.6 mm, about 0.2 mm to about 0.6 mm, about 0.3 mm to about 0.6 mm, about 0.4 mm to about 0.6 mm, about 0.5 mm to about 0.6 mm, about 0.1 mm to 0.5 mm, about 0.2 mm to about 0.5 mm, about 0.3 mm to about 0.5 mm, about 0.4 mm to about 0.5 mm, about 0.1 mm to 0.4 mm, about 0.2 mm to about 0.4 mm, about 0.3 mm to about 0.4 mm, about 0.1 mm to 0.3 mm, about 0.2 mm to about 0.3 mm, or about 0.1 mm to 0.2 mm from the distal tip of the cannula (including all subranges and values therein). In some variations, the implant is disposed about 0.1, 0.2, 0.3, 0.4, 0.5, 0.6, 0.7, 0.8, 0.9, 1.0 or greater mm from the distal tip of a cannula.

The delivery device may also be configured to directly interface with one or more tissues of the eye. For instance, the delivery device may be positioned such that it is applied to, and/or rests on, a surface (e.g., conjunctiva, sclera, cornea) of the eye near (e.g., above, superior to) the desired final implant location (e.g., intramural implant location). For example, a distal end of a cannula of a delivery device may be in contact with a tissue surface of the eye. In some embodiments, the delivery device may be positioned perpendicularly to a surface of the eye. In some variations, the delivery device may be angled relative to the surface of the eye (e.g., about 5, 10, 15, 20, 25, 30, 35, 40, 45, 50, 55, 60, 65, 70, 75, 80, or 85 degrees relative to the surface of the eye).

Methods of Treating Conditions of the Eye

Methods of treating a condition in the eye of a subject using the intraocular implants described herein are also provided. In general, the methods described herein may comprise advancing a drug-eluting implant through the conjunctiva and the sclera of the eye of the subject, positioning a portion of the implant in the sclera and a first end of the implant in the sulcus, and delivering a drug from the implant to the sulcus of the subject to reduce a symptom of the condition of the eye. Methods described herein may comprise advancing a drug-eluting implant through the conjunctiva and/or the sclera of the eye, positioning a drug-eluting implant fully intramurally in the eye with at least a portion of the drug-eluting implant in a limbus of the eye, and delivering a drug from the implant to an anterior chamber of the eye to reduce a symptom of the condition of the eye. Methods may also generally comprise advancing a drug-eluting implant through the conjunctiva and the cornea of the eye, positioning a portion of the implant in the cornea and a first end of the implant in the anterior chamber, and delivering a drug from the implant to the anterior chamber to treat the condition of the eye and/or to reduce one or more symptoms of the condition of the eye. Any of the above-described intraocular implants and delivery devices are suitable for use with the methods described herein. A delivery device described herein may deliver a drug (e.g., as a solid, liquid, emulsion) directly into a tissue of the eye, alternatively or in addition to an implant Prior to administering the drug-eluting implant, the eye may be anesthetized, and one or more antiseptics may be applied to the eye to prepare it for the implantation procedure. Anesthesia may include one or a combination of the following types of anesthesia: topical, subconjunctival, sub-Tenon's, peribulbar, and retrobulbar. In some instances, an eyelid speculum may be applied to expose the ocular surface and prevent the eyelids from closing. In some instances, it may be advantageous to dilate the pupil. The procedure may also be performed at a slit lamp with the patient seated upright, or it may be performed at a microscope with the patient supine. In some embodiments, the implant may be advanced and/or positioned using loupes, a sit lamp, or a surgical microscope. The procedure may be done in an operating room, although, advantageously, the methods described herein are suitable for being performed at a doctor's office or in a minor procedure room. The methods described herein may be performed with or without the use of gonioscopy or microinvasive glaucoma surgery (MIGS)-type implantations. Instead, many of the methods described herein allow for injection into a tissue of the eye, performed at a slit lamp or in an office-based setting by an ophthalmologist or optometrist. While these procedures may be performed in an operating room, there are many advantages to performing them in an office-based setting (e.g., cost savings, convenience for the patients, increased appointment availability and/or access).

In some variations, the intraocular implant must be advanced through the sclera or cornea to reach the desired or target location or position within the eye. Advancing the implant through the sclera or cornea may comprise advancing the implant through the sclera or cornea in a delivery device. The methods may comprise puncturing the sclera or cornea with a needle or cannula, such as a needle or cannula of a delivery device, and advancing the needle or cannula carrying the implant therein to a desired location, such as directly within a mural tissue or partially within the sulcus. In some embodiments, methods may comprise creating an intramural tunnel or channel separately from, and prior to, advancing the implant to the target location. In these variations, the tunnel or channel may be created with an instrument such as a needle or a femtosecond laser. In other variations, the channel or tunnel may be created using the implant delivery device prior to, or during, advancement of the intraocular implant to the desired location. In some embodiments, the intraocular implant may be positioned within the mural tissue directly, or within a tunnel or channel, and may also comprise operating an actuator of the delivery device to release the implant from the delivery device. The actuator may comprise, for instance, a button, a knob, or a slider. In some variations, one or more actuator may be coupled to a handle of the delivery device.

The methods may comprise positioning the implant partially in the sclera with a first end residing in the sulcus, vitreous, or anterior chamber and a second end residing in the subconjunctival space. In certain variations, the methods may comprise positioning the implant partially in the sclera with a first end residing in the sulcus, vitreous, or anterior chamber (e.g., in the iridocorneal angle) and a second end residing in the sclera. In some embodiments, the implant may be advanced to a target position in which a portion of the intraocular implant is positioned at least partially in the sclera and the remainder of the implant may be positioned within one or more of the sclera, cornea, and limbus. For instance, the methods may comprise advancing the intraocular implant such that one end is positioned in the sclera and the other end is positioned in the sulcus. The methods may comprise advancing the intraocular implant such that one end is positioned in the sclera, limbus, or cornea and the other end is positioned in the anterior chamber (e.g., the iridocorneal angle). The methods may comprise advancing the intraocular implant such that one end is positioned in the sulcus and the other end is positioned in the subconjunctival space. Both ab-externo and ab-interno approaches to these methods are contemplated.

In some variations, a space may be created in the cornea, limbus, and/or sclera with a device suitable for creating a pocket, channel, flap, or interlamellar space. Such spaces can be created, for instance, with corneal separators, microkeratomes, and/or femtosecond lasers. Subsequently, the implant may be deployed with a second device or system into the preformed space.

The methods described herein comprise positioning a portion of the implant in the sclera and a first end of the implant in the sulcus. In some embodiments, the positioning step comprises operating an actuator to release the implant from the delivery device or system. As described herein, the actuator may comprise a button, a knob, and/or a slider. The actuator may, for instance, control a pusher in contact with or coupled to the intraocular implant. In some embodiments, a guidewire may contact a portion of the implant, and the implant may be advanced from a cannula and/or positioned using the guidewire. After delivering the implant to the target tissue with the guidewire, the implant may be released from the guidewire and/or the guidewire may be withdrawn, leaving the implant in place.

Generally, the methods described herein provide a means of anchoring the intraocular implant within the eye. In certain embodiments, the positioning step comprises fixing a position of the implant using an anchoring element. Any number of anchoring elements may be used with the intraocular implants and methods described herein. As discussed above, suitable anchoring elements may be present on any portion of the elongate implant body, including any portion of the intraocular implant or the elongate implant body residing within the sclera, within the sulcus (between the first end of the elongate implant body and the sclera), or within the subconjunctival space. Suitable anchoring elements include knots, beads, barbs, coils, or crossbars. In some embodiments, the first and second anchoring elements are expandable anchoring elements (e.g., expandable barbs, expandable crossbars). In these embodiments, positioning an implant within the eye may comprise transition the anchoring elements from a first, low-profile configuration to a second expanded configuration. For example, the anchoring elements may be held in the compressed, low profile configuration when the implant is positioned within the delivery device (e.g., within a needle or cannula of the delivery device) and once released from the delivery device, the anchoring elements, no longer confined by needle or cannula, may self-expand Once the intraocular implant is advanced into the and positioned in the desired location, the anchoring elements may be positioned in a variety of locations within the eye to secure the implant in place. For instance, in some methods, an anchoring element may be positioned between the first end of the implant and the sclera. In some variations in which the implant is positioned with a first end in the sulcus and a second end in the subconjunctival space, an anchoring element may be positioned in the sulcus. In some variations in which the implant is positioned with a first end in the sulcus and a second end in the subconjunctival space, an anchoring element may be positioned in the subconjunctival space. In some variations in which the implant is positioned with a first end in the sulcus and a second end in the subconjunctival space, an anchoring element may be positioned in the sulcus and in the subconjunctival space. In some variations in which the implant is positioned with a first end in the sulcus and a second end in the subconjunctival space, an anchoring element may be positioned in the sulcus, in the subconjunctival space, and in the sclera.

In some variations in which the implant is positioned with a first end in the sulcus and a second end in the sclera, an anchoring element may be positioned on a length of the implant residing in the sulcus. In some variations in which the implant is positioned with a first end in the sulcus and a second end in the sclera, an anchoring element may be positioned on a length of the implant residing in the sclera. In some variations in which the implant is positioned with a first end in the sulcus and a second end in the sclera, an anchoring element may be positioned on a length of the implant residing in the sulcus and on a length of the implant residing in the sclera.

In order to minimize movement and/or reduce the likelihood that the implant will slide, migrate or otherwise move from the desired location (e.g., anteriorly or posteriorly), in some embodiments, the methods described herein may comprise fixing a position of the implant using a plurality of anchoring elements, such as a first anchoring element and a second anchoring element. In some embodiments, the first anchoring element may be positioned between the first end of the implant and the sclera, and the second anchoring element may be positioned in the subconjunctival space. In some variations in which the implant is positioned with a first end in the sulcus and a second end in the subconjunctival space, the first anchoring element is present on a length of the implant residing in the sulcus and the second anchoring element is present on a length of the implant residing in the subconjunctival space. In some embodiments of the methods described herein, at least one of the first anchoring element and the second anchoring element may be an expandable anchoring element. In some embodiments, the first anchoring element and the second anchoring element are knots; and wherein the first anchoring element is implanted within the sulcus and the second anchoring element is implanted in the subconjunctival space. In some embodiments, the anchoring element is a knot.

The methods described herein may also prevent or minimize (e.g., relative to conventional implants) damage of corneal endothelial cells, as the implants described herein may be prevented from making physical contact with the endothelium. The methods described herein may, for instance, further comprise anchoring the drug-eluting implant within the eye, (e.g., within the sulcus, in the anterior chamber but distant from the endothelium), thereby resulting in minimal endothelial cell loss (e.g., endothelial cell loss negligible compared to typical age-related decline in endothelial cells). The endothelial cell loss may be less than about 1%, less than about 1.5%, less than about 2%, less than about 2.5%, or less than about 3%.

Figure 15:
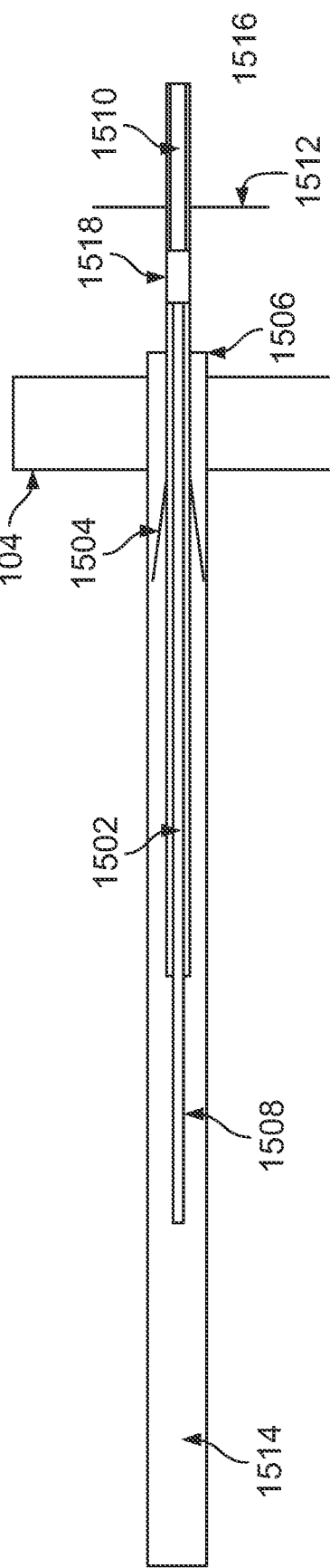
FIG. 15 shows an exemplary intraocular implant partially delivered to the eye.

FIG. 15 depicts a method of advancing and positioning an intraocular implant (1500) comprising expandable anchoring elements (shown collapsed in FIG. 13) within the eye. The distal end (1516) of a delivery device, such as, for example, a cannula (1506), containing the implant body (1502) may be inserted through the sclera and into the sulcus. A pusher (e.g., guidewire) (1508) may be advanced through a lumen (1514) of the cannula, before, during or after advancement of the cannula, and may push the implant into the sulcus (105). In some variations, the implant body (1502) may comprise a stopper (1518), and the pusher may advance the implant via contact with the stopper (1508). After being released from the cannula lumen (1515), a first anchoring element may expand (1512) within the sulcus. In this configuration, the first anchoring element (1512) may be positioned between the first end of the implant, which may also be within the sulcus, and the sclera. In some variations, the pusher (1508) may continue to be advanced to release the remainder of the implant (1500), and any remaining anchoring elements (1505), from the cannula (1506), at which point the cannula and pusher may be withdrawn from the eye. In other variations, the implant may be partially advanced from the cannula lumen using the pusher, and the implant may be fully released from the cannula lumen upon retraction or withdrawal of the cannula. In these variations, withdrawal of the cannula may release the remainder of the implant (e.g., the second end of the implant) and any remaining anchoring elements from the cannula. The cannula and the pusher may then be removed from the individually or together. The intraocular implant may be left in the eye and may be embedded partially in the subconjunctival space and partially in the sulcus, traversing the sclera. As the pusher is continued to be advanced relative to the cannula, or as the cannula is withdrawn while the pusher remains stationary, the remaining collapsed anchoring element(s) expands, e.g., in the subconjunctival space, anchoring the device (e.g., on both sides of the sclera). As depicted in FIG. 15, the first end of the intraocular implant comprises a drug, which then elutes (e.g., over a predetermined period of time) into the sulcus.

The methods described herein are suitable for use with any of the intraocular implants described previously. In some embodiments, the implant comprises a filament. In some embodiments, an implant comprising a filament may further comprise anchor elements that are knots, wherein the knots are implanted within the sulcus.

Also described herein are methods for treating a condition in an eye of a subject using intramural implants. Such methods may comprise advancing a drug-eluting implant through one or more of the sclera, limbus, and cornea of the eye of the subject, positioning the implant entirely within one or more of the sclera, limbus, and cornea, and delivering a drug from the implant to a portion of the eye (e.g., anterior chamber) to reduce a symptom of the condition of the eye. The methods may comprise positioning the implant fully within the cornea, such as, for example, with a first end and a second end residing in the cornea. In certain variations, the methods may comprise positioning the implant fully within the sclera, such as, for example, with a first end and a second end residing in the sclera. In certain variations, the methods may comprise positioning the implant partially within the limbus, with a first end residing in the cornea, a central portion residing in the limbus, and a second end residing in the sclera. In certain variations, the methods may comprise positioning the implant partially within the limbus, with a first end residing in the sclera, a central portion residing in the limbus, and a second end residing in the cornea. In certain variations, the methods may comprise positioning the implant fully intramurally, with a first end residing in the limbus and a second end residing in the sclera. In certain variations, the methods may comprise positioning the implant fully intramurally, with a first end residing in the sclera and a second end residing in the limbus. In certain variations, the methods may comprise positioning the implant fully intramurally, with a first end residing in the limbus and a second end residing in the cornea. In certain variations, the methods may comprise positioning the implant fully intramurally, with a first end residing in the cornea and a second end residing in the limbus. In some variations, the methods may comprise positioning one portion and/or end of an implant residing at least partially intramurally and another portion and/or end to reside outside of the eye (e.g., in the subconjunctival space). In some variations, the methods may comprise positioning one end partially in the sclera and one end partially outside the eye (e.g., in the subconjunctival space). In some variations, the implant is positioned partially in the limbus and partially outside the eye (e.g., in the subconjunctival space).

These methods are suitable for use with any of the intraocular implants described above.

As described above, advancing the implant (e.g., drug-eluting implant) may involve advancing a portion of a delivery device through a sclera of the eye. The implant may be disposed within the delivery device. For example, the implant may be disposed within a cannula of the delivery device, and at least a distal end of the cannula may be advanced through a sclera of the eye. The methods described herein may also allow for positioning a drug-eluting implant fully intramurally with at least a portion of the drug-eluting implant in a limbus of the eye. The methods described herein may also allow for delivering a drug from the drug-eluting implant, after placement of the implant, to a target tissue or tissues of the eye (e.g., anterior chamber) to reduce a symptom of the condition of an eye. The target tissue or tissues may be one or more tissues in which the implant resides. The target tissue or tissues may not be in contact with the implant.

Generally, some implants may be fully or partially intramural. For instance, the drug-eluting implant, comprising a drug, may be placed at least partially within the limbus of an eye of a subject. Such implants may also be fully intramural, which, as discussed previously, has the advantage of preventing damage to one or more tissues (e.g., corneal epithelial cells) as compared to implants that extend into, or fully reside and free-float within, the anterior chamber.

In order to deliver the implant, the method may comprise advancing a distal tip of a cannula of a delivery device (such as any of the delivery devices described herein) through one or more tissues, cavities, or structures of the eye (e.g., through a sclera and a limbus into an anterior chamber).

After advancing the cannula, wherein the implant is disposed, the cannula may be visualized in a particular portion of the eye or at a particular depth, informing where in the eye the implant will reside once the cannula is retracted. Thus, methods may further comprise visualizing the distal tip of the cannula within a particular tissue, cavity, or structure of the eye (e.g., the anterior chamber) prior to releasing the implant from the delivery device. For instance, the cannula may be visualized within one or more tissues, cavities, or structures of the eye, within which the implant will reside. Additionally, or alternatively, the cannula may be visualized within one or more tissues, cavities, or structures of the eye adjacent to, or within the proximity of, the desired implant location.

Visualizing the cannula through the posterior portion of the eye may assist a user in in properly positioning the implant within the eye, as described above. Accordingly, methods may comprise confirming the distal tip of the cannula is positioned within a desired portion of the eye, such as, within the anterior chamber of the eye. Once the distal tip of the cannula has been advanced to a desired depth within the eye, methods may further comprise retracting the cannula and releasing the drug-eluting implant in the target tissue (e.g., at least partially in the limbus).

In some variations of the methods described herein, the distal tip of the cannula of a delivery device may enter the anterior chamber during positioning of the drug-eluting implant, and the cannula may be advanced into the anterior chamber to a depth corresponding to the offset of the implant from the distal tip of the cannula (e.g., about 0.5 mm to about 10.0 mm) in order to position the implant as desired. For example, in some variations, the cannula may be advanced into the anterior chamber to a depth that results in delivery of the implant to the limbus (e.g., so that the implant resides at least partially within the limbus after implantation/release from the delivery device). In some of these variations, the implant may not enter the anterior chamber at all, either during implantation when the distal tip of the cannula is in the anterior chamber, or after, when the implant is residing in the eye for delivery of drug thereto.

After advancing the distal tip of the cannula, positioning a drug-eluting implant may comprise retracting or otherwise withdrawing the cannula in relation to the tissue of the eye, leaving the implant in the desired tissue. The cannula may be retracted via operation of one or more actuators of the delivery device. For instance, the cannula may be retracted via operation of 1, 2, 3, or more actuators, and the actuator may comprise one or more of a button, knob, and slider. In some variations, the cannula may be retracted by movement of a handle coupled thereto. In some variations, the cannula may be retracted by moving the entire body of the cannula, which may comprise additional structural features such as a handle. In variations, the implant stays stationary during retraction of the cannula.

In some variations, the cannula or drug-eluting implant may be visualized during advancement and/or positioning using loupes, a slit lamp, a surgical microscope, or any combination thereof.

Positioning may also comprise fixing a position of the drug-eluting implant to a tissue of the eye using at least one anchoring element. Examples of anchoring elements include surface ridges, knobs, ribs, bulbs, and barbs fixed to the implant. Any anchoring elements described herein may be configured in such a way that they are stowed or undeployed while residing in the cannula and subsequently deployed once the cannula is retracted. Put another way, methods described herein may comprise expanding or otherwise deploying one or more anchoring elements, such as, for example, automatically upon removal of the implant from the delivery device.

In some variations, such as those where an implant resides fully intramurally, anchoring elements may be positioned and fixed to one or more tissues of the eye. For instance, in some of the methods described herein, at least one anchoring element may be positioned in and coupled (e.g., fixed) to the limbus. In some embodiments, at least one anchoring element may be positioned in and coupled to the sclera. In certain embodiments, at least one anchoring element may be positioned in and coupled to the cornea. A plurality of anchoring elements may be positioned and coupled to more than one tissue, such as the limbus and sclera; the limbus and cornea; or the limbus, cornea, and sclera. Specifically, multiple anchoring elements may be coupled to the same tissue. In some variations in which there are multiple anchoring elements, each anchoring element may be coupled to a different tissue.

The implants described herein may deliver drugs to various locations, irrespective of where in the eye they reside. In any of the methods described herein, a drug-eluting implant may deliver a drug to a tissue or tissues in which the drug-eluting implant resides, and/or to a location or tissue(s) that is different from the tissue or tissues in which the drug-eluting implant resides. For instance, a drug-eluting implant may reside fully intramurally but may deliver a drug to the anterior chamber of the eye via diffusion through the tissue(s). A drug-eluting implant residing fully in the limbus may deliver a drug to one or more of the limbus, sclera, cornea, anterior chamber, or any other nearby tissue or structure of the eye. A drug-eluting implant residing partially in the limbus and partially in the sclera may deliver a drug to one or more of the limbus, sclera, cornea, anterior chamber, or any other tissue or structure of the eye. In certain variations, the drug from the drug-eluting implant may diffuse through one or more aqueous outflow channels. FIGS. 23A-23G depict an exemplary method of placing a drug-eluting implant at least partially within a limbus of an eye.

Figure 23A:
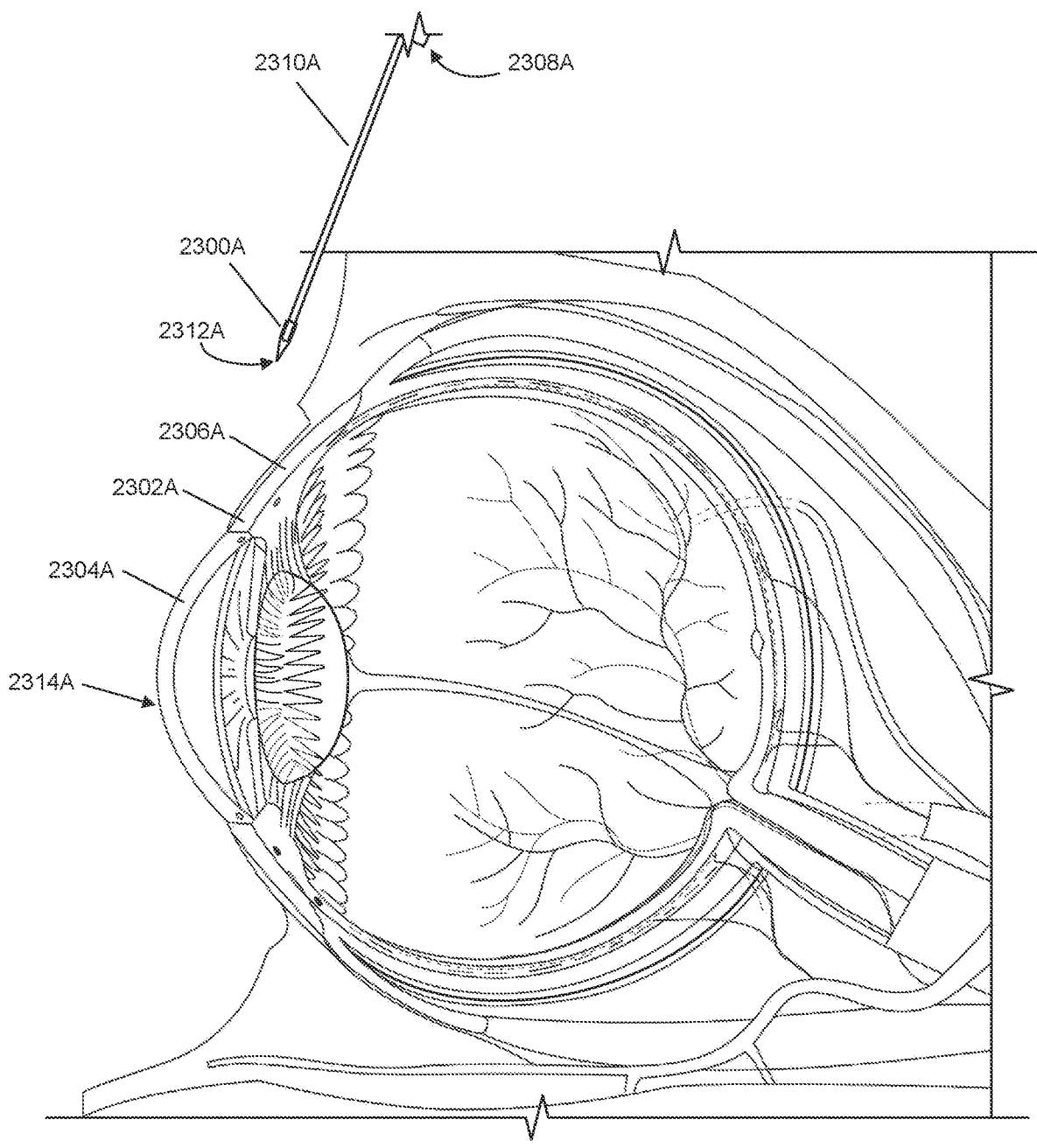
FIGS. 23A-23G depict a variation of a method for placing a drug-eluting implant at least partially within the limbus of an eye.

By way of example, the first step in placing a drug-eluting implant may involve preparing the eye for the procedure. Specifically, FIG. 23A depicts a eye pre-procedure, prior to placing a drug-eluting implant (2300A) at least partially within the limbus (2302A) of an eye. For reference, and as described above, the limbus lies between the cornea (2304A) and the sclera (2306A). The implant (2300A) may be positioned within the delivery device such that the implant (2300A) is disposed in the cannula (2310A) a pre-defined distance from the distal tip (2312A) of the cannula. The ocular surface (2314A) may be anesthetized, and/or antiseptic drops may be placed on the eye. An eyelid speculum may be inserted to keep the eyelids open for the duration of the procedure.

Figure 23B:
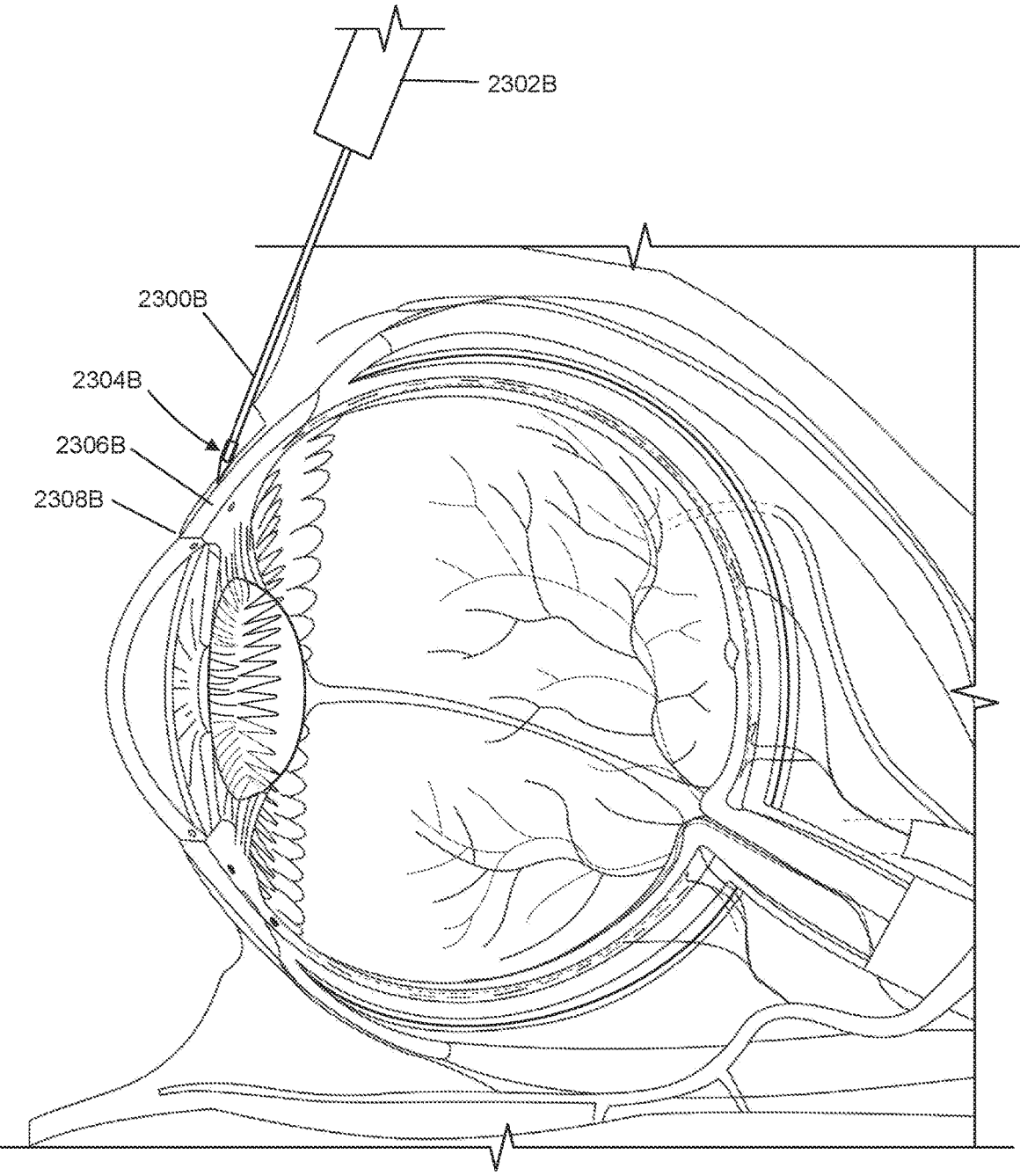

After preparing the eye, a cannula may be advanced toward the subject's ocular surface. The cannula (2300B) of the delivery device (2302B) carrying the implant (2304B), as shown in FIG. 23B, may be advanced toward the sclera (2306B) posterior to the limbus (2308B).

Figure 23C:
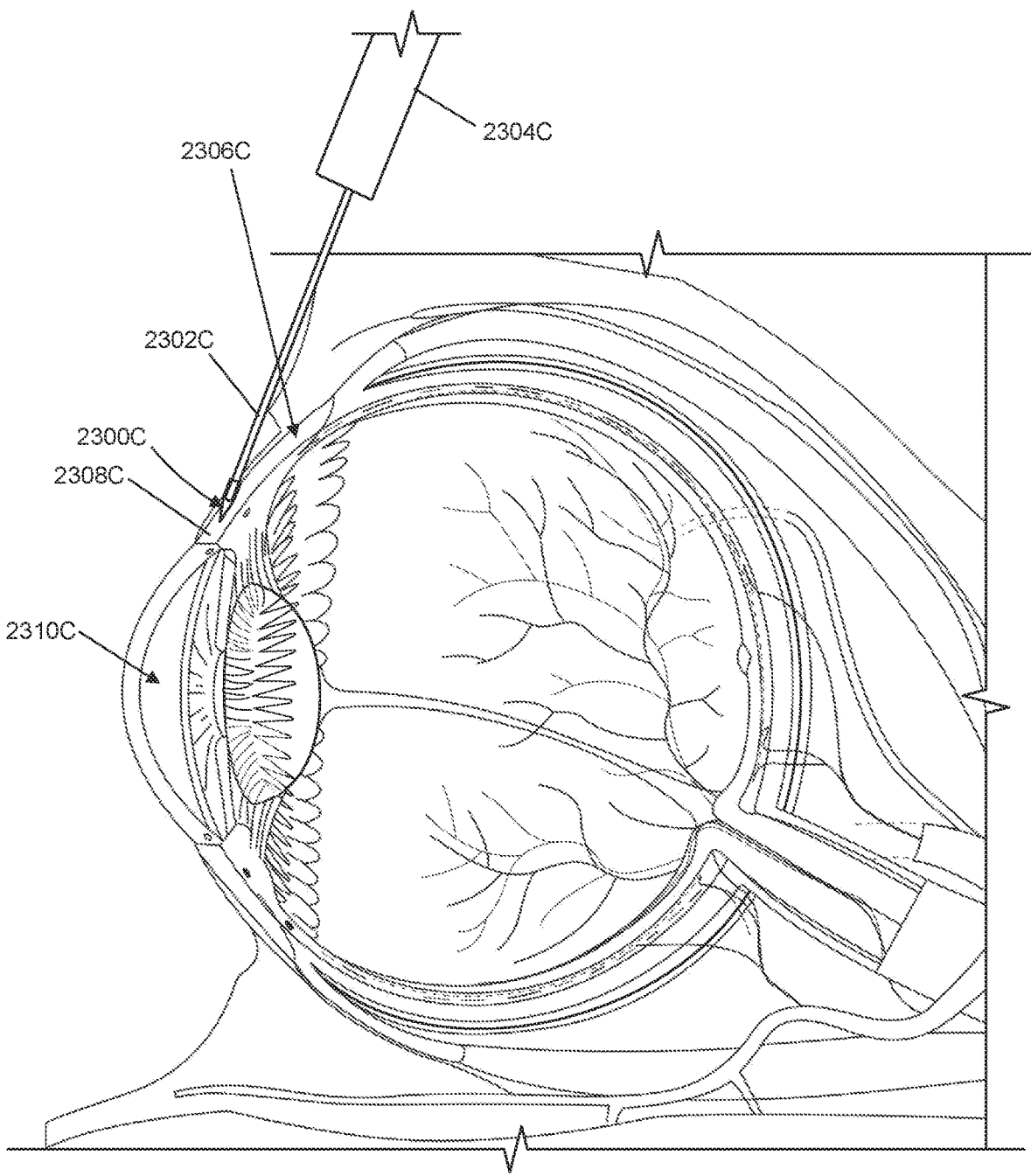

After orienting the cannula of a delivery device, the cannula carrying the implant enters the eye at a location sufficient to reach the target tissue or structure of interest. As shown in FIG. 23C, the distal tip (2300C) may be advanced into the sclera (2306C) posterior to the limbus (2308C). In some variations, the distal tip (2300C) of the cannula (2302C) of the delivery device (2304C) may be advanced into the sclera (2306C) about 2-3 mm posterior to the limbus (2308C). As shown in FIG. 23C, in some variations, the cannula may be advanced at an angle into the sclera such that the distal tip (2300C) will pass through the sclera (2304), through the limbus (2308C), and into the anterior chamber (2310C).

Figure 23D:
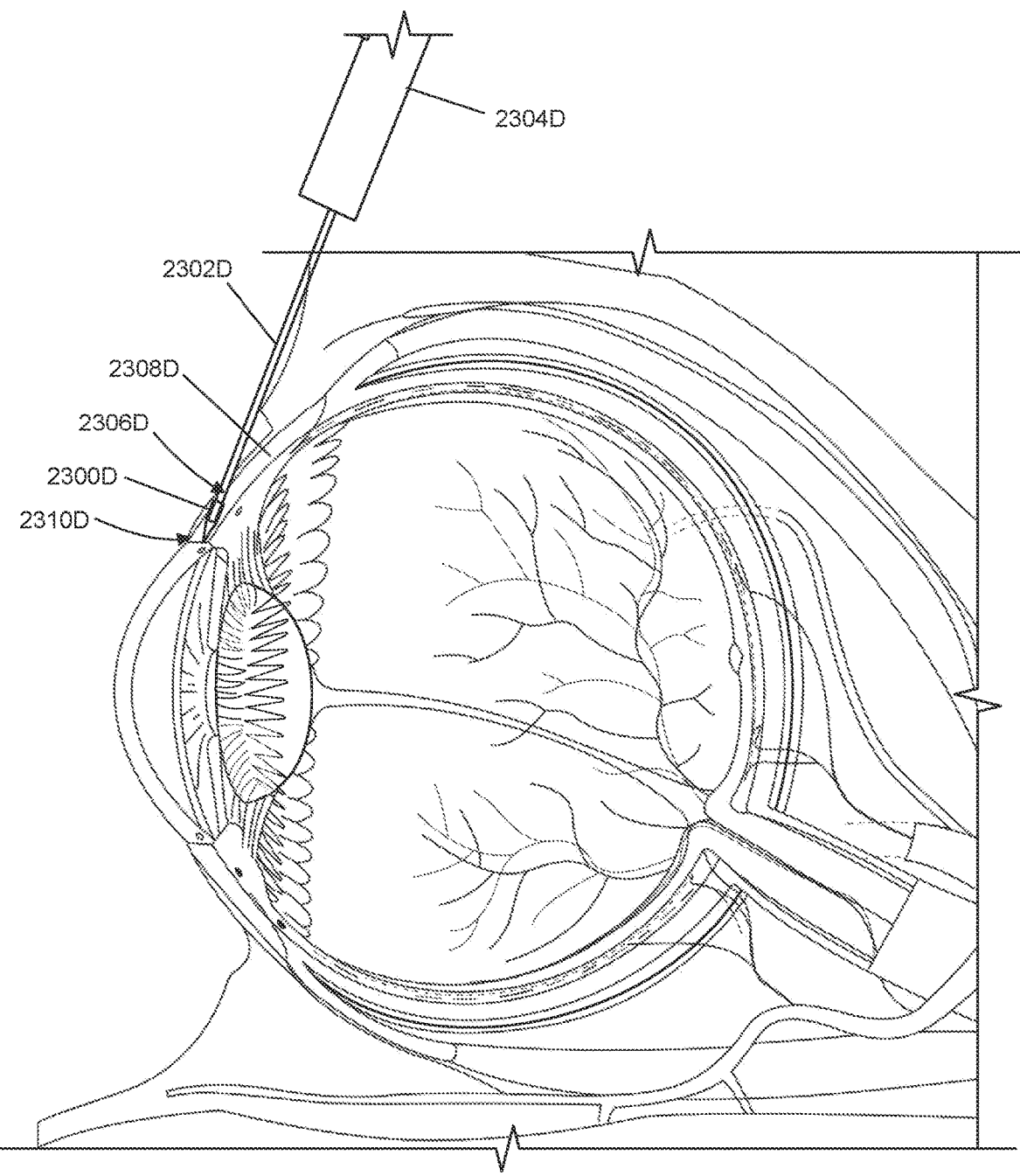

The cannula is then advanced through one or more tissues or structures of the eye toward the desired implant location. FIG. 23D depicts the distal tip (2300D) of the cannula (2302D) of a delivery device (2304D), within which the implant (2306D) is disposed, advancing through the sclera (2308D) and limbus (2310D).

Figure 23E:
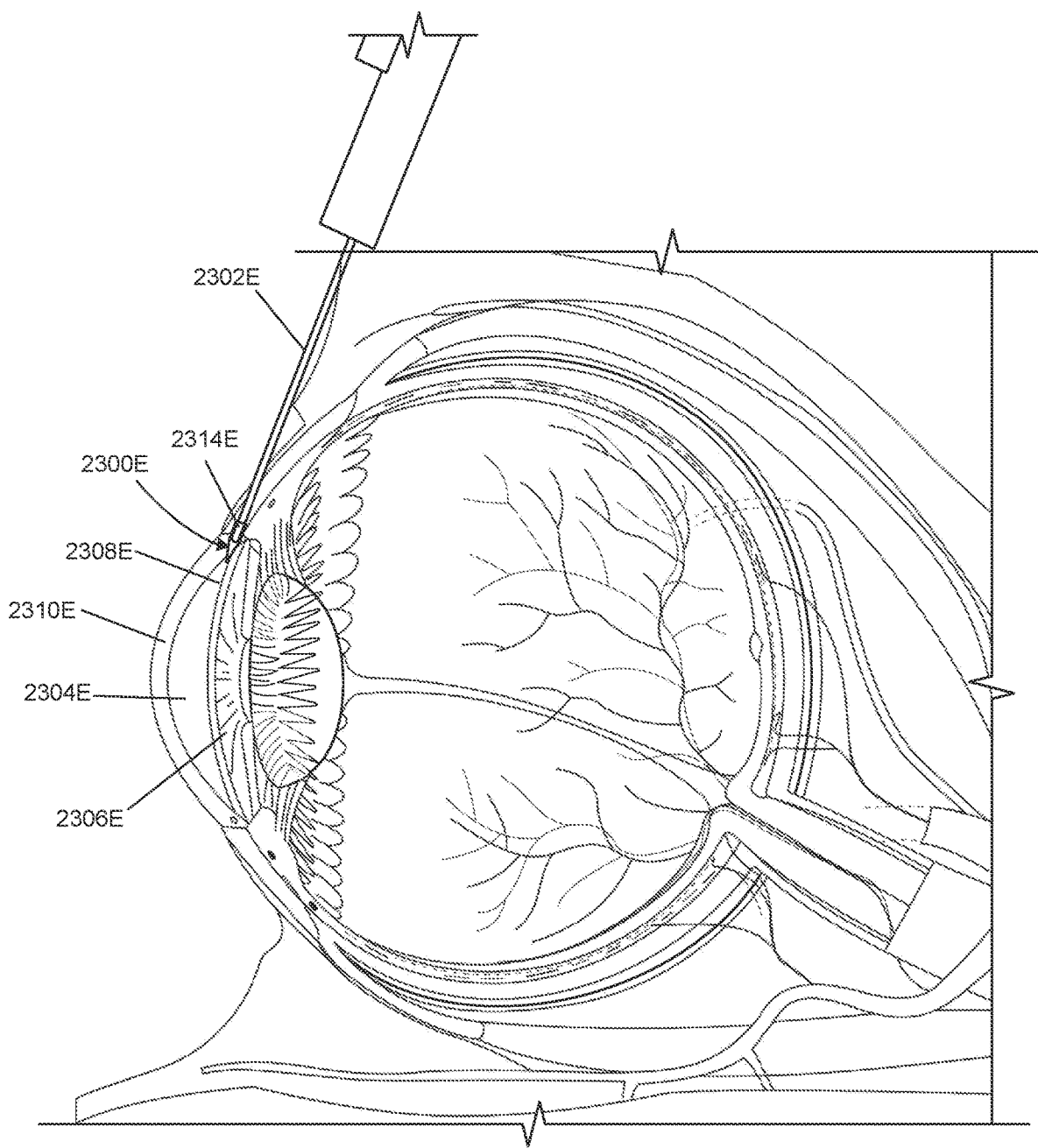

The proper positioning of the implant may be confirmed by visualizing a component of the delivery device (e.g., a cannula), externally, using methods described above. FIG. 23E depicts the distal tip (2300E) of the cannula (2302E) advancing into the anterior chamber (2304E) anterior to the iris (2306E). For instance, the distal tip (2300E) may enter at the anterior chamber angle (2308E) or in the cornea (2310E) just anterior to the anterior chamber angle (2312E). Advancement of the cannula (2302E) may be visualized (e.g., with a surgical or slit lamp). The depth to which the distal tip (2300E) is advanced into the anterior chamber (2304E) may be predetermined based on the size of the implant (2314E) and the desired final intramural position of the implant (2314E). For instance, in variations in which a 0.5 mm implant is used, and is implanted fully intramurally at least partially in the limbus, without entering the anterior chamber, the implant may initially be disposed in the cannula 1 mm from the distal tip. The distal tip is visualized as it is advanced into the anterior chamber to a depth of 1 mm or less, meaning that the implant disposed 1 mm from the tip, is still fully intramural and has not entered the anterior chamber. The cannula can then be retracted, leaving the implant intramurally, at least partially within the limbus.

Figure 23F:
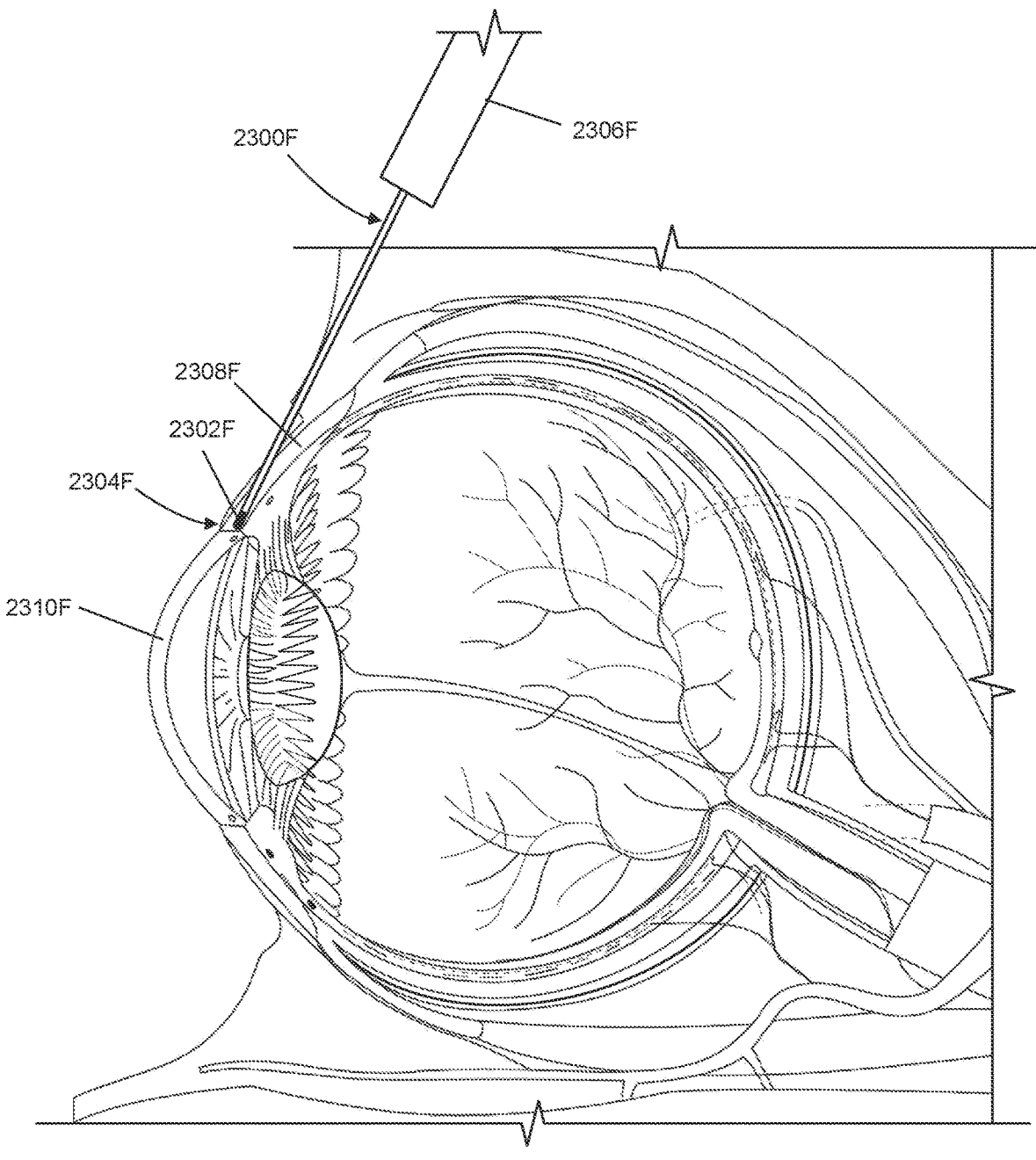
Figure 23G:
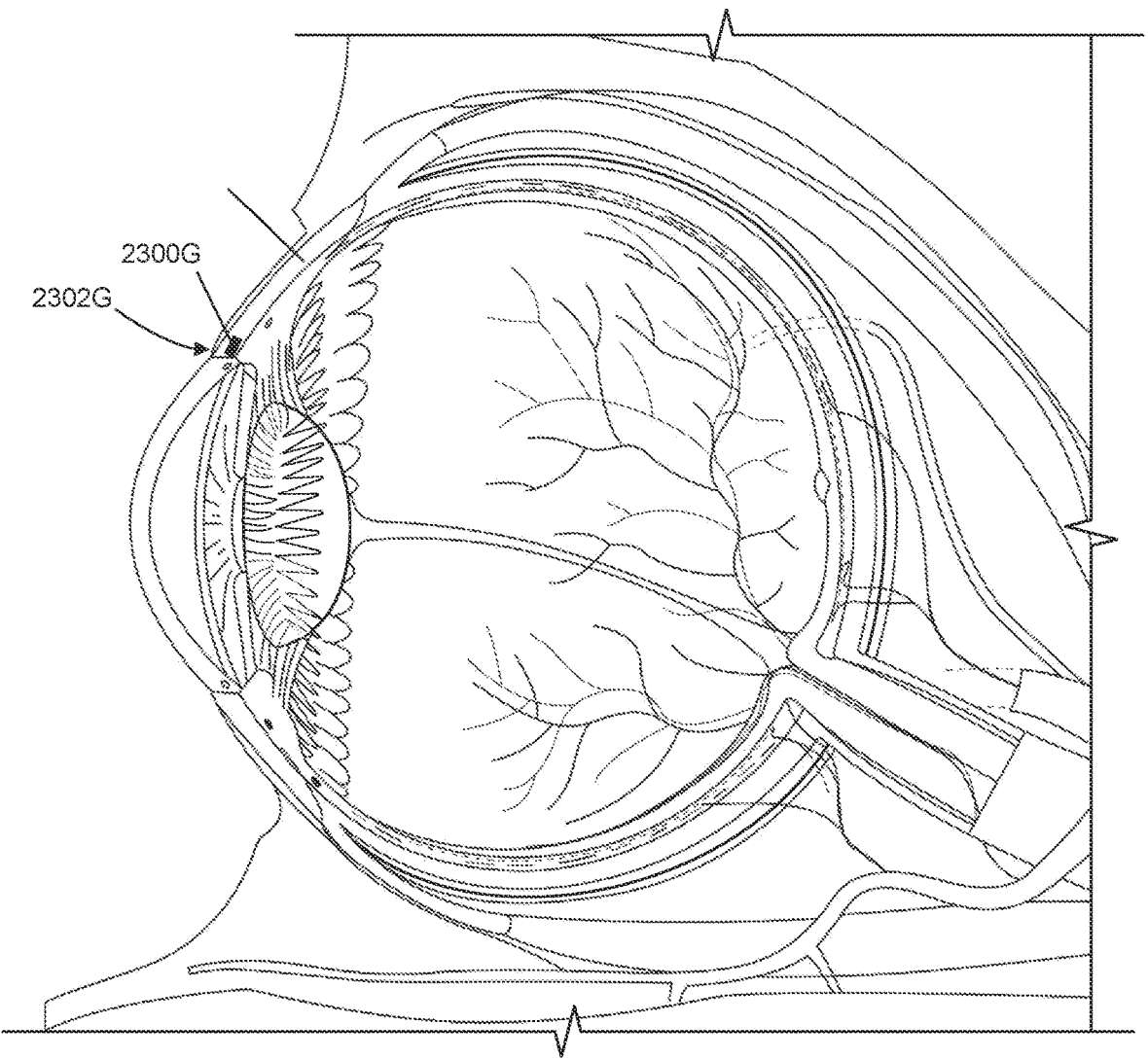

Once the proper position of the implant is attained, the cannula is retracted. FIG. 23F depicts the retraction of the cannula (2300F), which may release the implant (2302F) from the cannula (2300F) and, in this variation, implant it intramurally, and at least partially within the limbus (2304F). In some variations, the cannula (2300F) may be retracted via operation of an actuator of the delivery device (2306F) (e.g., on a handle of the delivery device). A portion or portions of the implant (2302F) may reside in the sclera (2308F) or the cornea (2310F), depending on the length of the implant (2302F). FIG. 24F shows the implant (2300G) in its final location at least partially within the limbus (2302G).

The methods of treating a condition in of an eye of a subject, as described herein, may be useful for treating a number of ocular disorders or conditions. These ocular disorders include, but are not limited to, glaucoma, AMD, choroidal diseases, retinal diseases, corneal diseases, iris diseases, uveal diseases, lens diseases, and scleral diseases (e.g., myopia). In some embodiments, the methods described herein may be useful for treating macular edema, vascular occlusions, diabetic retinopathy, retinal degenerations, and retinal dystrophies, iritis, uveitis, vitritis, cataracts, herpes zoster or simplex infection, keratitis, keratoconus or other corneal degenerations, dry eye disease, scleritis, episcleritis, corneal ulcer, astigmatism, hyperopia, presbyopia, cornea ectasia, corneal dystrophies, corneal scars, graft versus host disease, autoimmune ocular diseases, Thygeson's keratitis, post-viral keratitis, herpes simplex, viral keratitises, uveitis, Stevens Johnson Disease, conjunctivitis, blepharitis, postoperative inflammation, postoperative infection prophylaxis, postoperative pain, pingueculum, pingueculitis, pterygium, vernal and atopic keratoconjunctivitis, allergic conjunctivitis, chemical injuries, thermal injuries, chemical injuries, mechanical injuries, retinal vasculitis, retinal dystrophies, neuroretinopathies, autoimmune retinal diseases, autoimmune choroidal diseases, retinal detachment, retinal tears, retinal breaks, ischemic and nonischemic optic neuropathies, tapetoretinal dystrophies, ocular trauma, radiation retinopathy, exudative or nonexudative age related macular degeneration, choroidal neovascularization, retinal neovascularization, retinal vascular occlusive disease, choroidal or retinal inflammation, vitreous opacities (e.g., hemorrhage, floaters, asteroid hyalosis), maculopathies, retinopathies, choroidopathies, retinopathy of prematurity, endophthalmitis, epiretinal membrane hole, macular hole, proliferative vitreoretinopathies, edema (e.g., macular, retinal), ischemia (e.g., macular, retinal), or diabetic retinopathy. In some variations, the methods described herein may result in decreased duration, severity, and/or occurrence of one or more symptoms of any of the aforementioned conditions and/or may result in treatment of any of the aforementioned conditions. The methods described herein, therefore, may utilize a drug-eluting implant that delivers a drug to treat any of these, or other, disorders or conditions. In some embodiments, the dug-eluting implant may deliver a glaucoma drug. In some variations, the methods described herein may utilize a drug-eluting implant located partially in a first part of the eye to treat a disorder in the same part of the eye or another part of the eye.

Because the methods of this disclosure provide for long-term administration of a drug to eye tissue, in some variations, it may be desirable to replace drug that has diffused from the drug-eluting implant. Thus, some embodiments of the methods disclosed herein further comprise refilling the drug-eluting implant and/or replacing a drug reservoir coupled to or contained with the implant. Refilling the drug-eluting implant may be accomplished, for instance, by delivering a drug, a solution of the drug, a slurry of the drug, and emulsion of the drug, or a drug-eluting matrix by injection into one or more hollow cavities, lumens, or reservoirs in the drug-eluting implant within the eye. As described previously, some reservoirs comprise a port through which drug can be provided. The methods described herein allow for refilling the drug-eluting implant with the same or different therapeutic agent. In some variations, instead of refilling a drug reservoir, the reservoir may be removed and replaced with a new reservoir containing a drug, a solution of the drug, a slurry of the drug, and emulsion of the drug, or a drug-eluting matrix.

The methods described herein also allow for removal of the implant from the eye after it has been implanted. For instance, the implant may be removed from the eye once treatment has finished. In some variations, an instrument configured for removal of an implant or implant body may engage with a portion of the implant or implant body, such as, an end of the implant body, a central portion of the implant body, an anchoring element, and/or a portion of a housing. In embodiments in which the implant body comprises a suture or filament, an instrument may engage an end of the suture or filament for retrieval of the implant from the eye. In some variations of the methods described herein, implants may additionally comprise a removal feature configured to be grasped for removal of the implant from the eye. For example, in some variations, the removal feature may comprise a wire, filament, suture, tab, or other structure coupled to the implant body or housing. In these variations, methods may comprise engaging the removal feature of the intraocular implant with an instrument (e.g., forceps) and removing the implant from the eye using the removal feature. The implant may be removed after a drug-eluting matrix is absorbed or partially absorbed, decreasing the dimensions of an implant such that removal is easier. It may also be desirable to remove the implant to refill the implant, replace the reservoir, or to replace the implant with a second or subsequent implant comprising the same or a different therapeutic agent.

The methods described herein may comprise delivering a plurality (e.g., two, three, four, or more) of implants to the eye. The implants may be delivered such that they reside in the eye simultaneously and/or sequentially (e.g., the implants may both be implanted for the same period of time, for different, overlapping periods of time, or for different non-overlapping periods of time). In variations in which a plurality of implants are employed, the implants may comprise the same drug, may comprise different drugs with the same mechanism of action for one or more conditions of the eye, or may comprise different drugs with different mechanisms of action for one or more conditions of the eye. The implants may comprise a drug intended to treat or reduce a symptom of the same condition of the eye, or may comprise a drug intended to treat or reduce a symptom of different conditions of the eye. Moreover, the implants may be positioned in the same general location in the eye or in different locations in the eye. It should be appreciated that while the implants are described as comprising a drug, this may include combinations of drugs.

For example, methods may comprise positioning a first implant comprising a first drug intended to treat or reduce a symptom of a first condition in a first location in the eye and positioning a second implant comprising a second drug intended to treat or reduce a second condition in a second location in the eye. In some variations, the first drug and the second drug may be the same drug, the first condition and the second condition may be the same condition, the first implantation location and the second implantation location may be the same location, and the first drug and the second drug may utilize the same mechanism of action. In other variations, the first drug and the second drug may be different drugs, the first condition and the second condition may be different conditions, the first implantation location and the second implantation location may be different locations, and/or the first and second drugs may utilize different mechanisms of action. Thus, in some variations, the first and second drugs may be different drugs that utilize different mechanisms of action, but the first and second locations may be the same location and the first and second conditions may be the same condition. In another example, the first and second drugs may be different drugs that utilize different mechanisms of action and the first and second locations may be different locations, but the first and second conditions of the eye may be the same. It should be appreciated that any combination of drugs, mechanisms of action, locations, and conditions of the eye described herein may be used in combination when utilizing methods comprising use of multiple intraocular implants.

For some subjects, it may be advantageous to deliver multiple implants configured to deliver different drugs or to deliver drugs that utilize different mechanisms of action as this may allow for a more comprehensive treatment. For example, methods may comprise positioning a first implant comprising a first drug with a first mechanism of action with a first end in the sulcus and positioning a second implant comprising a second drug with a second mechanism of action at least partially in the anterior chamber or posterior chamber. In some variations, the first mechanism of action may be suppression of production of aqueous humor and the second mechanism of action may be increasing the drainage of aqueous humor using one or more of the trabeculocanicular pathway and the uveoscleral pathway. In other variations, both the first mechanism of action and the second mechanism of action may be suppression of aqueous humor or increasing drainage of aqueous humor using one or more of the trabeculocaniclular pathway and the uveoscleral pathway. In some variations, the first and second mechanisms of action may be increasing drainage of aqueous humor, however, the first mechanism of action may be increasing drainage through the trabeculocanicular pathway and the second mechanism of action may be increasing drainage through the uveoscleral pathway. In some variations, the first implant may comprise a drug for treating or reducing one or more symptoms of glaucoma (e.g., by suppression of aqueous humor, increasing drainage of aqueous humor using the trabeculocanicular pathway, increasing drainage of aqueous humor using the uveoscleral pathway) or a condition of the retina, lens, cornea, uvea, vitreous, iris, ciliary body, sclera, or ocular surface, and the second implant may comprise a drug for treating or reducing one or more symptoms of glaucoma or a condition of the retina, lens, cornea, uvea, vitreous, iris, ciliary body, sclera, or ocular surface. For example, the first implant and the second implant may each comprise a drug for treating or reducing one or more symptoms of glaucoma, and the drug may be the same or a different drug. In another example, the first implant may comprise a drug for treating or reducing one or more symptoms of glaucoma and the second implant may comprise a drug for treating or reducing one or more symptoms of retinal disease. In some variations, the first implant and the second implant may each comprise a drug for treating or reducing one or more symptoms of AMD, and the drug may be the same or a different drug. In another example, the first implant may comprise a drug for treating or reducing one or more symptoms of glaucoma and the second implant may comprise a drug for treating or reducing one or more symptoms of AMD.

The plurality of implants may be advanced to a desired position in the eye using the same, or different, approaches and/or delivery devices and systems. For example, in some variations, methods may comprise advancing a first drug-eluting implant and a second drug-eluting implant through conjunctiva and sclera of the eye of the subject and positioning a portion of the first implant and the second implant in the sclera and a first end of the first implant and the second implant in the sulcus. In some variations, methods may comprise advancing a first drug-eluting implant and a second drug-eluting implant into the eye of the subject, and positioning a portion of the first implant in the posterior chamber (e.g., within the sulcus, within the sulcus and partially extending into the remainder of the posterior chamber) and a portion of the second implant in the anterior chamber. In some variations, methods may comprise advancing a first drug-eluting implant and a second drug-eluting implant into the eye, and positioning the entirety of the first implant in the intramural tissue (e.g., sclera, limbus, cornea) and a portion of the second implant in the anterior chamber. In some variations, methods may comprise advancing a first drug-eluting implant and a second drug-eluting implant into the eye, and positioning the entirety of the first implant in the intramural tissue (e.g., sclera, limbus, cornea) and a portion of the second implant in the sulcus or posterior chamber. It should be understood that each implant positioned within the eye of the subject may treat the same or different conditions of the eye.

EXEMPLARY EMBODIMENTS

Embodiment I-1. An intraocular implant for treating a condition of the eye, the intraocular implant comprising:

an elongate implant body comprising a first end and a second end, wherein the elongate implant body is configured to be positioned at least partially in the sclera such that the first end of the elongate implant body is positioned in the posterior chamber or anterior chamber;

at least one anchoring element coupled to or formed from the elongate implant body; and a drug, wherein the implant is configured to deliver the drug to the eye.

Embodiment I-2. The intraocular implant of embodiment I-1, wherein the elongate implant body comprises a filament, a sheet, a cylindrical capsule, a coil, a rod, a screw, or a tubular body.

Embodiment I-3. The intraocular implant of embodiment I-1, wherein the elongate implant body comprises a tubular body and a plurality of expandable arms.

Embodiment I-4. The intraocular implant of embodiment I-1, wherein the elongate implant body comprises a tubular body, and wherein the at least one anchoring element comprises a plurality of beads or barbs positioned along a length of the tubular body.

Embodiment I-5. The intraocular implant of embodiment I-1 further comprising a housing coupled to the first end of the elongate implant body and configured to be positioned in the sulcus or anterior chamber, wherein the housing comprises the drug.

Embodiment I-6. The intraocular implant of embodiment I-5, wherein an external surface of the housing is coated with the drug.

Embodiment I-7. The intraocular implant of embodiment I-5, wherein the housing comprises a reservoir containing the drug.

Embodiment I-8. The intraocular implant of embodiment I-5, wherein the housing is a coil.

Embodiment I-9. The intraocular implant of embodiment I-5, wherein the housing is a cage.

Embodiment I-10. The intraocular implant of embodiment I-5, wherein the housing comprises an erodible drug-eluting matrix.

Embodiment I-11. The intraocular implant of embodiment I-5, wherein the housing is a canister comprising a shell and a hollow interior chamber.

Embodiment I-12. The intraocular implant of embodiment I-11, wherein the canister comprises fenestrations through the shell to deliver the drug from the interior chamber to the eye.

Embodiment I-13. The intraocular implant of embodiment I-11, wherein the canister comprises a first canister end and a second canister end.

Embodiment I-14. The intraocular implant of embodiment I-13, wherein the first canister end and second canister end are closed.

Embodiment I-15. The intraocular implant of embodiment I-13, wherein the first canister end comprises an opening and the second canister end is closed.

Embodiment I-16. The intraocular implant of embodiment I-15, wherein the opening is sealed with a membrane permeable or semi-permeable to the drug.

Embodiment I-17. The intraocular implant of embodiment I-13, wherein the first housing end comprises a first opening and second housing end comprises a second opening.

Embodiment I-18. The intraocular implant of embodiment I-17, wherein at least one of the first opening and second opening is sealed with a membrane permeable of semi-permeable to the drug.

Embodiment I-19. The intraocular implant of embodiment I-5, wherein the elongate implant body comprises a first longitudinal axis and the housing comprises a second longitudinal axis, and wherein the housing is coupled to the elongate implant body such that the first longitudinal axis is parallel with the second longitudinal axis.

Embodiment I-20. The intraocular implant of embodiment I-5, wherein the elongate implant body comprises a first longitudinal axis and the housing comprises a second longitudinal axis, and wherein the housing is coupled to the elongate implant body such that the first longitudinal axis is transverse with the second longitudinal axis Embodiment I-21. The intraocular implant of embodiment I-5, wherein the housing is refillable.

Embodiment I-22. The intraocular implant of embodiment I-5, wherein the housing is erodible.

Embodiment I-23. The intraocular implant of embodiment I-1, wherein the elongate implant body comprises a drug-eluting matrix comprising the drug.

Embodiment I-24. The intraocular implant of embodiment I-23, wherein the drug-eluting matrix comprises a polymer.

Embodiment I-25. The intraocular implant of embodiment I-23, wherein the drug-eluting matrix is erodible.

Embodiment I-26. The intraocular implant of embodiment I-23, wherein the elongate implant body comprises hollow interior chamber and a shell, wherein the elongate implant body further comprises fenestrations through the shell to deliver the drug from the drug-eluting matrix in the interior chamber to the eye.

Embodiment I-27. The intraocular implant of embodiment I-23, wherein the drug-eluting matrix is in the form of a coating on an exterior surface of the elongate implant body.

Embodiment I-28. The intraocular implant of embodiment I-27, wherein the coating is only on a first portion of the intraocular implant body.

Embodiment I-29. The intraocular implant of embodiment I-28, wherein the first portion of the implant is between the first end of the implant body and the sclera.

Embodiment I-30. The intraocular implant of embodiment I-26, wherein the drug-eluting matrix is in the hollow interior chamber of the elongate implant body.

Embodiment I-31. The intraocular implant of embodiment I-1, wherein the elongate implant body is configured to be advanced into the eye through sclera.

Embodiment I-32. The intraocular implant of embodiment I-1, where in the condition of the eye is glaucoma, age-related macular degeneration (AMD), or retinal vascular disease.

Embodiment I-33. The intraocular implant of embodiment I-1, wherein the elongate implant body does not comprise a lumen for flow of aqueous humor therethrough.

Embodiment I-34. The device of embodiment I-1, wherein the elongate implant body comprises a polymer.

Embodiment I-35. The intraocular implant of embodiment I-34, wherein the elongate implant body comprises nylon, polypropylene, poly(styrene-block-isobutylene-block-styrene) (SIBS), or polyimide.

Embodiment I-36. The intraocular implant of embodiment I-34, wherein the elongate implant body comprises a filament.

Embodiment I-37. The intraocular implant of embodiment I-36, wherein the filament comprises a plurality of braided fibers.

Embodiment I-38. The intraocular implant of embodiment I-36, wherein the filament comprises a single fiber.

Embodiment I-39. The intraocular implant of embodiment I-36, wherein the filament comprises polytetrafluoroethylene or polyester.

Embodiment I-40. The intraocular implant of embodiment I-1, wherein the second end of the elongate implant body is configured to be positioned entirely within the sclera.

Embodiment I-41. The intraocular implant of embodiment I-1, wherein the second end of the implant body is configured to be positioned outside of the sclera.

Embodiment I-42. The intraocular implant of embodiment I-41, wherein the second end of the elongate implant body is configured to be positioned in the subconjunctival space.

Embodiment I-43. The intraocular implant of embodiment I-1, wherein the at least one anchoring element comprises a first anchoring element and a second anchoring element.

Embodiment I-44. The intraocular implant of embodiment I-44, wherein the first anchoring element is configured to be positioned within the sclera, and the second anchoring element is configured to be positioned between the first end of the implant and the sclera.

Embodiment I-45. The intraocular implant of embodiment I-44, wherein the first anchoring element is configured to be positioned within the sclera, and the second anchoring element is configured to be positioned between the second end of the implant and the sclera.

Embodiment I-46. The intraocular implant of embodiment I-43, wherein the first anchoring element is configured to reside between the second end of the elongate implant body and the sclera, and the second anchoring element is configured to reside between the first end of the elongate implant body and the sclera.

Embodiment I-47. The intraocular implant of embodiment I-1, wherein the at least one anchoring element comprises a knot, bead, barb, coil, or crossbar.

Embodiment I-48. The intraocular implant of embodiment I-1, wherein the drug is an antibody, a protein, or a biologic.

Embodiment I-49. The intraocular implant of embodiment I-48, wherein the drug is ranibizumab, bevacizumab, or brolucizumab.

Embodiment I-50. The intraocular implant of embodiment I-1, wherein the drug is travoprost, latanoprost, bimatoprost, aflibercept, riboflavin, or a corticosteroid.

Embodiment I-51. The intraocular implant of embodiment I-1, wherein the drug is delivered to the eye over a period of time, wherein the period of time is at least 1 month, at least 6 months, at least 1 year, at least 2 years, or at least 3 years.

Embodiment I-52. The intraocular implant of embodiment I-1, wherein the elongate implant body comprises an erodible drug-eluting matrix, and wherein the first end of the elongate implant body has a first erosion rate and the second end of the elongate implant body has a second, different erosion rate.

Embodiment I-53. An intraocular implant for treating a condition of the eye, the intraocular implant comprising:

an elongate implant body configured to be positioned intramurally in one or more of the sclera, the cornea, and the limbus; and a drug-eluting matrix configured to release a drug to the eye, wherein the drug-eluting matrix coats an exterior surface of the elongate implant body or is contained within an interior chamber of the elongate implant body.

Embodiment I-54. The intraocular implant of embodiment I-53, wherein the elongate implant body comprises a cylinder, a sheet, a filament, or a capsule comprising an interior chamber.

Embodiment I-55. An intraocular implant for treating a condition of the eye, the intraocular implant comprising:

a spherical or rod-shaped implant body configured to be positioned entirely in the sclera, wherein the spherical or rod-shaped implant body comprises an erodible drug-eluting matrix.

Embodiment I-56. A method of treating a condition in the eye of a subject, the method comprising:

advancing a drug-eluting implant through the conjunctiva and the sclera of the eye of the subject;

positioning a portion of the drug-eluting implant in the sclera and a first end of the implant in the sulcus; and delivering a drug from the drug-eluting implant to the sulcus of the subject to reduce a symptom of the condition of the eye.

Embodiment I-57. The method of embodiment I-56, wherein the advancing the drug-eluting implant through the conjunctiva and the sclera comprises advancing the drug-eluting implant in a delivery device.

Embodiment I-58. The method of embodiment I-57, wherein the delivery device comprises a needle, and the method further comprises puncturing the sclera with the needle.

Embodiment I-59. The method of embodiment I-58, wherein the positioning step comprises operating an actuator of the delivery device to release the implant from the delivery device.

Embodiment I-60. The method of embodiment I-58, wherein the delivery device further comprises a spring configured to retract the needle.

Embodiment I-61. The method of embodiment I-60, wherein the actuator comprises a button, a knob, or a slider.

Embodiment I-62. The method of embodiment I-56, wherein the implant is advanced and/or positioned using loupes, a slit lamp, or a surgical microscope.

Embodiment I-63. The method of embodiment I-56 further comprising removing the implant from the eye.

Embodiment I-64. The method of embodiment I-56 further comprising advancing a second drug-eluting implant through conjunctiva and sclera of the eye of the subject and positioning a portion of the second implant in the sclera and a first end of the second implant in the sulcus.

Embodiment I-65. The method of embodiment I-56, wherein the positioning step further comprises fixing a position of the drug-eluting implant using an anchoring element.

Embodiment I-66. The method of embodiment I-65, wherein the anchoring element is positioned between the first end of the drug-eluting implant and the sclera.

Embodiment I-67. The method of embodiment I-65, wherein the anchoring element is positioned in the subconjunctival space.

Embodiment I-68. The method of embodiment I-56, further comprising fixing a position of the drug-eluting implant using a first anchoring element and a second anchoring element.

Embodiment I-69. The method of embodiment I-67, wherein the first anchoring element is positioned between the first end of the drug-eluting implant and the sclera, and the second anchoring element is positioned in the subconjunctival space.

Embodiment I-70. The method of embodiment I-68, wherein at least one of the first anchoring element and second anchoring element is an expandable anchoring element.

Embodiment I-71. The method of embodiment I-68, wherein the first anchoring element and the second anchoring element are knots; and wherein the first anchoring element is implanted within the sulcus and the second anchoring element is implanted in the subconjunctival space.

Embodiment I-72. The method of embodiment I-56, wherein the drug-eluting implant comprises a filament.

Embodiment I-73. The method of embodiment I-72, wherein the anchoring element is a knot, and the knot is implanted within the sulcus.

Embodiment I-74. The method of embodiment I-57, further comprising refilling the drug-eluting implant.

Embodiment I-75. The method of embodiment I-56, further comprising anchoring the drug-eluting implant within the sulcus, thereby resulting in minimal endothelial cell loss.

Embodiment I-76. The method of embodiment I-56, further comprising anchoring the drug-eluting implant within the iridocorneal angle, thereby resulting in minimal endothelial cell loss.

Embodiment I-77. The method of embodiment I-56, wherein the drug-eluting implant delivers a glaucoma drug.

Embodiment I-78. The method of embodiment I-56, wherein the drug-eluting implant is a first drug-eluting implant, and the method further comprises positioning a second drug-eluting implant in the eye.

Embodiment I-79. The method of embodiment I-78, wherein the first drug-eluting implant comprises a drug with a first mechanism of action, and the second drug-eluting implant comprises a drug with a second mechanism of action.

Embodiment I-80. The method of embodiment I-79, wherein the first mechanism of action and the second mechanism of action are the same.

Embodiment I-81. The method of embodiment I-79, wherein the first mechanism of action and the second mechanism of action are different.

Embodiment I-82. The method of embodiment I-79, wherein the first mechanism of action is suppression of production of aqueous humor and the second mechanism of action is increasing the drainage of aqueous humor through the trabeculocanicular pathway or the uveoscleral pathway.

Embodiment I-83. The method of embodiment I-79, wherein both the first and second mechanisms of action are suppression of aqueous humor.

Embodiment I-84. The method of embodiment I-79, wherein the first mechanism of action is increasing the drainage of aqueous humor through the trabeculocanicular pathway and the second mechanism of action is increasing the drainage of aqueous humor through the uveoscleral pathway.

Embodiment I-85. The method of embodiment I-79, wherein the first and second mechanisms of action are increasing the drainage of aqueous humor through the trabeculocanicular pathway.

Embodiment I-86. The method of embodiment I-79, wherein the first and second mechanism of action are increasing the drainage of aqueous humor through the uveoscleral pathway.

Embodiment I-87. The intraocular implant of embodiment I-1, wherein the first end of the elongate implant body is positioned in the sulcus.

Embodiment I-88. The intraocular implant of embodiment I-1, wherein the elongate implant body traverses the sulcus and extends less than about 2 mm, less than about 1 mm, less than about 0.5 mm, or less than about 0.25 mm from the sulcus into the posterior chamber.

Embodiment I-89. A method for treating a condition of an eye of a subject, the method comprising:

advancing a drug-eluting implant through a sclera of the eye;

positioning the drug-eluting implant fully intramurally in the eye with at least a portion of the drug-eluting implant in a limbus of the eye; and delivering a drug from the drug-eluting implant to an anterior chamber of the eye to reduce a symptom of the condition of the eye.

Embodiment I-90. The method of embodiment I-89, wherein the drug-eluting implant comprises an elongate implant body comprising a first end and a second end.

Embodiment I-91. The method of embodiment I-90, wherein the first end of the elongate implant body is positioned in the limbus and the second end is positioned in the sclera.

Embodiment I-92. The method of embodiment I-90, wherein the first end of the elongate implant body is positioned in the cornea and the second end is positioned in the limbus.

Embodiment I-93. The method of embodiment I-90, wherein the elongate implant body traverses the limbus, the first end of the elongate implant body is positioned in a cornea of the eye, and the second end is positioned in the sclera.

Embodiment I-94. The method of embodiment I-89, wherein advancing the drug-eluting implant comprises advancing a portion of a delivery device through a sclera of the eye, wherein the drug-eluting implant is disposed within the delivery device.

Embodiment I-95. The method of embodiment I-94, wherein the drug-eluting implant is disposed within a cannula of the delivery device.

Embodiment I-96. The method of embodiment I-95, wherein the drug-eluting implant is disposed about 0.5 mm to about 1.0 mm from a distal tip of the cannula.

Embodiment I-97. The method of embodiment I-94, wherein the distal tip of the cannula enters the anterior chamber during positioning of the drug-eluting implant.

Embodiment I-98. The method of embodiment I-94, wherein positioning the drug-eluting implant comprises advancing a distal tip of the cannula about 0.5 mm to about 1.0 mm into the anterior chamber.

Embodiment I-99. The method of embodiment I-94, wherein positioning the drug-eluting implant comprises retracting the cannula.

Embodiment I-100. The method of embodiment I-99, wherein the cannula is retracted via operation of an actuator of the delivery device.

Embodiment I-101. The method of embodiment I-99, wherein the drug-eluting implant is released from the delivery device upon retraction of the cannula.

Embodiment I-102. The method of embodiment I-95, wherein the drug-eluting implant is advanced and/or positioned using loupes, a slit lamp, or a surgical microscope.

Embodiment I-103. The method of embodiment I-102, wherein positioning further comprises visualizing the distal tip of the cannula in the anterior chamber of the eye using loupes, a slit lamp, or a surgical microscope.

Embodiment I-104. The method of embodiment I-89, wherein the method further comprises fixing a position of the drug-eluting implant to a tissue of the eye using at least one anchoring element.

Embodiment I-105. The method of embodiment I-104, wherein the at least one anchoring element is positioned in and fixed to the limbus.

Embodiment I-106. The method of embodiment I-104, wherein the at least one anchoring element is positioned in and coupled to the sclera.

Embodiment I-107. The method of embodiment I-104, wherein the at least one anchoring element comprises one or more of surface ridges, knobs, ribs, bulbs, and barbs.

Embodiment I-108. The method of embodiment I-89, wherein the drug-eluting implant does not enter the anterior chamber.

Embodiment I-109. The method of embodiment I-89, wherein the drug diffuses through the limbus or the sclera.

Embodiment I-110. The method of embodiment I-109, wherein the drug diffuses to the anterior and posterior chamber of the eye.

Embodiment I-111. The method of embodiment I-109, wherein the drug diffuses through the limbus to the anterior chamber and the cornea.

Embodiment I-112. The method of embodiment I-89, wherein the drug is a glaucoma drug.

Embodiment I-113. The method of embodiment I-112, wherein the drug is one or more of travoprost, bimatoprost, latanoprost, or unoprostone.

Embodiment I-114. The method of embodiment I-89, wherein the drug-eluting implant is cylindrical, a rectangular prism, or a sheet.

Embodiment I-115. The method of embodiment I-114, wherein the drug-eluting implant is from about 0.5 mm to about 2 mm in length.

Embodiment I-116. The method of embodiment I-115, wherein the drug-eluting implant is from about 1 mm to about 1.5 mm in length.

Embodiment I-117. The method of embodiment I-114, wherein the drug-eluting implant is from about 0.1 mm to about 0.5 mm wide.

Embodiment I-118. The method of embodiment I-117, wherein the drug-eluting implant is from about 0.2 mm to about 0.3 mm wide.

Embodiment I-119. The method of embodiment I-89, wherein the drug-eluting implant comprises poly(lactic-co-glycolic acid) (PLGA), poly(lactic acid) (PLA), or poly(glycolic acid) (PGA).

Embodiment I-120. A method of placing a drug-eluting implant, comprising a drug, at least partially within a limbus of an eye of a subject, the method comprising:

advancing a distal tip of a cannula of a delivery device through a sclera and the limbus into an anterior chamber of the eye, wherein the drug-eluting implant is disposed within the cannula; and retracting the cannula and releasing the drug-eluting implant at least partially within the limbus.

Embodiment I-121. The method of embodiment I-120, wherein the drug-eluting implant comprises an elongate implant body comprising a first end and a second end.

Embodiment I-122. The method of embodiment I-120, wherein the drug-eluting implant comprises a drug-eluting matrix comprising the drug.

Embodiment I-123. The method of embodiment I-122, wherein the drug-eluting matrix comprises a polymer.

Embodiment I-124. The method of embodiment I-120, wherein the drug-eluting implant is erodible.

Embodiment I-125. The method of embodiment I-120, wherein advancing the distal tip of the cannula comprises entering the sclera posterior to the limbus.

Embodiment I-126. The method of embodiment I-125, wherein the distal tip of the cannula enters the sclera about 2 mm to about 3 mm posterior to the limbus.

Embodiment I-127. The method of embodiment I-120, wherein the distal tip of the cannula is advanced about 0.5 mm to about 1.0 mm into the anterior chamber.

Embodiment I-128. The method of embodiment I-120, wherein the drug-eluting implant is disposed within the cannula about 0.5 mm to about 1.0 mm proximal to the distal tip of the cannula.

Embodiment I-129. The method of embodiment I-120, wherein after releasing the drug-eluting implant from the delivery device, the drug-eluting implant resides fully intramurally.

Embodiment I-130. The method of embodiment I-129, wherein after releasing the drug-eluting implant from the delivery device, the drug-eluting implant is positioned fully within the limbus.

Embodiment I-131. The method of embodiment I-121, wherein after releasing the drug-eluting implant from the delivery device, the first end of the elongate implant body is positioned in the limbus and the second end is positioned in the sclera.

Embodiment I-132. The method of embodiment I-121, wherein after releasing the drug-eluting implant from the delivery device, the first end of the elongate implant body is positioned in the cornea and the second end is positioned in the limbus.

Embodiment I-133. The method of embodiment I-121, wherein after releasing the drug-eluting implant from the delivery device, the elongate implant body traverses the limbus, the first end of the elongate implant body is positioned in a cornea of the eye, and the second end is positioned in the sclera.

Embodiment I-134. The method of embodiment I-120, wherein the method further comprises positioning the drug-eluting implant at least partially within the limbus prior to retracting the cannula.

Embodiment I-135. The method of embodiment I-134, wherein positioning the drug-eluting implant comprises visualizing the distal tip of the cannula in the anterior chamber.

Embodiment I-136. The method of embodiment I-135, wherein the distal tip of the cannula is confirmed, via visualization, to be about 0.5 mm to about 1.0 mm into the anterior chamber.

Embodiment I-137. The method of embodiment I-135, wherein the position of the distal tip of the cannula is confirmed, via visualization through an anterior portion of the, eye using loupes, a slit lamp, or a surgical microscope.

Embodiment I-138. The method of embodiment I-120, wherein the cannula is retracted via operation of an actuator of the delivery device.

Embodiment I-139. The method of embodiment I-138, wherein the drug-eluting implant is released from the delivery device upon retraction of the cannula.

Embodiment I-140. The method of embodiment I-138, wherein the actuator comprises one or more of a button, a knob, and a slider.

Embodiment I-141. The method of embodiment I-120, wherein the delivery device comprises a spring configured to retract the cannula.

Embodiment I-142. The method of embodiment I-120, wherein the drug-eluting implant does not enter the anterior chamber.

Embodiment I-143. The method of embodiment I-120, wherein the drug diffuses through the limbus or the sclera.

Embodiment I-144. The method of embodiment I-143, wherein the drug diffuses to the anterior and posterior chamber of the eye.

Embodiment I-145. The method of embodiment I-143, wherein the drug diffuses through the limbus to the anterior chamber and the cornea.

Embodiment I-146. The method of embodiment I-120, wherein the drug is a glaucoma drug.

Embodiment I-147. The method of embodiment I-120, wherein the drug is one or more of travoprost, bimatoprost, latanoprost, or unoprostone.

Embodiment I-148. The method of embodiment I-120, wherein the drug-eluting implant is cylindrical, a rectangular prism, or a sheet.

Embodiment I-149. The method of embodiment I-148, wherein the drug-eluting implant is from about 0.5 mm to about 2 mm in length.

Embodiment I-150. The method of embodiment I-149, wherein the drug-eluting implant is from about 1 mm to about 1.5 mm in length.

Embodiment I-151. The method of embodiment I-148, wherein the drug-eluting implant is from about 0.1 mm to about 0.5 mm wide.

Embodiment I-152. The method of embodiment I-151, wherein the drug-eluting implant is from about 0.2 mm to about 0.3 mm wide.

Embodiment I-153. The method of embodiment I-120, wherein the drug-eluting implant comprises poly(lactic-co-glycolic acid) (PLGA), poly(lactic acid) (PLA), or poly(glycolic acid) (PGA).

Embodiment I-154. The method of embodiment I-120, wherein the drug-eluting implant resides partially in the subconjunctival space.

EXAMPLES

Example 1

An Ab-Externo Method for Delivering an Intraocular Implant

A delivery device comprising a needle may be inserted into the sclera about 2 to about 2.5 mm posterior to the limbus to a guarded/controlled depth (about 0.5 to about 2 mm into eye). Via actuation, a pusher rod advances the implant in the needle via across the sulcus, with the implant tip ending in sulcus/posterior chamber. An anchoring element opens or expands in sulcus, and the needle is withdrawn. In some variations, the implant may comprise a thread-like end, which may be positioned on the conjunctiva and exposed. The conjunctiva may then be lifted (e.g., with forceps) to tent over or otherwise cover the exposed end of the implant, allowing the end to slip into the subconjunctival space. Alternatively, the device may be placed using a similar technique, such that the tip of the implant resides in Berger's space or the Canal of Petit. Any of the drug-eluting implants described herein may be used, such as, for example, a fully erodible implant.

Example 2

An Ab-Externo Method for Delivering an Intraocular Implant

A delivery device comprising a needle with two marks may be inserted into the limbus and advanced into the sclera to create an about 3 mm tunnel. It is then withdrawn about 2 mm. An actuator (e.g., an actuation button, slider, etc.) deploys the implant contained within the needle into sclera/limbal zone. In some embodiments, the final implant length may be about 1 mm, about 2 mm, about 3 mm, about 4 mm, about 5 mm, or about 6 mm.

Example 3

An Ab-Externo Method for Delivering an Intraocular Implant

A delivery device comprising a side-open needle (e.g., such delivery device (1500) comprising needle 1502 depicted in FIG. 15) may be inserted about 2.5 mm posterior to the limbus to a target depth (about 1.5 mm). Under direct visualization, the implant may be advanced through the needle via a push rod until the first end of the implant is inside the eye and the push rod is fully advanced. The needle may then be withdrawn, leaving the implant within the eye. In some variations, the implant may have a thread-like end that may now be on the conjunctiva and exposed. The conjunctiva may then be lifted (e.g., with forceps) to tent over or otherwise cover the implant, allowing the end of the implant to slip into the subconjunctival space. Any of the drug-eluting implants described herein may be used, such as, for example, a fully erodible implant.

Example 4

An Ab-Interno Method for Delivering an Intraocular Implant

In another exemplary embodiment, a delivery device comprising a needle may be inserted through the limbus, through the pupil, behind the iris, into the sulcus, and through the sclera, stopping in the subconjunctival space. The implant may then be advanced with a push rod, via an actuator of the delivery device, through the needle until a portion of the implant is visible through sclera. At this point, the extra-scleral portion of implant is either under or on the conjunctiva. The needle may be withdrawn, and the second end of the implant body, which may comprise one or more anchoring features preventing it from being pulled back into eye, may be positioned outside of the sclera. In some variations, the implant may have a thread-like end that may now be on the conjunctiva and exposed. The conjunctiva may then be lifted, e.g., with forceps, to tent over or otherwise cover the implant, allowing the end of the implant to slip into the subconjunctival space. Any of the drug-eluting implants described herein may be used, such as, for example, a fully erodible implant.

Example 5

An Ab-Externo Method for Delivering an Intraocular Implant

In another exemplary embodiment, a tunnel or pocket is created in the wall of the eye that is about 50% the depth of the tissue (e.g., cornea, sclera, and/or limbus) using an instrument such as a corneal separator (for the creation of an intramural channel or tunnel in the cornea, limbus, or sclera) or a femtosecond laser. Next a delivery device is used to deploy the implant into this preformed space.

Example 6

An Ab-Interno Method for Delivering an Intraocular Implant

In another exemplary embodiment, a delivery device comprising a needle may be inserted through the cornea, across the anterior chamber towards the anterior chamber angle. A needle is used to enter the suprachoroidal space where the drug-eluting implant is placed completely in the suprachoroidal space. Alternatively, the drug-eluting implant may be partially placed within the suprachoroidal space, with a portion of the drug-eluting implant residing within the anterior chamber. Any of the drug-eluting implants described herein may be used, such as, for example, a fully erodible implant.

Example 7

An Exemplary Erodible Implant to Lower Elevated Intraocular Pressure

In one exemplary embodiment, an intraocular implant configured to be implanted fully within the sclera comprises an implant body comprising a core of one or more erodible drug-eluting matrices of one or more drugs for treating glaucoma. The implant body may be comprised of an erodible polymer configured to release the one or more drugs into the scleral tissue, where it may diffuse further into an internal chamber of the eye (e.g., anterior chamber). The rate of elution of the one or more drugs may be constant or may change over time (e.g., due to the erosion of the erodible implant body). The implant may be configured such that the one or more drugs elute faster from the drug-eluting matrices than the implant body erodes.

Example 8

An Ab-Externo Method of Positioning and Delivering an Intraocular Implant Residing Intramurally in the Eye In one exemplary embodiment, an intraocular implant is configured to reside intramurally in the eye with at least a portion of the implant in a limbus of the eye. The implant is delivered via a delivery device, where it is disposed within a cannula. The implant is disposed about 0.5 mm to about 1.0 mm from the distal tip of the cannula. The cannula containing the implant is advanced through the sclera posterior to the limbus of an eye. The cannula is then further advanced into the anterior chamber to a depth corresponding to the offset of the implant from the distal tip of the cannula (e.g., about 0.5 mm to about 10.0 mm) in order to position the implant at least partially in the limbus without the implant entering the anterior chamber. The implant is advanced or positioned using loupes, a slit lamp, or a surgical microscope. Once the distal tip of the cannula is visualized within the anterior chamber and confirmed to be at the appropriate depth, the cannula is retracted via at least one actuator of the delivery device, releasing the implant intramurally upon retraction of the cannula. The implant may have one or more anchoring elements, including anchoring elements that deploy intramurally once the cannula of the delivery device is retracted.

Example 9

Investigation of Bimatoprost-PLGA Drug-Eluting Implants in Pigs

Poly(lactic-co-glycolic acid) (PLGA) implants comprising bimatoprost were implanted into the eyes of 3 month old Yucatan pigs (6 pigs total). Prior to delivering the implant to either the sclera (fully intrascleral; "intrascleral arm") or partially in the limbus (one end residing in the limbus, one end residing in the sclera; "limbal arm"), the pigs were placed under general anesthesia, and a lid speculum was inserted. Intraocular pressure was checked, and corneal thickness was checked in 4 quadrants, and centrally, using ultrasonic corneal pachymetry. The lid speculum was then removed.

In each of the 6 pigs, the right eye received one implant, and the left eye received 2 implants. In order to accomplish this, betadine drops were placed onto the left eyes of each pig and an eyelid speculum is inserted. A surgical operating microscope was positioned to visualize the implantation. Each eye was infraducted with a traction suture. A small conjunctival peritomy was created, and the sclera was marked with gentian violet-tipped calipers 2 mm posterior to the limbus. 10-0 nylon marking sutures were then placed 3-4 mm posterior to the limbus. A 27 G needle on a TB syringe was used to preform a tunnel for implantation toward the anterior chamber (group 1) or across the sclera (group 2). The implant was then deployed into the preformed tunnel, and the traction suture was released. Polymyxin-trimethoprim and tobramycin-dexamethasone drops were then placed in each eye, and the speculum was removed. The procedure was then repeated with two implants in each pig's right eye.

At week 2, the pigs were examined for redness, inflammation, eye rubbing, miosis, and squinting.

At month 1, the pigs were examined, and one pig from each group was euthanized and the eyes were removed and placed in formalin for pathology. Aqueous samples from each of the 6 pigs were collected and analyzed for the presence of bimatoprost and Bimatoprost Acid (a metabolite of bimatoprost). At weeks 3, 10, and 20, the remaining pigs in each group were examined for redness, inflammation, eye rubbing, miosis, and squinting, as above.

At month 3, the remaining pigs were examined and aqueous samples collected (as above), and one of the remaining pigs from each group was euthanized (as above) for pathology.

Figure 24A:
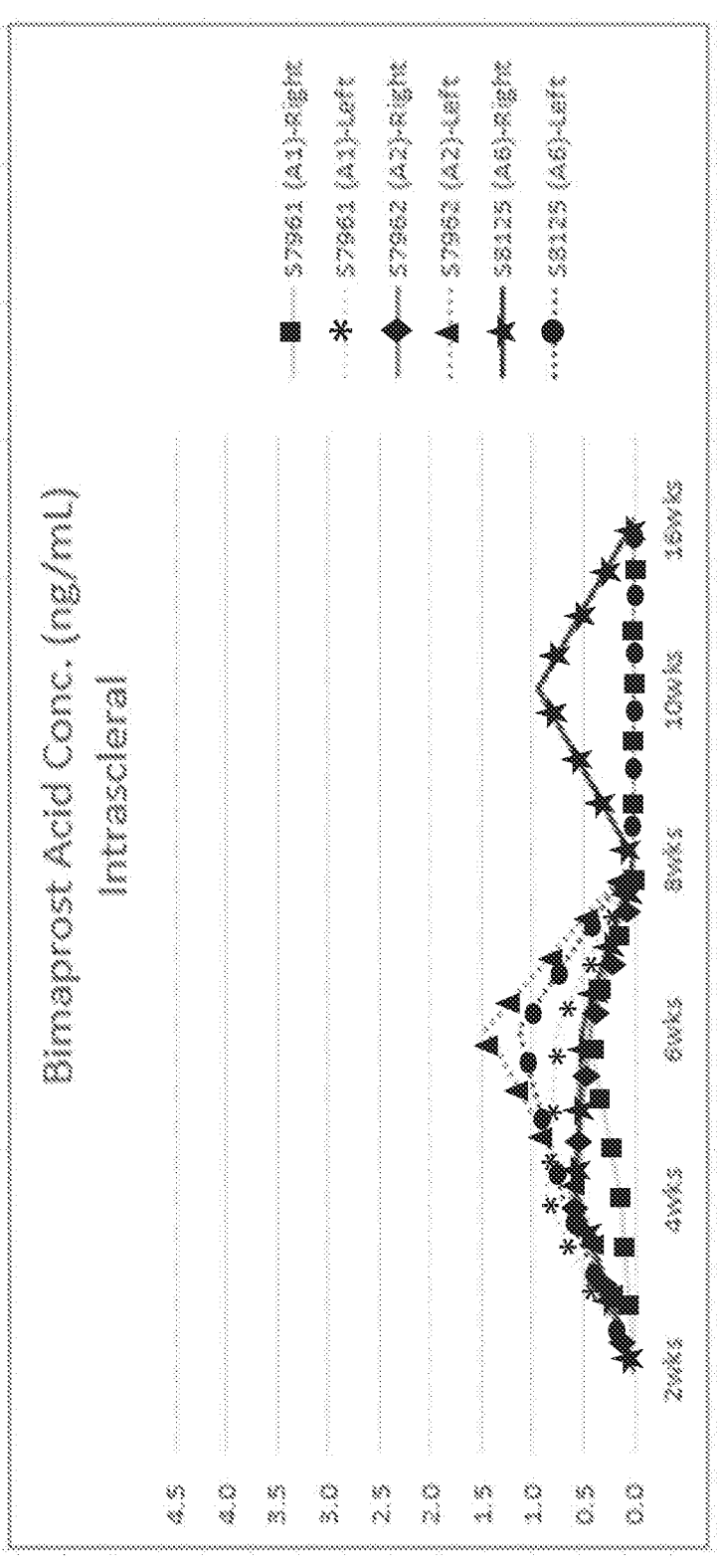
FIG. 24A and FIG. 24B show the concentrations of bimatoprost and the bimatoprost acid metabolite, respectively, for three pigs (A1, A2, and A6) implanted with the intrascleral implant in an animal study.
Figure 24B:
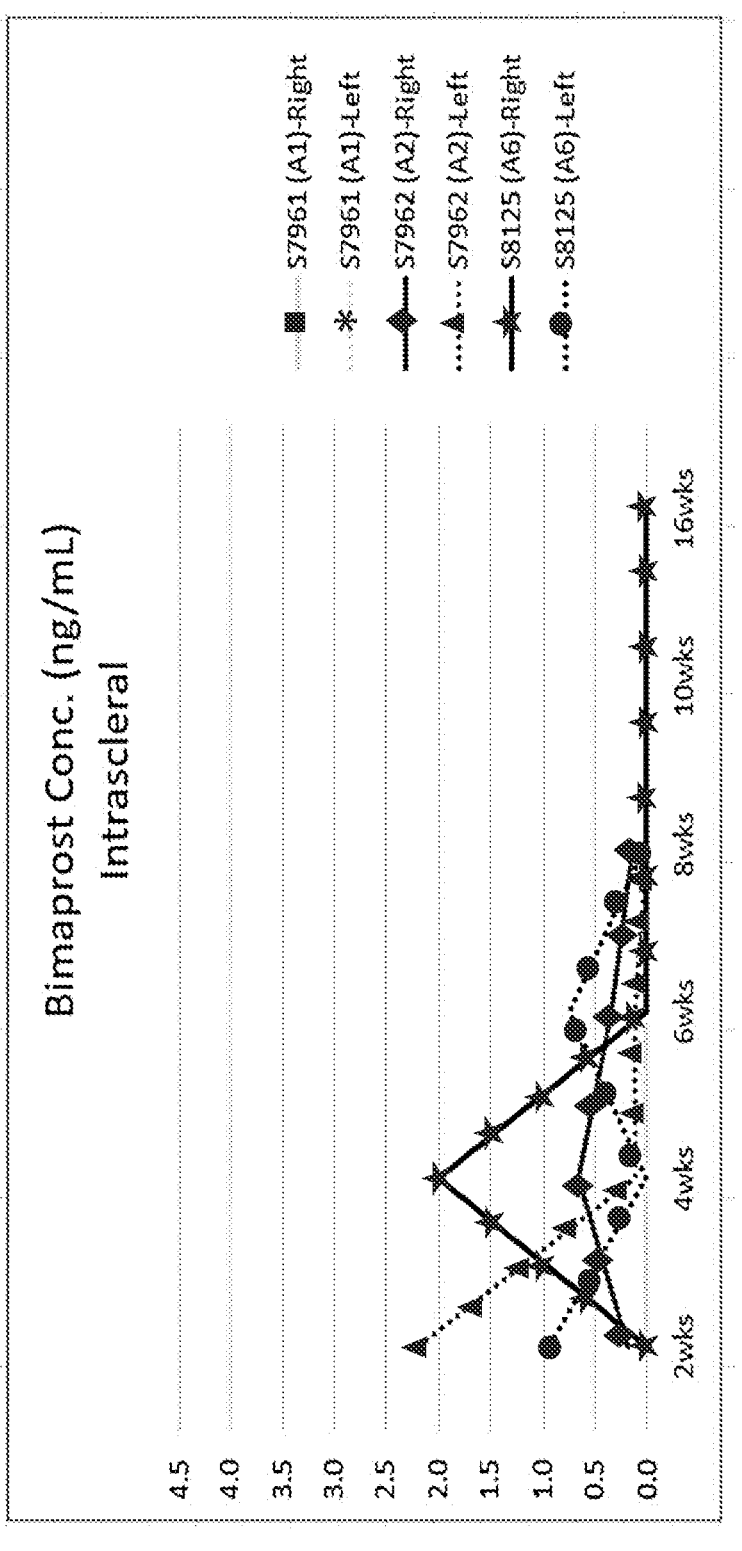
Figure 24C:
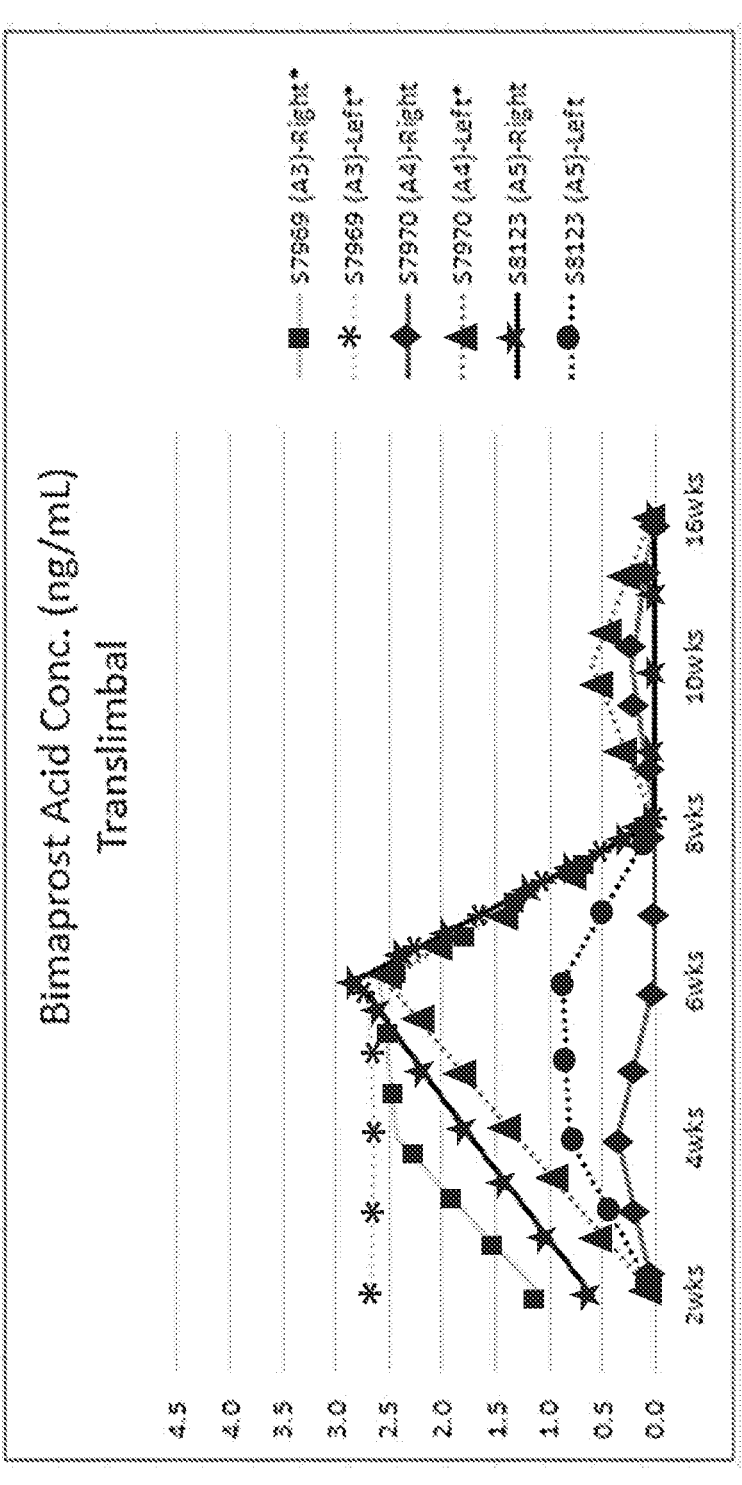
FIGS. 24C and 24D show advancement of the distal tip of the cannula into and through the sclera and limbus, respectively.
Figure 24D:
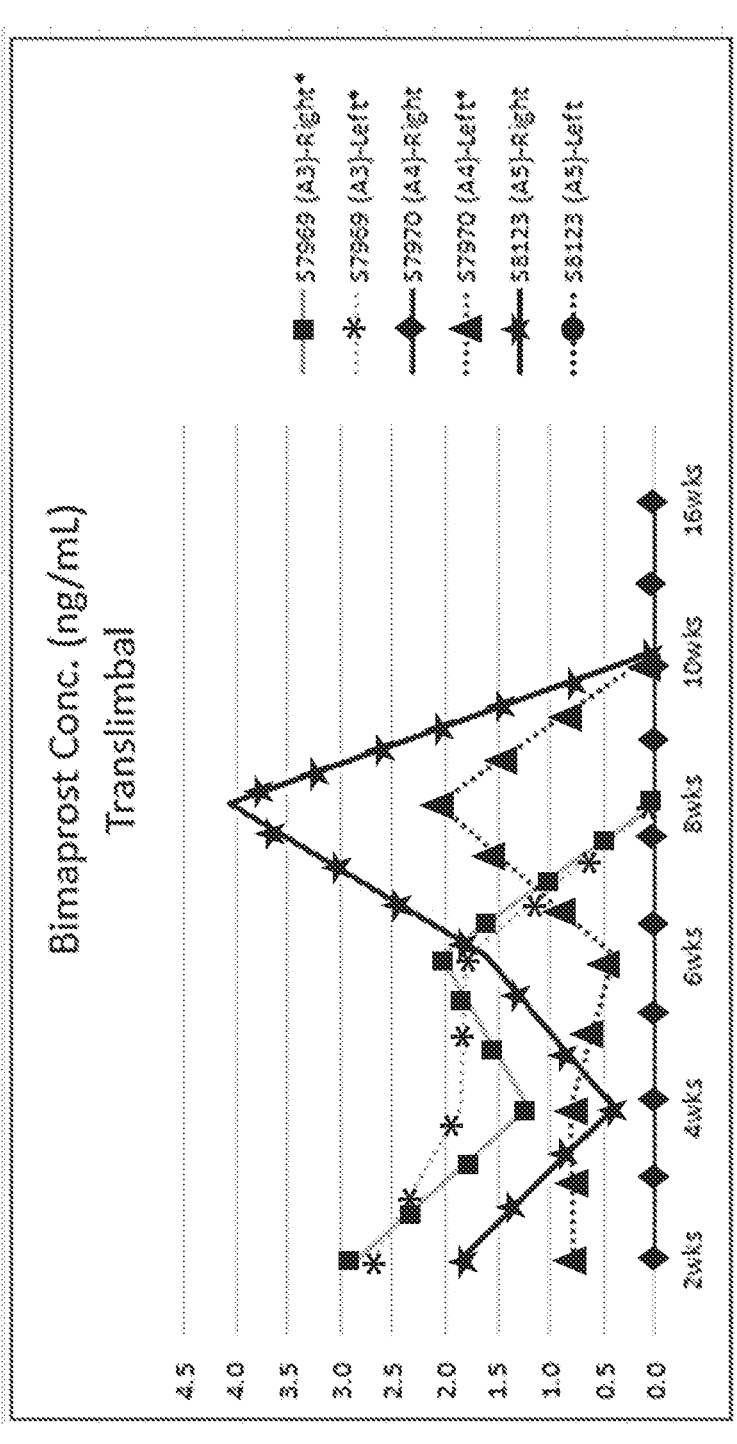

The histopathology of the eyes is evaluated, as is the concentration of bimatoprost, and metabolites thereof, in the anterior chambers. The concentrations of bimatoprost and the bimatoprost acid metabolite in the anterior chamber of each pig's eyes are shown in FIGS. 24A-24D, at the time points described above. FIG. 24A and FIG. 24B show the concentrations of bimatoprost and the bimatoprost acid metabolite, respectively, for the three pigs (A1, A2, and A6) implanted with the intrascleral implant. FIG. 24C and FIG. 24D show the concentrations of bimatoprost and the bimatoprost acid metabolite, respectively, for the three pigs (A3, A4, and A5) implanted with the limbal implant. As demonstrated in these data sets, bimatoprost was detectable in the aqueous humor of both intrascleral and limbal arms. Additionally bimatoprost had both higher and more sustained aqueous levels in the limbal arm compared to the intrascleral arm. Similarly, Bimatoprost Acid was detectable in both animal arms and was also detected at a higher concentration in the limbal arm compared to the intrascleral arm.

At month 6, the remaining pig from each group is examined and aqueous samples are collected (as above), and each of the remaining pigs is euthanized (as above) for pathology. At this point, the histopathology of the eyes is evaluated, as is the concentration of bimatoprost, and metabolites thereof, in the anterior chambers.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to explain the principles of the invention and its practical applications, they thereby enable others skilled in the art to utilize the invention and various embodiments with various modifications as are suited to the particular use contemplated. It is intended that the following claims and their equivalents define the scope of the invention.

The invention claimed is:

1. A method of placing a drug-eluting implant, comprising a drug, at least partially within a limbus of an eye of a subject, the method comprising:
   advancing a distal tip of a cannula of a delivery device through a sclera and the limbus into an anterior chamber of the eye, wherein the drug-eluting implant is disposed within the cannula; and
   retracting the cannula and releasing the drug-eluting implant at least partially within the limbus, wherein after releasing the drug-eluting implant from the delivery device, the drug-eluting implant resides partially in the subconjunctival space.

2. The method of claim 1, wherein the drug-eluting implant comprises a drug-eluting matrix comprising the drug.

3. The method of claim 2, wherein the drug-eluting matrix comprises a polymer.

4. The method of claim 1, wherein the drug-eluting implant is erodible.

5. The method of claim 1, wherein advancing the distal tip of the cannula comprises entering the sclera posterior to the limbus.

6. The method of claim 5, wherein the distal tip of the cannula enters the sclera about 2 mm to about 3 mm posterior to the limbus.

7. The method of claim 1, wherein the distal tip of the cannula is advanced about 0.5 mm to about 1.0 mm into the anterior chamber.

8. The method of claim 1, wherein the drug-eluting implant is disposed within the cannula about 0.5 mm to about 1.0 mm proximal to the distal tip of the cannula.

9. The method of claim 1, wherein the method further comprises positioning the drug-eluting implant at least partially within the limbus prior to retracting the cannula.

10. The method of claim 9, wherein positioning the drug-eluting implant comprises visualizing the distal tip of the cannula in the anterior chamber.

11. The method of claim 10, wherein the distal tip of the cannula is confirmed, via visualization, to be about 0.5 mm to about 1.0 mm into the anterior chamber.

12. The method of claim 1, wherein the cannula is retracted via operation of an actuator of the delivery device.

13. The method of claim 12, wherein the drug-eluting implant is released from the delivery device upon retraction of the cannula.

14. The method of claim 1, wherein the delivery device comprises a spring configured to retract the cannula.

15. The method of claim 1, wherein the drug-eluting implant does not enter the anterior chamber.

16. The method of claim 1, wherein the drug diffuses through the limbus or the sclera.

17. The method of claim 16, wherein the drug diffuses to the anterior and posterior chamber of the eye.

18. The method of claim 16, wherein the drug diffuses through the limbus to the anterior chamber and the cornea.

19. The method of claim 1, wherein the drug is a glaucoma drug.

20. The method of claim 1, wherein the drug is one or more of travoprost, bimatoprost, latanoprost, or unoprostone.

21. The method of claim 1, wherein the drug-eluting implant is cylindrical, a rectangular prism, or a sheet.

22. The method of claim 1, wherein the drug-eluting implant is from about 0.5 mm to about 2 mm in length.

23. The method of claim 1, wherein the drug-eluting implant comprises poly(lactic-co-glycolic acid) (PLGA), poly(lactic acid) (PLA), or poly(glycolic acid) (PGA).

24. A method of placing a drug-eluting implant, comprising a drug, at least partially within a limbus of an eye of a subject, the method comprising:
   advancing a distal tip of a cannula of a delivery device through a sclera and the limbus into an anterior chamber of the eye, wherein the drug-eluting implant is disposed within the cannula; and
   retracting the cannula and releasing the drug-eluting implant at least partially within the limbus, wherein the drug diffuses through the limbus or the sclera.

25. The method of claim 24, wherein the drug diffuses to the anterior and posterior chamber of the eye.

26. The method of claim 24, wherein the drug diffuses through the limbus to the anterior chamber and the cornea.

27. The method of claim 24, wherein the drug-eluting implant comprises a drug-eluting matrix comprising the drug.

28. The method of claim 27, wherein the drug-eluting matrix comprises a polymer.

29. The method of claim 24, wherein the drug-eluting implant is erodible.

30. The method of claim 24, wherein advancing the distal tip of the cannula comprises entering the sclera posterior to the limbus.

31. The method of claim 30, wherein the distal tip of the cannula enters the sclera about 2 mm to about 3 mm posterior to the limbus.

32. The method of claim 24, wherein the distal tip of the cannula is advanced about 0.5 mm to about 1.0 mm into the anterior chamber.

33. The method of claim 24, wherein the drug-eluting implant is disposed within the cannula about 0.5 mm to about 1.0 mm proximal to the distal tip of the cannula.

34. The method of claim 24, wherein after releasing the drug-eluting implant from the delivery device, the drug-eluting implant resides fully intramurally.

35. The method of claim 24, wherein the drug-eluting implant comprises an elongate implant body comprising a first end and a second end, and after releasing the drug-eluting implant from the delivery device, the first end is positioned in the limbus and the second end is positioned in the sclera.

36. The method of claim 24, wherein the drug-eluting implant comprises an elongate implant body comprising a first end and a second end, and after releasing the drug-eluting implant from the delivery device, the first end is positioned in the cornea and the second end is positioned in the limbus.

37. The method of claim 24, wherein the drug-eluting implant comprises an elongate implant body comprising a first end and a second end, and after releasing the drug-eluting implant from the delivery device, the elongate implant body traverses the limbus, the first end is positioned in a cornea of the eye, and the second end is positioned in the sclera.

38. The method of claim 24 wherein the method further comprises positioning the drug-eluting implant at least partially within the limbus prior to retracting the cannula.

39. The method of claim 38, wherein positioning the drug-eluting implant comprises visualizing the distal tip of the cannula in the anterior chamber.

40. The method of claim 39, wherein the distal tip of the cannula is confirmed, via visualization, to be about 0.5 mm to about 1.0 mm into the anterior chamber.

41. The method of claim 24, wherein the cannula is retracted via operation of an actuator of the delivery device.

42. The method of claim 41, wherein the drug-eluting implant is released from the delivery device upon retraction of the cannula.

43. The method of claim 24, wherein the delivery device comprises a spring configured to retract the cannula.

44. The method of claim 24, wherein the drug-eluting implant does not enter the anterior chamber.

45. The method of claim 24, wherein the drug is a glaucoma drug.

46. The method of claim 24, wherein the drug is one or more of travoprost, bimatoprost, latanoprost, or unoprostone.

47. The method of claim 24, wherein the drug-eluting implant is cylindrical, a rectangular prism, or a sheet.

48. The method of claim 24, wherein the drug-eluting implant is from about 0.5 mm to about 2 mm in length.

49. The method of claim 24, wherein the drug-eluting implant comprises poly(lactic-co-glycolic acid) (PLGA), poly(lactic acid) (PLA), or poly(glycolic acid) (PGA).

50. The method of claim 49, wherein the drug-eluting implant resides partially in the subconjunctival space.

51. A method of placing a drug-eluting implant, comprising a drug, at least partially within a limbus of an eye of a subject, the method comprising:

advancing a distal tip of a cannula of a delivery device through a sclera and the limbus into an anterior chamber of the eye, wherein the drug-eluting implant is disposed within the cannula; and retracting the cannula and releasing the drug-eluting implant at least partially within the limbus, wherein the cannula is retracted via operation of an actuator of the delivery device.

52. The method of claim 51, wherein the drug-eluting implant is released from the delivery device upon retraction of the cannula.

53. The method of claim 51, wherein the drug-eluting implant is erodible.

54. The method of claim 51, wherein the drug is a glaucoma drug.

55. The method of claim 51, wherein the drug is one or more of travoprost, bimatoprost, latanoprost, or unoprostone.

56. The method of claim 51, wherein the drug-eluting implant comprises poly(lactic-co-glycolic acid) (PLGA), poly(lactic acid) (PLA), or poly(glycolic acid) (PGA).

57. A method of placing a drug-eluting implant, comprising a drug, at least partially within a limbus of an eye of a subject, the method comprising:

advancing a distal tip of a cannula of a delivery device through a sclera and the limbus into an anterior chamber of the eye, wherein the drug-eluting implant is disposed within the cannula; and retracting the cannula and releasing the drug-eluting implant at least partially within the limbus, wherein the delivery device comprises a spring configured to retract the cannula.

58. The method of claim 57, wherein the drug-eluting implant is released from the delivery device upon retraction of the cannula.

59. The method of claim 57, wherein the drug-eluting implant is erodible.

60. The method of claim 57, wherein the drug is a glaucoma drug.

61. The method of claim 57, wherein the drug is one or more of travoprost, bimatoprost, latanoprost, or unoprostone.

62. The method of claim 57, wherein the drug-eluting implant comprises poly(lactic-co-glycolic acid) (PLGA), poly(lactic acid) (PLA), or poly(glycolic acid) (PGA).

63. A method of placing a drug-eluting implant, comprising a drug, at least partially within a limbus of an eye of a subject, the method comprising:

advancing a distal tip of a cannula of a delivery device through a sclera and the limbus into an anterior chamber of the eye, wherein the drug-eluting implant is disposed within the cannula; and retracting the cannula and releasing the drug-eluting implant at least partially within the limbus, wherein the drug-eluting implant does not enter the anterior chamber.

64. The method of claim 63, wherein the drug-eluting implant is released from the delivery device upon retraction of the cannula.

65. The method of claim 63, wherein the drug-eluting implant is erodible.

66. The method of claim 63, wherein the drug is a glaucoma drug.

67. The method of claim 63, wherein the drug is one or more of travoprost, bimatoprost, latanoprost, or unoprostone.

68. The method of claim 63, wherein the drug-eluting implant comprises poly(lactic-co-glycolic acid) (PLGA), poly(lactic acid) (PLA), or poly(glycolic acid) (PGA).

\* \* \* \* \*